(12) United States Patent
Rhiel et al.

(10) Patent No.: US 10,676,733 B2
(45) Date of Patent: Jun. 9, 2020

(54) METHODS FOR NON-COVALENT FC-DOMAIN-CONTAINING PROTEIN DISPLAY ON THE SURFACE OF CELLS AND METHODS OF SCREENING THEREOF

(71) Applicant: Merck Patent GmbH, Darmstadt (DE)

(72) Inventors: Laura Rhiel, Frankfurt am Main (DE); Stefan Becker, Darmstadt (DE); Ralf Guenther, Griesheim (DE); Bjoern Hock, Maintal (DE); Daniel Helman, Qiryat Ono (IL); Mira Toister-Achituv, Rehovot (IL); Simon Krah, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 183 days.

(21) Appl. No.: 15/522,108

(22) PCT Filed: Oct. 27, 2015

(86) PCT No.: PCT/EP2015/002125
§ 371 (c)(1),
(2) Date: Apr. 26, 2017

(87) PCT Pub. No.: WO2016/066260
PCT Pub. Date: May 6, 2016

(65) Prior Publication Data
US 2018/0298374 A1 Oct. 18, 2018

(30) Foreign Application Priority Data
Oct. 28, 2014 (EP) .................................... 14003649

(51) Int. Cl.
*C40B 30/06* (2006.01)
*C12N 15/10* (2006.01)
(Continued)

(52) U.S. Cl.
CPC ........ *C12N 15/1037* (2013.01); *C07K 14/195* (2013.01); *C07K 14/315* (2013.01);
(Continued)

(58) Field of Classification Search
None
See application file for complete search history.

(56) References Cited

U.S. PATENT DOCUMENTS

| | | |
|---|---|---|
| 5,328,985 A | 7/1994 | Sano et al. |
| 6,150,584 A | 11/2000 | Kucherlapati et al. |

FOREIGN PATENT DOCUMENTS

| | | |
|---|---|---|
| EP | 0 667 165 B1 | 3/2002 |
| EP | 2 617 827 A1 | 7/2013 |

(Continued)

OTHER PUBLICATIONS

Alivisatos, A. P., "Perspectives on the Physical Chemistry of Semiconductor Nanocrystals," *J. Phys. Chem.*, 1996, vol. 100, pp. 13226-13239.
(Continued)

*Primary Examiner* — Christian C Boesen
(74) *Attorney, Agent, or Firm* — Womble Bond Dickinson (US) LLP

(57) ABSTRACT

The present invention provides methods for the non-covalent surface display of proteins of interest (POI), in particular for Fc-domain containing proteins such as antibodies. The inventive method may be used to screen and select proteins of interest of a desired phenotype. The present invention further discloses polynucleotides and proteins and methods of producing the same, which may be used in carrying out the inventive method.

24 Claims, 16 Drawing Sheets

Specification includes a Sequence Listing.

(51) Int. Cl.
    C07K 14/36      (2006.01)
    C07K 14/315     (2006.01)
    C07K 14/195     (2006.01)
    C07K 16/00      (2006.01)
    C12N 15/81      (2006.01)
(52) U.S. Cl.
    CPC ............ *C07K 14/36* (2013.01); *C07K 16/005* (2013.01); *C12N 15/1075* (2013.01); *C12N 15/81* (2013.01); *C07K 2319/00* (2013.01); *C07K 2319/02* (2013.01); *C07K 2319/22* (2013.01); *C07K 2319/70* (2013.01); *C40B 30/06* (2013.01)

(56)                References Cited

FOREIGN PATENT DOCUMENTS

| JP | 2013-233157 A | 11/2013 |
|----|---------------|---------|
| WO | WO 97/19957 A1 | 6/1997 |
| WO | WO 02/094852 A2 | 11/2002 |
| WO | WO 2008/028218 A1 | 3/2008 |
| WO | WO 2009/062942 A2 | 5/2009 |
| WO | WO 2010/005863 A1 | 1/2010 |
| WO | WO 2014/101287 A1 | 7/2014 |
| WO | WO 2014/106527 A1 | 7/2014 |

OTHER PUBLICATIONS

Alivisatos, A. P., "Semiconductor Clusters, Nanocrystals, and Quantum Dots," *Science*, 1996, vol. 271(5251), pp. 933-937.
Altschul, S., et anon., "Optimal Sequence Alignment Using Affine Gap Costs," *Bulletin of Mathematical Biology*, 1986, vol. 48(5/6), pp. 603-616.
Baek, D., et anon., "Construction of a Large Synthetic Human Fab Antibody Library on Yeast Cell Surface by Ooptimized Yeast Mating," *J. Microbiol. Biotechnol.*, 2014, vol. 24(3), pp. 408-420.
Barelle, C., et al., Chapter 6, "Shark Novel Antigen Receptors—The Next Generation of Biologic Therapeutics?," *Pharmaceutical Biotechnology*, edited by Carlos A. Guzmán and Giora Z. Feurerstein, 2009, Landes Biosicence and Springer Science Media.
Benatuil, L., et al., "An improved yeast transformation method for the generation of very large human antibody libraries," *Protein Engineering, Design & Selection*, 2010, vol. 23(4), pp. 155-159 (with Supplementary Methods).
Banhar, Itai, "Design of synthetic antibody libraries," *Expert Opinion on Biologial Therapy*, 2007, vol. 7(5), pp. 763-779.
Bentley, C., et al., "Arrayed antibody library technology for therapeutic biologic discovery," *Methods*, 2013, vol. 60, pp. 91-98.
Beste, G., et al., "Small antibody-like proteins with prescribed ligand specificities deried from the lipocalid fold," *Proc. Natl. Acad. Sci. USA*, 1999, vol. 96,pp. 1898-1903.
Binz, H., et al., "Desinging Repeat Proteins: Well-expressed, Soluble and Stable Proteins from Combinatorial Libraries of Consensus Ankyrin Repeat Proteins," *J. Mol. Biol.*, 2003, vol. 332, pp. 489-503.
Blaise, L., et al., "Construction and diversification of yeast cell surface displayed libraries by yeast mating: application to the affinity maturation of Fab antibody fragments," *Gene*, 2004, vol. 342, pp. 211-218.
Boder, E., et anon., "Yeast surface display for screening combinatorial polypeptide libraries," *Nature Biotechnology*, 1997, vol. 15, pp. 553-557.
Boder, E., et anon., "Yeast Surface Display for Directed Evolution of Protein Expression, Affinity, and Stability," *Methods in Enzymology*, 2000, vol. 328, pp. 430-444. Abstract only.
Boder, E., et al., "Directed evolution of antibody fragments with monovalent femtomolar antigen-binding affinity," *PNAS*, vol. 97(20), pp. 10701-10705.
Boder, E., et al., "Engineering antibodies by yeast display," *Archives of Biochemistry and Biophysics*, 2012, vol. 526, pp. 99-106

Bothmann, H., et anon., "The Periplasmic *Escherichia coli* Peptidylprolyl cis, trans-Isomerase FkpA," *The Journal of Biological Chemistry*, 2000, vol. 275(22), pp. 17100-17105.
Boyce, F., et anon., "Baculovius-mediated gene transfer into mammalian cells," *Proc. Natl. Acad. Sci. USA*, 1996, vol. 93, pp. 2348-2352.
Bowley, D., et al., "Antigen selection from an HIV-1 immune antibody library displayed on yeast yields many novel antibodies compared to selection from the same library displayed on phage," *Protein Engineering, Design & Selection*, 2007, vol. 20(2), pp. 81-90.
Deisenhofer, Johann, "Crystallographic Refinement and Atomic Models of a Human Fc Fragment and Its Complex with Fragment B of Protein A from *Staphylococcus aureus* at 2.9- and 2.8-521 Reoslution," *Biochemistry*, 1981 vol. 20(9), pp. 2361-2370.
Dorener, A., et al., "Therapeutic antibody engineering by high efficiency cell screeing," *FEBS Letters*, 2014, vol. 588, pp. 278-287.
Dong, J., et al., "A Single-Domain Llama Antibody Potently Inhibits the Enzymatic Activity of Botulinum Neurotoxin by Binding to the Non-Catalytic α-Exosite Binding Region," *J. Mol. Biol.*, 2010, vol. 397, pp. 1106-1118.
Dübel, S., et al., "Generating recombinant antibodies to the complete human proteome," *Trends in Biotechnology*, 2010, vol. 28(7), pp. 333-339.
Ebersbach, H., et al., "Affilin-Novel Binding Molecules Based on Human γ-B-Crystallin, and All β-Sheet Protein," *J. Mol. Biol.*, 2007, vol. 372, pp. 173-185.
Feldhaus, M., et al., "Flow-cytometric isolation of human antibodies from a nonimmune *Saccharomyces cerevisiae* surface display library," *Nature Biotechnology*, 2003, vol. 21, pp. 163-170.
Freitag, S., et al., "Structual studies of the streptavidin binding loop," *Protein Science*, 1997, vol. 6, Article 217 pp. 11157-1166.
Frenzel, A., et al., "Expression of recombinant antibodies," *Frontiers in Immunology*, 2013, vol. 4, pp. 1-20.
Fryer, J., et anon., "Three decades of fish cell culture: A current listing of cell lines derived from fishes," *Journal of Tissue Culture Methods*, 1994, vol. 16, pp. 87-94.
Gleiter, S., et anon., "Coupling of antibodies via protein Z on modified polyoma virus-like particles," *Protein Science*, 2001, vol. 10, pp. 434-444.
Gram, H., et al., "In vitro selection and affinity maturation of antibodies from a naïve combinatorial immunoglobulin library," *Proc. Natl. Acad. Sci. USA*, 1992, vol. 89, pp. 3576-3580.
Harlow, Ed, et anon., "Antibodies, A Laboratory Manual," Cold Spring Harbor Laboratory, 1988, pp. 1-8.
Henikoff, S., et anon., "Amino acid substitution matrices from protein blocks," *Proc. Natl. Acad. Sci. USA*, 1992, vol. 89, pp. 10915-10919.
Hiller, Y., et al., "Studies on the biotin-binding site of avidin," *Biochem. J.*, 1991, vol. 278, pp. 573-585.
Hober, S., et al., "Protein A chromatography for antibody purification," *Journal of Chromatography B*, 2007, vol. 848, pp. 40-47.
Hofmann, C., et al., "Efficient gene transfer into human hepatocytes by baculovirus vectors," *Proc. Natl. Acad. Sci. USA*, 1995, vol. 92, pp. 10099-10103.
Hoogenboom, Hennie, R., "Selecting and screening recombinant antibody libraries," *Nature Biotechnology*, 2005, vol. 23(9), pp. 1105-1116.
Horwitz, A., et al., "Secretion of functional antibody and Fab fragment from yeast cells," *Proc. Natl. Acad. Scu. USA*, 1988, vol. 85, pp. 8678-8682.
Huang, R., et al., "Chapter 13, Phage-Displayed Combinatorial Peptides," *Amino Acids, Peptides and Proteins in Organic Chemistry*, 2011, vol. 4—Protecion Reactions, Medicinal Chemistry, Combinatorial Synthesis, edited by Andrew B. Hughes.
Huang, S., et al., "Development of hybrid viral vectors for gene therapy," *Biotechnology Advances*, 2013, vol. 31, pp. 208-223.
Janssens, R., et al., "Generation of heavy-chain-only antibodies in mice," *PNAS*, 2006, vol. 103(41), pp. 15130-15135.
Jayapal, K., et al., "Recombinant Protein Therapeutics from CHO Cells—20 Years and Counting," *CHO Consortium—SBE Special Section*, 2007, pp. 1-8.

(56) References Cited

OTHER PUBLICATIONS

Jones, D., et al., "High-Level Expression of Recombinant IgG in the Human Cell Line PER.C6," *Biotechnol. Prog.*, 2003, vol. 19, pp. 163-168.

Kaymakcalan, Z., et al., "Comparisons of affinities, avidities, and complement activation of adalimumab, infliximab, and etanercept in binding to soluble and membrane tumor necrosis factor," *Clinical Immunology*, 2009, vol. 131, pp. 308-316.

Kim, D., et al., "Mutational approaches to improve the biophysical properties of human single-domain antibodies," *Biochimica et Biophysica Acta*, 2014, vol. 1844, pp. 1983-2001.

Kolmar, Harald, "Alternative binding proteins: Biological activity and therapeutic potential of cystine-knot miniproteins," *FEBS Journal*, 2008, vol. 275, pp. 2684-2690.

Kuby, Janis, "Capter 5, Immunoglobulins," *Immunology*, Second Edition, W.H. Freeman and Company, New York, 1994, pp. 109-134.

Lee, H., et anon., "Chapter 15—Expression in mammalian cells using BacMam viruses," *Expression Systems: Methods Express*, M.R. Dyson and Y. Durocher, eds, Sicon Publishing Limited, 2007, pp. 261-276.

Li, S., et al., "Single-chain antibodies against human insulin-like growth factor I receptor: expression, purification, and effect on tumor growth," *Cancer Immunol Immunother*, 2000, vol. 49, pp. 243-252.

MacDonald, L., et al., "Precise and in situe genetic humanization of 6 Mb of mouse immunoglobulin genes," *PNAS*, 2014, vol. 111(14), pp. 5147-5152.

MacKay, F., et al., "Mice Transgenic for BAFF Develop Lymphocytic Disorders Along with Autoimmune Manifestations," *J. Exp. Med.*, 1999, vol. 190(11), pp. 1697-1710.

Mah, C., et al., "Virus-Based Gene Delivey Systmes," *Clin Pharmacokinet*, 2002, vol. 41(12), pp. 901-911.

Massahi, A., et anon., "In-silico determination of *Pichia pastoris* signal peptides for extracellular recombinant protein production," *Journal of Theoretical Biology*, 2015, vol. 364, pp. 179-188.

Matthews, Brian W., "Hydrophoci Interactions in Proteins," *Encyclopedia of Life Sciences*, 2001, pp. 1-6.

Mattila, P., et al., "Fidelity of DNA Synthesis by the *Thermococcus litoralis* DNA polymerase—an extremely heat stable enzyme with proofreading activity," *Nucleic Acids Research*, 1991, vol. 19(18), pp. 4967-4973.

Mazutis, L., et al., "Single-cell analysis and sorting using droplet-based microfluidics," *Nat Protoc.*, 2013, vol. 8(5), pp. 870-891.

Mumberg, D., et al., "Yeast vectors for the controlled expression of heterologous proteins in different genetic backgrounds," *Gene*, 1995, vol. 156, pp. 119-122.

Muyldermans, Serge, "Single domain camel antibodies: current status," *Reviews in Molecular Biotechnology*, 2001, vol. 74, pp. 277-302.

Muyldermans, S., et al., "Camelid immunoglobulins and nanobody technology," *Veterinary Immunology and Immunopathology*, 2009, vol. 128, pp. 178-183.

Needleman, S., et anon., "A General Method Applicable to the Search for Similarities in the Amino Acid Sequence of Two Proteins," *J. Mol. Biol.*, 1970, vol. 48, pp. 443-453.

Nilsson, B., et al., "A synthetic IgG-binding domain based on staphylococcal protein A," *Protein Engineering*, 1987, vol. 1(2), pp. 107-113.

Nord, K., et al., "Binding proteins selected from combinatorial libraries of an 60 -helical bacterial receptor domain," *Nature Biotechnology*, 1997, vol. 15, pp. 772-777.

Ohno, K., et al., "Cell-Specific, Multidrug Delivery System Using Streptavidin-Protein A Fusion Protein," *Biochemical and Molecular Medicine*, 1996, vol. 58, pp. 227-233.

Orlandi, R., et al., "Cloning immunoglobulin variable domains for expression by the polymerase chain reaction," *Proc. Natl. Acad. Sci. USA*, 1989, vol. 86, pp. 3833-3827.

Ott, Terrence, "Chapter 10, Tissue Cluture of Fish Cell Lines," *NWFHS Laboratory Procedures Manual*, Second Edition, 2004, pp. 1-16.

Pearson, W., et anon., "Improved tools for biological sequence comparison," *Proc. Natl. Acad. Sci. USA*, 1988, vol. 85, pp. 2444-2448.

Pearson, William R., "Rapid and Sensitive Sequence Comparision with FASTP and FASTA," *Methods in Enzymology*, 1990, vol. 183, pp. 63-98.

Phelan, Mary C., "Basic Techniques in Mammalian Cell Tissue Culture," *Current Protocols in Cell Biology*, 2007, Unit 1.1, Supplement 36, pp. 1-18.

Rakestraw, J., et al., "Direction Evolution of a Secretary Leader for the Improved Expression of Heterologous Proteins and Full-Length Antibodiesin *Saccharomyces cerevisae*," *Biotechnology and Bioengineering*, 2009, vol. 103 (6), pp. 1192-1201.

Rakestraw, J., et al., "Secretion-and-capture cell-surface display for selection of target-binding proteins," *Protein Engineering, Design & Selection*, 2011, vol. 24(6), pp. 525-530.

Saggy, I., et al., "Antibody isolation from immunized animals: comparision of phase display and antibody discovery via V gene repertoire mining," *Protein Engineering, Design & Selection*, 2012, vol. 25(10), pp. 539-549.

Sano, T., et anon., "A Sreptavidin-Protein A Chimera that Allows One-Step Production of a Variety of Specific Antibody Conjugates," *Bio/technology*, 1991, vol. 9, pp. 1378-1381.

Sato, N., et al., "Long anchor using Flo1 protein enhances reactivity of cell surface-displayed glucoamylase to polymer substrates," *Appl Microbiol Biotechnol*, 2002, vol. 60, pp. 469-474.

Schoonbroodt, S., et al., "Oligonucleotide-assisted cleavage and ligation: a novel directional DNA cloning technology to capture cDNAs. Application in the construction of human immune antibody phage-display library," *Nucleuc Acids Research*, 2005, vol. 33(9), pp. 1-14.

Schreuder, M., et al., "Immobilizing proteins on the surface of yeast cells," *TIBTECH*, 1996, vol. 14, pp. 115-120.

Sellers, Peter H., "On the Theory and Computation of Evolutionary Distances," *SIAM J. Appl. Math.*, 1974, vol. 26(4), pp. 787-793.

Sergeeva, A., et al., "Display technologies: application for the discovery of drug and gene delivery agents," *Adv Drug Deliv Rev.*, 2006, vol. 58(15), pp. 1622-1654.

Shaw, D., et al., "Characterization of a mouse/human chimeric monoclonal antibody (17-1A) to a colon cancer tumor-associated antigen," *The Journal of Immunology*, 1987, vol. 138, pp. 4534-4538.

Shusta, E., et al., "Increasing the secretory capacity of *Saccharomyces cerevisiae* for production of single-chain antibody fragments," *Nature Biotechnology*, 1998, vol. 16, pp. 773-777.

Sun L., et al., "Chimeric antibody with human constant regions and mouse variable regions directed against carcinoma-associated antigen 17-1A," *Proc. Natl. Acad. Sci. USA*, 1987, vol. 84, pp. 214-218.

Traxlmayr, M., et al., "Directed evolution of Her2/neu-binding IgGI-Fc for improved stabilty and resistance to aggregation by yeast surface display," *Protein Engineering, Desiogn & Selection*, 2013, vol. 26(4), pp. 255-265.

Ueda, M., et anon., "Genetic immobilization of proteins on the yeast cell surface," *Biotechnology Advances*, 2000, vol. 18, pp. 121-140.

Van Den Beucken, T., et al., "Affinity maturation of Fab antibody fragments by fluorescent-activated cell sorting of yeast-displayed libraries," *FEBS Letters*, 2003, vol. 546, pp. 288-294.

Van Der Vaart, J., et al., "Comparison of cell wall protein of *Saccharomyces cerevisiae* as anchors for cell surface expression of heterologous proteins," *Appl. Environ. Microbiol.*, 1997, vol. 63(2), pp. 615-620.

Vanhoefer, U., et al., "Phase I Study of the Humanized Antiepidermal Growth Factor Receptor Monoclonal Antibody EMD72000 in Patients With Advanced Solid Tumors That Express the Epidermal Growth Factor Receptor," *Journal of Clinical Oncology*, 2004, vol. 22(1), pp. 175-184.

Waldmann, Thomas A., "Monoclonal Antibodies in Diagnosis and Therapy," *Science*, 1991, vol. 252, pp. 1657-1662.

(56) References Cited

OTHER PUBLICATIONS

Wang, Z., et al., "A new yeast display vector permitting free scFv amino termini can augment ligand binding affinities," *Protein Engineering, Design & Selection*, 2005, vol. 18(7), pp. 337-343.

Ward, E. Sally, "Antibody engineering: the use of *Escherichia coli* as an expression host," *The FASEB Journal*, 1992, vol. 6, pp. 2422-2427.

Weaver-Feldhaus, J., et al., "Yeast mating for combinatorial Fab library generation and surface display," *FEBS Letters*, 2004, vol. 564, pp. 24-34.

Weller, Horst, "Collodial Semiconductor Z-Particles: Chemistry in the Transition Region Between Solid State and Molecules," *Angew. Chem. Int. Ed. Engl.*, 1993, vol. 32, pp. 41-53.

Wozniak-Knopp, G., et al., "Introducing antigen-binding sites in structural loops of immunolglobulin constant domains: Fc fragments with engineered HER2/neu-binding sites and antibody properties," *Protein Engineering, Design & Selection*, 2010, vol. 23(4), pp. 289-297.

Wysocki, L., et anon., "'Panning' for lymphocytes: A method for cell selection," *Proc. Natl. Acad. Sci. USA*, 1978, vol. 75(6), pp. 2844-2848.

Rhiel, L., et al., "REAL-Select: Full-Length Antibody Display and Library Screening by Surface Capture on Yeast Cells," *PLOS ONE*, 2014, vol. 9(12), pp. 1-19.

Lane 1: Marker
Lane 2: DI-17E6 reference sample (EMD52579)
Lane 3: Streptavidin (Calbiochem 189730)
Lane 4: Chimera SA-ZZ purified (P2859UN)

Gel: Tris-Acetate 3-8%

ZZ-SA binding to Fc of hIgG1

015-11-001
Tips: AHC
Loading: DI-17E6 (5 mcg/ml)
Association:
▬ SA-ZZ 500nM
▬ SA-ZZ 50nM ZZ-SA binding to binding of biotinylated HRP 015-11-003
Tips: StreptAvidin
Loading: Biotinylated HRP (50 mcg/ml)
Association:
▬ SA-ZZ 1000nM
▬ SA-ZZ 100nM
▬ SA-ZZ 10nM
▬ Unspecific binding of SA-ZZ 1000nM

A

B

Yeast display selected
$K_D$ 56 pM

Parental antibody
$K_D$ 322 pM

| | Yeast display selected | | | Parental antibody | |
|---|---|---|---|---|---|
| ka: | 2.623e+6 | M-1s-1 | ka: | 1.939e+6 | M-1s-1 |
| kd: | 1.484e-4 | s-1 | kd: | 6.248e-4 | s-1 |
| KD: | 5.657e-11 | M | KD: | 3.222e-10 | M |
| Avg(Rmax_1): | 27.6 | RU | Avg(Rmax_1): | 29.4 | RU |
| Chi2: | 0.2609 | RU2 | Chi2: | 0.142 | RU2 |

SEQUENCE LISTING

<160> NUMBER OF SEQ ID NOS: 30

<210> SEQ ID NO 1
<211> LENGTH: 118
<212> TYPE: PRT
<213> ORGANISM: Artificial Sequence
<220> FEATURE:
<223> OTHER INFORMATION: ZZ domain

<400> SEQUENCE: 1

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile
                20                  25                  30

Gln Ser Leu Lys Asp Asp Pro Ser Gln Ser Ala Asn Leu Leu Ala Glu
            35                  40                  45

Ala Lys Lys Leu Asn Asp Ala Gln Ala Pro Lys Met Val Asp Asn Lys
        50                  55                  60

Phe Asn Lys Glu Gln Gln Asn Ala Phe Tyr Glu Ile Leu His Leu Pro
65                  70                  75                  80

Asn Leu Asn Glu Glu Gln Arg Asn Ala Phe Ile Gln Ser Leu Lys Asp
                85                  90                  95

Asp Pro Ser Gln Ser Ala Asn Leu Leu Ala Glu Ala Lys Lys Leu Asn
            100                 105                 110

Asp Ala Gln Ala Pro Lys
        115

<210> SEQ ID NO 2
<211> LENGTH: 157
<212> TYPE: PRT
<213> ORGANISM: Artificial Sequence
<220> FEATURE:
<223> OTHER INFORMATION: SA domain

<400> SEQUENCE: 2

```
Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val
145                 150                 155
```

<210> SEQ ID NO 3
<211> LENGTH: 292
<212> TYPE: PRT
<213> ORGANISM: Artificial Sequence
<220> FEATURE:
<223> OTHER INFORMATION: SA-ZZ fusion protein

<400> SEQUENCE: 3

```
Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln Gly
145                 150                 155                 160

Gly Gly Gly Ser Gly Gly Gly Ser Gly Gly Gly Ser Met Val
            165                 170                 175

Asp Asn Lys Phe Asn Lys Glu Gln Gln Asn Ala Phe Tyr Glu Ile Leu
            180                 185                 190
```

```
His Leu Pro Asn Leu Asn Glu Glu Gln Arg Asn Ala Phe Ile Gln Ser
            195                 200                 205

Leu Lys Asp Asp Pro Ser Gln Ser Ala Asn Leu Leu Ala Glu Ala Lys
        210                 215                 220

Lys Leu Asn Asp Ala Gln Ala Pro Lys Met Val Asp Asn Lys Phe Asn
225                 230                 235                 240

Lys Glu Gln Gln Asn Ala Phe Tyr Glu Ile Leu His Leu Pro Asn Leu
                245                 250                 255

Asn Glu Glu Gln Arg Asn Ala Phe Ile Gln Ser Leu Lys Asp Asp Pro
            260                 265                 270

Ser Gln Ser Ala Asn Leu Leu Ala Glu Ala Lys Lys Leu Asn Asp Ala
        275                 280                 285

Gln Ala Pro Lys
    290

<210> SEQ ID NO 4
<211> LENGTH: 26
<212> TYPE: PRT
<213> ORGANISM: Artificial Sequence
<220> FEATURE:
<223> OTHER INFORMATION: hGH signal peptide

<400> SEQUENCE: 4

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 5
<211> LENGTH: 954
<212> TYPE: DNA
<213> ORGANISM: Artificial Sequence
<220> FEATURE:
<223> OTHER INFORMATION: nucleotiode sequence of second label

<400> SEQUENCE: 5
atggccaccg gcagcaggac cagcctgctg ctggccttcg gcctgctgtg cctgccctgg      60
ctgcaggagg gcagcgccga ccccagcaag gacagcaagg cccaggtgag cgccgccgag     120
gccggcatca ccggcacctg gtacaaccag ctgggcagca ccttcatcgt gaccgccggc     180
gccgacggcg ccctgaccgg cacctacgag agcgccgtgg gcaacgccga gagcaggtac     240
gtgctgaccg gcaggtacga cagcgccccc gccaccgacg gcagcggcac cgccctgggc     300
tggaccgtgg cctggaagaa caactacagg aacgcccaca cgccaccac ctggagcggc      360 cagtacgtgg gcgcgccga ggccaggatc aacacccagt ggctgctgac cagcggcacc      420
accgaggcca acgcctggaa gagcaccctg gtgggccacg acaccttcac caaggtgaag     480
cccagcgccg ccagcatcga cgccgccaag aaggccggcg tgaacaacgg caaccccctg     540
gacgccgtgc agcagggcgg cggcggcagc ggcggcggcg cagcggcgg cggcggcagc      600 atggtggaca caagttcaa caaggagcag cagaacgcct tctacgagat cctgcacctg      660
cccaacctga cgaggagca gaggaacgcc ttcatccaga gcctgaagga cgacccagc       720 cagagcgcca acctgctggc cgaggccaag aagctgaacg acgcccaggc ccccaagatg     780
gtggacaaca agttcaacaa ggagcagcag aacgccttct acgagatcct gcacctgccc     840
aacctgaacg aggagcagag gaacgccttc atccagagcc tgaaggacga ccccagccag    900
agcgccaacc tgctggccga ggccaagaag ctgaacgacg cccaggcccc caag          954
```

<210> SEQ ID NO 6
<211> LENGTH: 318
<212> TYPE: PRT
<213> ORGANISM: Artificial Sequence
<220> FEATURE:
<223> OTHER INFORMATION: amino acid sequence of second label

<400> SEQUENCE: 6

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Pro Ser Lys Asp Ser
            20                  25                  30

Lys Ala Gln Val Ser Ala Ala Glu Ala Gly Ile Thr Gly Thr Trp Tyr
        35                  40                  45

Asn Gln Leu Gly Ser Thr Phe Ile Val Thr Ala Gly Ala Asp Gly Ala
    50                  55                  60

Leu Thr Gly Thr Tyr Glu Ser Ala Val Gly Asn Ala Glu Ser Arg Tyr
65                  70                  75                  80

Val Leu Thr Gly Arg Tyr Asp Ser Ala Pro Ala Thr Asp Gly Ser Gly
                85                  90                  95

Thr Ala Leu Gly Trp Thr Val Ala Trp Lys Asn Asn Tyr Arg Asn Ala
            100                 105                 110

His Ser Ala Thr Thr Trp Ser Gly Gln Tyr Val Gly Gly Ala Glu Ala
        115                 120                 125

Arg Ile Asn Thr Gln Trp Leu Leu Thr Ser Gly Thr Thr Glu Ala Asn
    130                 135                 140

Ala Trp Lys Ser Thr Leu Val Gly His Asp Thr Phe Thr Lys Val Lys
145                 150                 155                 160

Pro Ser Ala Ala Ser Ile Asp Ala Ala Lys Lys Ala Gly Val Asn Asn
                165                 170                 175

Gly Asn Pro Leu Asp Ala Val Gln Gln Gly Gly Gly Ser Gly Gly
            180                 185                 190

Gly Gly Ser Gly Gly Gly Gly Ser Met Val Asp Asn Lys Phe Asn Lys
        195                 200                 205

Glu Gln Gln Asn Ala Phe Tyr Glu Ile Leu His Leu Pro Asn Leu Asn
    210                 215                 220

Glu Glu Gln Arg Asn Ala Phe Ile Gln Ser Leu Lys Asp Asp Pro Ser
225                 230                 235                 240

Gln Ser Ala Asn Leu Leu Ala Glu Ala Lys Lys Leu Asn Asp Ala Gln
                245                 250                 255

Ala Pro Lys Met Val Asp Asn Lys Phe Asn Lys Glu Gln Gln Asn Ala
            260                 265                 270

Phe Tyr Glu Ile Leu His Leu Pro Asn Leu Asn Glu Glu Gln Arg Asn
    275                 280                 285

Ala Phe Ile Gln Ser Leu Lys Asp Asp Pro Ser Gln Ser Ala Asn Leu
            290                 295                 300

Leu Ala Glu Ala Lys Lys Leu Asn Asp Ala Gln Ala Pro Lys
305                 310                 315
```

<210> SEQ ID NO 7
<211> LENGTH: 72
<212> TYPE: DNA
<213> ORGANISM: Artificial Sequence
<220> FEATURE:
<223> OTHER INFORMATION: primer

```
<400> SEQUENCE: 7
ctattgccag cattgctgct aaagaagaag gggtacaact cgataaaaga gaagtgcagc    60
tggtgcagtc tg                                                        72

<210> SEQ ID NO 8
<211> LENGTH: 70
<212> TYPE: DNA
<213> ORGANISM: Artificial Sequence
<220> FEATURE:
<223> OTHER INFORMATION: primer

<400> SEQUENCE: 8
ctcttggagg agggtgccag ggggaagacc gatgggccct tggtggaggc tgaggagacg    60
gtgaccaggg                                                           70

<210> SEQ ID NO 9
<211> LENGTH: 19
<212> TYPE: PRT
<213> ORGANISM: Artificial Sequence
<220> FEATURE:
<223> OTHER INFORMATION: artificial leader sequence

<400> SEQUENCE: 9

Met Glu Leu Gly Leu Ser Trp Ile Phe Leu Leu Ala Ile Leu Lys Gly
1               5                   10                  15

Val Gln Cys

<210> SEQ ID NO 10
<211> LENGTH: 19
<212> TYPE: PRT
<213> ORGANISM: Artificial Sequence
<220> FEATURE:
<223> OTHER INFORMATION: artificial leader sequence

<400> SEQUENCE: 10

Met Glu Leu Gly Leu Arg Trp Val Phe Leu Val Ala Ile Leu Glu Gly
1               5                   10                  15

Val Gln Cys

<210> SEQ ID NO 11
<211> LENGTH: 19
<212> TYPE: PRT
<213> ORGANISM: Artificial Sequence
<220> FEATURE:
<223> OTHER INFORMATION: artificial leader sequence

<400> SEQUENCE: 11

Met Lys His Leu Trp Phe Phe Leu Leu Leu Val Ala Ala Pro Arg Trp
1               5                   10                  15

Val Leu Ser

<210> SEQ ID NO 12
<211> LENGTH: 19
<212> TYPE: PRT
<213> ORGANISM: Artificial Sequence
<220> FEATURE:
<223> OTHER INFORMATION: artificial leader sequence

<400> SEQUENCE: 12

Met Asp Trp Thr Trp Arg Ile Leu Phe Leu Val Ala Ala Ala Thr Gly
1               5                   10                  15

Ala His Ser
```

```
<210> SEQ ID NO 13
<211> LENGTH: 18
<212> TYPE: PRT
<213> ORGANISM: Artificial Sequence
<220> FEATURE:
<223> OTHER INFORMATION: artificial leader sequence

<400> SEQUENCE: 13

Met Asp Trp Thr Trp Arg Phe Leu Phe Trp Ala Ala Ala Thr Gly Val
1               5                   10                  15

Gln Ser

<210> SEQ ID NO 14
<211> LENGTH: 19
<212> TYPE: PRT
<213> ORGANISM: Artificial Sequence
<220> FEATURE:
<223> OTHER INFORMATION: artificial leader sequence

<400> SEQUENCE: 14

Met Glu Phe Gly Leu Ser Trp Leu Phe Leu Val Ala Ile Leu Lys Gly
1               5                   10                  15

Val Gln Cys

<210> SEQ ID NO 15
<211> LENGTH: 19
<212> TYPE: PRT
<213> ORGANISM: Artificial Sequence
<220> FEATURE:
<223> OTHER INFORMATION: artificial leader sequence

<400> SEQUENCE: 15

Met Glu Phe Gly Leu Ser Trp Val Phe Leu Val Ala Leu Phe Arg Gly
1               5                   10                  15

Val Gln Cys

<210> SEQ ID NO 16
<211> LENGTH: 26
<212> TYPE: PRT
<213> ORGANISM: Artificial Sequence
<220> FEATURE:
<223> OTHER INFORMATION: artificial leader sequence

<400> SEQUENCE: 16

Met Asp Leu Leu His Lys Asn Met Lys His Leu Trp Phe Phe Leu Leu
1               5                   10                  15

Leu Val Ala Ala Pro Arg Trp Val Leu Ser
            20                  25

<210> SEQ ID NO 17
<211> LENGTH: 22
<212> TYPE: PRT
<213> ORGANISM: Artificial Sequence
<220> FEATURE:
<223> OTHER INFORMATION: artificial leader sequence

<400> SEQUENCE: 17

Met Asp Met Arg Val Pro Ala Gln Leu Leu Gly Leu Leu Leu Leu Trp
1               5                   10                  15

Leu Ser Gly Ala Arg Cys
            20
```

```
<210> SEQ ID NO 18
<211> LENGTH: 22
<212> TYPE: PRT
<213> ORGANISM: Artificial Sequence
<220> FEATURE:
<223> OTHER INFORMATION: artificial leader sequence

<400> SEQUENCE: 18

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 19
<211> LENGTH: 16
<212> TYPE: PRT
<213> ORGANISM: Artificial Sequence
<220> FEATURE:
<223> OTHER INFORMATION: artificial leader sequence

<400> SEQUENCE: 19

Met Pro Leu Leu Leu Leu Leu Pro Leu Leu Trp Ala Gly Ala Leu Ala
1               5                   10                  15

<210> SEQ ID NO 20
<211> LENGTH: 25
<212> TYPE: PRT
<213> ORGANISM: Artificial Sequence
<220> FEATURE:
<223> OTHER INFORMATION: synthetic sequence
<220> FEATURE:
<221> NAME/KEY: SITE
<222> LOCATION: 19..19
<223> OTHER INFORMATION: Xaa can be any naturally occurring amino acid

<400> SEQUENCE: 20

Met Lys Trp Val Thr Phe Ile Ser Leu Leu Phe Leu Phe Ser Ser Ala
1               5                   10                  15

Tyr Ser Xaa Arg Gly Val Phe Arg Arg
            20                  25

<210> SEQ ID NO 21
<211> LENGTH: 18
<212> TYPE: PRT
<213> ORGANISM: Artificial Sequence
<220> FEATURE:
<223> OTHER INFORMATION: artificial leader sequence

<400> SEQUENCE: 21

Met Gln Val Lys Ser Ile Val Asn Leu Leu Leu Ala Cys Ser Leu Ala
1               5                   10                  15

Val Ala

<210> SEQ ID NO 22
<211> LENGTH: 22
<212> TYPE: PRT
<213> ORGANISM: Artificial Sequence
<220> FEATURE:
<223> OTHER INFORMATION: artificial leader sequence

<400> SEQUENCE: 22

Met Gln Phe Asn Trp Asn Ile Lys Thr Val Ala Ser Ile Leu Ser Ala
1               5                   10                  15

Leu Thr Leu Ala Gln Ala
            20
```

-continued

```
<210> SEQ ID NO 23
<211> LENGTH: 21
<212> TYPE: PRT
<213> ORGANISM: Artificial Sequence
<220> FEATURE:
<223> OTHER INFORMATION: artificial leader sequence

<400> SEQUENCE: 23

Met Gln Phe Asn Ser Val Val Ile Ser Gln Leu Leu Leu Thr Leu Ala
1               5                   10                  15

Ser Val Ser Met Gly
            20

<210> SEQ ID NO 24
<211> LENGTH: 23
<212> TYPE: PRT
<213> ORGANISM: Artificial Sequence
<220> FEATURE:
<223> OTHER INFORMATION: artificial leader sequence

<400> SEQUENCE: 24

Met Arg Phe Ser Thr Thr Leu Ala Thr Ala Ala Thr Ala Leu Phe Phe
1               5                   10                  15

Thr Ala Ser Gln Val Ser Ala
            20

<210> SEQ ID NO 25
<211> LENGTH: 36
<212> TYPE: PRT
<213> ORGANISM: Artificial Sequence
<220> FEATURE:
<223> OTHER INFORMATION: artificial leader sequence

<400> SEQUENCE: 25

Met Glu Ser Val Ser Ser Leu Phe Asn Ile Phe Ser Thr Ile Met Val
1               5                   10                  15

Asn Tyr Lys Ser Leu Val Leu Ala Leu Leu Ser Val Ser Asn Leu Lys
            20                  25                  30

Tyr Ala Arg Gly
        35

<210> SEQ ID NO 26
<211> LENGTH: 19
<212> TYPE: PRT
<213> ORGANISM: Artificial Sequence
<220> FEATURE:
<223> OTHER INFORMATION: artificial leader sequence

<400> SEQUENCE: 26

Met Arg Phe Pro Ser Ile Phe Thr Ala Val Leu Phe Ala Ala Ser Ser
1               5                   10                  15

Ala Leu Ala

<210> SEQ ID NO 27
<211> LENGTH: 17
<212> TYPE: PRT
<213> ORGANISM: Artificial Sequence
<220> FEATURE:
<223> OTHER INFORMATION: artificial leader sequence

<400> SEQUENCE: 27

Met Phe Lys Ser Val Val Tyr Ser Ile Leu Ala Ala Ser Leu Ala Asn
1               5                   10                  15

Ala
```

```
<210> SEQ ID NO 28
<211> LENGTH: 21
<212> TYPE: PRT
<213> ORGANISM: Artificial Sequence
<220> FEATURE:
<223> OTHER INFORMATION: artificial leader sequence

<400> SEQUENCE: 28

Met Lys Phe Leu Val Asn Val Ala Leu Val Phe Met Val Val Tyr Ile
1               5                   10                  15

Ser Tyr Ile Tyr Ala
            20

<210> SEQ ID NO 29
<211> LENGTH: 72
<212> TYPE: DNA
<213> ORGANISM: Artificial Sequence
<220> FEATURE:
<223> OTHER INFORMATION: Up-Primer for CDR-H3 library generation

<400> SEQUENCE: 29
ctattgccag cattgctgct aaagaagaag gggtacaact cgataaaaga gaagtgcagc      60
tggtgcagtc tg                                                          72

<210> SEQ ID NO 30
<211> LENGTH: 70
<212> TYPE: DNA
<213> ORGANISM: Artificial Sequence
<220> FEATURE:
<223> OTHER INFORMATION: Low-Primer for CDR-H3 library generation

<400> SEQUENCE: 30
ctcttggagg agggtgccag ggggaagacc gatgggccct tggtggaggc tgaggagacg      60
gtgaccaggg                                                             70
```

METHODS FOR NON-COVALENT FC-DOMAIN-CONTAINING PROTEIN DISPLAY ON THE SURFACE OF CELLS AND METHODS OF SCREENING THEREOF

CROSS-REFERENCE TO RELATED APPLICATIONS

This application is a national stage filing under 35 U.S.C. 371 of PCT/EP2015/002125 filed Oct. 27, 2015, which International Application was published by the International Bureau in English on May 6, 2016, and application claims priority from European Application No. 14003649.2, filed Oct. 28, 2014, which applications are hereby incorporated in their entirety by reference in this application.

FIELD OF THE INVENTION

The present invention concerns the display of proteins such as monoclonal antibodies on the surface of host cells and methods for screening thereof. In particular, the present invention concerns the screening of antibodies or antibody libraries or Fc-domain-containing fusion proteins displayed on the surface of host cells and methods for identifying and selecting Fc-domain-containing proteins of desired phenotype. The inventive methods are particularly useful for screening immunoglobulin libraries in eukaryotic host cells that express an immunoglobulin or fragments thereof.

BACKGROUND OF THE INVENTION

In academia and pharmaceutical industry great resources are spent on discovery and development of monoclonal antibodies for target-based therapies. Among the available technologies developed thus far, high-throughput techniques for screening antibody libraries have enabled the identification of new candidate molecules and the fast optimization of pre-selected binders by affinity maturation.

As the identification of new candidate molecules is to a great extend technology driven, the invention of new powerful screening technologies has proven to be one critical part in an overall strategy to further accelerate the process of antibody discovery and development. Several in vitro display technologies have emerged since the advent of phage display technologies in the mid-eighties and its application for antibody display. Next to phage display, there are four main display technologies referred to cell display, ribosomal display, mRNA display and DNA display, with phage display being the most established one.

Phage display is currently the most widespread method for the display and selection of large collections of antibodies and for the further engineering of selected antibodies. Antibodies are usually displayed in what is known as the 'monovalent' format, in which the antibody-coat protein fusion gene is carried on a phagemid vector and display is performed by infecting the phagemid-carrying bacteria with a helper phage. This format, also known as the 3×3 format, is mostly preferred because constructing libraries in phagemid vectors offer higher transformation efficiency of phagemid vectors compared with phage vectors, as it provides for the selection of the highest affinity binders, which are not skewed by avidity effects (Saggy et al. (2012) Protein Eng. Des. Sel. 25, 539-549).

The most successful applications of phage antibody display include for example de novo isolation of high-affinity human antibodies from non-immune and synthetic libraries, including antibodies against self-antigens, the generation of high affinity antibodies with picomolar affinity by in vitro affinity maturation and the discovery of antibodies with unique properties from non-immune and immune libraries from animal or human donors (Hogenboom (2005) Nat. Biotech 23, 1105-1116).

Despite the advantages of phage antibody display this technology also has disadvantages which limit its use: In *E. coli* efficient secretion of functional antibody fragments into the periplasmic space typically requires co-expression of chaperones and isomerases to prevent misfolding and aggregation of antibody fragments due to the limited secretion capacity (Bothmann and Plückthun (2000), J. Biol. Chem. Vol. 275 (22), 17100-17105). In addition, there appears to be a biological selection against odd numbers of cysteines, runs of positive charges, and certain residues at fixed positions within the displayed peptide which consequently results in an inherently biased selection of antibody fragments.

The second most frequently used technology is yeast display, which is a robust technology to select and engineer antibody-fragments from combinatorial libraries. Yeast display technologies are advantageous for the expression of oligomeric molecules, such as e.g. full-length IgG immunoglobulins, as the antibodies have to pass the eukaryotic secretion pathway compared to bacterially expressed antibodies, which results in an overall larger number of correctly folded immunoglobulins.

Yeast display utilizes the presence of several naturally occurring cell wall anchored proteins, which can be used to target heterologous proteins to the outermost cell surface via attachment of a C-terminal glycosylphosphatidylinositol attachment signal, commonly referred to as GPI anchor. Initially, yeast display relied on the genetic fusion of antibody-coding DNA sequences in-frame with the sequence of a yeast cell wall mannoprotein (Doerner et al. (2014), FEBS Letters 588, 278-287). The protein repertoire, which is used for surface display was expanded and now includes for example a-agglutinin, Flo1p and α-agglutinin. Of those, the a-agglutinin employing system is the most frequently used.

A-agglutinin is one of the two mating type specific agglutinins that mediate cell-cell contact during mating of appropriate yeast cells. It is formed by one core-subunit Aga1p, which is linked to a smaller binding-subunit Aga2p through two disulfide bridges. Due to the GPI-attachment-signal of Aga1p the core-subunit covalently anchors the Aga complex to the cell wall. The modular structure of a-agglutinin furthermore enables the fusion of the heterologous protein to be displayed to the C- or N-terminus of Aga2p compared to single-unit GPI-anchored proteins that only allow N-terminal fusion of heterologous proteins, due to the required C-terminal GPI-attachment signal. Flo1p-based systems differ in that they can attach and immobilize heterologous proteins non-covalently via fusion to the N-terminal flocculation functional domain that is believed to bind to carbohydrate units on the cell-surface.

The overexpression of chromosomally encoded AGA1 and the episomally encoded AGA2-fusion proteins is typically driven by the inducible Gal10-promoter, which accounts for stoichiometric expression levels of both subunits which associate in the endoplasmatic reticulum. Galactose-induced expression results in the display of approximately $10^4$-$10^5$ copies of the fusion-protein on the surface of a host cell (Doerner et al. (2014), FEBS Letters 588, 278-287, Boder and Witrup (1997) Nat. Biotechnol. 15, 553-557). Detection of surface-exposed fusion proteins occurs by virtue of epitope tags or by means of its activity, which in case of an antibody is its binding-affinity to a soluble antigen. The detection is typically carried out with the respective biotinylated antigen and a secondary reagent such as streptavidin-conjugated fluorophores, or an otherwise labelled antigen.

In one approach yeast display was modified which is known as secretion-and-capture cell-surface display for selection of target-binding proteins (SECANT™, Rakestraw et al. (2011) Protein Eng Des Sel. June; 24(6):525-30). This technology was successfully used to display full-length immunoglobulin G (IgG) antibodies on the surface of yeast cells. In the SECANT™ technology the protein of interest (POI) is genetically fused to the small biotin acceptor peptide (BAP) followed by a TEV protease cleavage site to facilitate purification. The TEV-BAP peptide may be fused to the N- or C-terminus of the POI. On the end of the POI opposite to the TEV-BAP tag, the POI is genetically fused to a tag, which is typically a FLAG-tag, whereby the entire BAP, POI and FLAG-tag gene is located 3' to a yeast secretory signal, typically the engineered aMFpp8 leader sequence, invertase leader sequence, or a synthetic leader sequence, which is followed by Kex2 proteotlytic cleavage site (Rakestraw et al. (2011) Protein Eng Des Sel. June; 24(6):525-30). For the selection of a POI, the gene of the POI is expressed as an N- or C-terminal fusion to a BAP, which is co-expressed with BirA biotin ligase and chaperones. The BirA biotin ligase biotinylates the BAP tag on the POI. Upon secretion, the POI is then bound by surface-localized avidin and can be labeled with a fluorophore-tagged anti-epitope antibodies or fluorophore-tagged antigen for subsequent detection and selection.

While the SECANT technology allows the secretion and selection of complex molecules such as IgG immunoglobulins, this technology still requires the genetic modification of a POI and co-expression of a biotin ligase, which adds additional steps in the screening and selecting procedure.

The continued demand for yeast display and in particular for the display of complex molecules and its use in antibody identification and maturation, there is also a continued requirement to reduce the costs and time associated with the screening procedure to identify new antibody candidates.

It is thus an objective of the present invention to provide a method which allows display of complex molecules on the surface of host cells for identification of a protein of interest, without the requirement for genetically encoded anchor proteins or intracellular antibody modification.

SUMMARY OF THE INVENTION

The present inventors have surprisingly found a method for displaying, detecting and selecting proteins of interest of desired phenotype on the surface of host cells, whereby the inventive method does not require genetic modification of the protein of interest.

In a first embodiment, the present invention provides for a method for protein display on the surface of a host cell, whereby the method comprises the following steps:
(a) Introducing into a host cell at least one or more polynucleotides which encode a protein of interest to be displayed on the surface of said host cell;
(b) Contacting the surface of said host cell with a first label;
(c) Contacting the surface of said host cell of (b) with a second label, whereby the second label specifically and non-covalently binds to said first label and to said protein of interest encoded by said at least one or more polynucleotides;
(d) Expressing said at least one or more polynucleotides in said host cell under conditions sufficient for secretion of said protein of interest encoded by the at least one or more polynucleotides;
(e) Contacting said host cells of step (d) with means for specifically detecting said protein of interest bound non-covalently by said second label and detecting host cells which display the protein of interest on their surface.

According to one embodiment of the invention the protein encoded by the at least one or more polynucleotides is a monomer or a multimer.

According to one embodiment of the invention the protein encoded by the at least one or more polynucleotides comprises a signal peptide.

In another embodiment, the first label used in the inventive method is covalently bound to the surface of the host cell.

According to one embodiment, the first label used in the inventive method is biotin or a biotin-derivative.

In another embodiment, the second label used in the inventive method is a further protein or further polypeptide.

In one embodiment, the further protein or further peptide which is the second label of the inventive method is a multimeric protein.

In one embodiment, the second label of the inventive method is or comprises one of protein A, protein L, protein G, protein A-G fusion, domains E, D, A, B of protein A, fused to avidin, strepavidin, or sequence variants thereof.

According to one embodiment, the host cell of the inventive method is selected from mammalian, yeast or insect cells as disclosed herein.

In one embodiment, the means for specifically detecting said protein of interest in the inventive method are selected from the group comprising antibodies or antibody fragments, quantum dots, enzymes, fluorophores, or intercalating dyes, and gangliosides.

In one embodiment, the means for specifically detecting said protein of interest in the inventive method may be one of a polyclonal antibody, monoclonal antibody, scFv-Fc, scFv, (Fab')$_2$, Fab, minibody, diabody, or VHH antibody; all of which may optionally be coupled to a further label.

In one embodiment, the inventive method as disclosed above further comprises the step of selecting the host cells, e.g. the cells detected in step (d) of the inventive method.

According to one embodiment, the host cells selected in the inventive method as disclosed above display a protein of interest of altered phenotype.

According to one embodiment, the altered phenotype of the protein of interest according to the invention is one of surface expression level, protein stability, protein folding, or affinity.

In one embodiment, the altered phenotype of the protein of interest in the inventive method is determined by comparing said host cells of step (e) of the inventive method to a reference sample.

In one embodiment, the protein encoded by the at least one or more polynucleotides of step (a) of the inventive method comprises at least one Fc-domain as disclosed herein.

In a preferred embodiment, the at least one Fc-domain according to the invention as disclosed above is one of human IgG1, human IgG2, murine IgG2a, murine IgG2b, or murine IgG3; or, sequence variants thereof.

In a preferred embodiment, the Fc-domain-containing protein according to the invention is an N-terminal Fc-domain fusion protein, C-terminal Fc-domain fusion protein or an antibody.

In a preferred embodiment, the antibody encoded by the polynucleotides of step (a) of the inventive method is a monoclonal antibody, preferably the monoclonal antibody is a murine monoclonal antibody, mouse-human chimeric monoclonal antibody, humanized monoclonal antibody, or human monoclonal antibody.

According to one embodiment, the second label of the inventive method specifically binds Fc domains of human IgG1, human IgG2, murine IgG2a, murine IgG2b, or murine IgG3.

According to one embodiment, the affinity of the second label of the inventive method for antibody binding is at least $K_d=10^{-8}$, $2.5\times10^{-8}$, $5\times10^{-8}$, $7.5\times10^{-8}$, $10^{-9}$, or $5\times10^{-8}$ M.

In one embodiment, the second label of the inventive method as disclosed above comprises the amino acid sequence according to SEQ ID NO: 1 and/or the amino acid sequence according to SEQ ID NO 2.

In one embodiment, the second label of the inventive method comprises the amino acid sequence of SEQ ID NO: 3.

In a preferred embodiment, step (e) of the inventive method as disclosed above further comprises:
(i) contacting said host cell with a detectably labeled antibody or antibody fragment, which specifically binds to Fc domains of human IgG1, human IgG2, murine IgG2a, murine IgG2b, or murine IgG3; or sequence variants thereof
(ii) contacting the host cell with an antigen and/or epitope of the antibody bound to the second label, which is coupled to a further detectable label distinct from the label used in (i);
(iii) detecting the labels of (i) and/or (ii) on said host cells.
(iv) selecting host cells that display altered amounts of the label used in (i), and/or the label used in (ii) and/or display altered amounts of both labels compared to a reference sample.

In a preferred embodiment the detectably labeled antibody or antibody fragment of step (e) (i) according to the invention specifically binds to kappa or lambda light chains of human or murine IgG1, human IgG2, murine IgG2a, murine IgG2b, or murine IgG3; or sequence variants thereof.

In a preferred embodiment, the labels of (i) and (ii) and/or the selection step (iv) of the inventive method comprise flow cytometry and/or FACS and/or microfluidics.

According to one embodiment, steps (a)-(e) of the inventive method as disclosed herein may be reiterated.

In one embodiment, the host cell used in the inventive method is a yeast cell and step (a) of the inventive method further comprises mating of at least a first and second yeast cell, whereby said first and second host cells comprise different polynucleotides of which at least one encodes a Fc domain-containing fusion protein and whereby said polynucleotides of said first and second host cell comprise at least one distinct selectable marker.

In one embodiment, said first yeast cell used in the inventive method above comprises polynucleotides encoding immunoglobulin light chains and/or wherein said second yeast cell used in the inventive method comprises polynucleotides encoding immunoglobulin heavy chains.

In one embodiment of the inventive method said first yeast cell comprises polynucleotides encoding an immunoglobulin light chain library and wherein said second yeast cell comprises polynucleotides encoding immunoglobulin heavy chains of pre-determined affinity to the protein of interest.

In one embodiment, the present invention provides an isolated nucleic acid molecule comprising the nucleotide sequence according to SEQ ID NO. 5.

According to a one embodiment, the present invention provides an isolated protein encoded by the nucleic acid sequence according to SEQ ID NO: 5, in which the amino acid sequence according to SEQ ID NO. 4 has been removed.

In one embodiment, the present invention pertains to the provision of a host cell, which comprises at least one nucleic acid molecule comprising the nucleotide sequence according to SEQ ID NO: 5.

According to one embodiment, the present invention provides a process for producing a protein encoded by the nucleic acid sequence according to SEQ ID NO: 5, in which the amino acid sequence according to SEQ ID NO. 4 has been removed, the process comprising:
Culturing in vitro the host cell as disclosed above under conditions sufficient for protein expression;
Expressing the protein encoded by the polynucleotide comprising the nucleic acid sequence according to SEQ ID NO: 5
Isolating and purifying said protein.

According to one embodiment, the isolated protein of the inventive process comprises the amino acid sequence according to SEQ ID NO: 3.

In one embodiment, the isolated and purified protein of the invention is a multimer.

According to one embodiment, the present invention pertains to the use of the protein obtainable by the inventive process as disclosed above in the inventive method as disclosed above.

In one embodiment, the present invention provides a kit of parts, which comprises:
A first label according to the invention as disclosed above,
An isolated protein according to the invention as disclosed above and/or a polynucleotide according to the invention as disclosed above comprising the nucleotide sequence of SEQ ID NO: 5 for use in a process for protein production as disclosed above,
A host cell for use in a method for protein surface display according to the inventive method as disclosed above.

In one embodiment, the inventive kit comprises a host cell as disclosed herein.

According to one embodiment, the inventive kit may comprise lyophilized second label as disclosed above and/or the lyophilized polynucleotide comprising the nucleotide sequence of SEQ ID NO:5 as disclosed above.

SEQUENCE LISTING

Figure 1A:
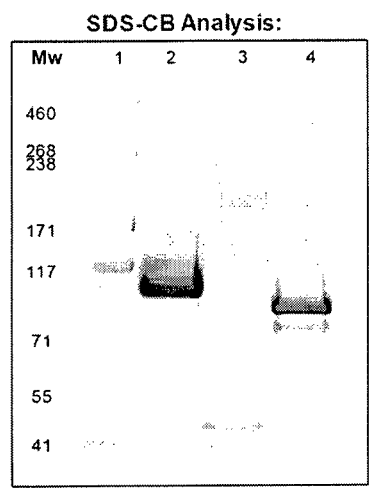
FIG. 1: (A) Coomassie blue gel analysis shows SA-ZZ tetramer (lane 4) and native monomer and tetramer (lane 3), (B) Western blot analysis shows that SA-ZZ binds IgG (left) and biotinylated protein (right). The apparent size of the monomer is 31 KD (lane 3) and the tetramer 91 KD (lane 2).

SEQ ID NO: 1 Amino acid sequence of Fc-domain binding (ZZ) domain as comprised in second label
SEQ ID NO: 2 Amino acid sequence of streptavidin (SA) as comprised in second label
SEQ ID NO: 3 Amino acid sequence of SA-ZZ fusion protein
SEQ ID NO: 4 Amino acid sequence of signal peptide
SEQ ID NO: 5 Nucleotide sequence of second label
SEQ ID NO: 6 Amino acid sequence of the inventive second label including signal sequence
SEQ ID NO: 7 Primer used in library generation
SEQ ID NO: 8 Primer used in library generation
SEQ ID. NO: 10 artificial leader sequence
SEQ ID NO: 11 artificial leader sequence
SEQ ID NO: 12 artificial leader sequence
SEQ ID NO: 13 artificial leader sequence
SEQ ID NO: 14 artificial leader sequence
SEQ ID NO: 15 artificial leader sequence
SEQ ID NO: 16 artificial leader sequence
SEQ ID NO: 17 artificial leader sequence
SEQ ID NO: 18 artificial leader sequence
SEQ ID NO: 19 artificial leader sequence
SEQ ID NO: 20 artificial leader sequence
SEQ ID NO: 21 artificial leader sequence
SEQ ID NO: 22 artificial leader sequence
SEQ ID NO: 23 artificial leader sequence
SEQ ID NO: 24 artificial leader sequence
SEQ ID NO: 25 artificial leader sequence
SEQ ID NO: 26 artificial leader sequence
SEQ ID NO: 27 artificial leader sequence
SEQ ID NO: 28 artificial leader sequence
SEQ ID NO: 29 Up-Primer for CDR-H3 library generation
SEQ ID NO: 28 Low-Primer for CDR-H3 library generation

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of".

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The described objectives are solved by the present invention, preferably by the subject matter of the appended claims. The inventors have surprisingly found that proteins may be non-covalently displayed on the surface of host cells by the inventive method.

The present invention is solved according to a first embodiment by a method for protein display on the surface of a host cell, whereby the inventive method comprises the steps of (a) introducing at least one or more polynucleotides into a host cell, which encode a protein of interest to be displayed on the surface of said host cell, (b) contacting the surface of said host cell with a first label; (c) contacting the surface of said host cell of (b) with a second label, whereby the second label specifically and non-covalently binds to said first label and said protein of interest encoded by said at least one or more polynucleotides; (d) expressing said at least one or more polynucleotides in said host cell under conditions sufficient for secretion of said protein of interest encoded by the at least one or more polynucleotides; (e) detecting host cells, which display said protein of interest from step (d) bound by the second label on the surface of said host cells, (f) contacting said host cells of step (e) with means for specifically detecting said protein of interest bound by said second label. The term "host" cell as used in the inventive method may by any cell suited for the expression of the protein of interest, such as e.g. yeast cells, insect cells, fish or mammalian cells.

The term "introducing" as used with the inventive method shall refer to any method suited to introduce or transfer polynucleotides into host cells, e.g. transformation, transduction, transfection by any technology known in the art. Herein, the term "transformation" as used with the inventive method is used to describe the introduction of polynucleotides, such as e.g. plasmids, into yeast cells or fungal cells, the term "transduction" as used for the inventive method refers to viral introduction or viral transfer of polynucleotides or genetic material into mammalian, fish or insect cells. Any known viral system may be used for transduction of the host cell of the present invention, such as e.g. adenoviral based systems, adeno-associated (AAV)-based systems, retroviral systems, such as e.g. Moloney murine leukaemia virus (Mo-MLV)-based e systems, or lentiviral expression systems, or herpes simplex virus (HSV)-based systems may be used, or other virus based systems such as e.g. vaccine, Epstein-Barr, Sendai, Sindbids, polyoma and measles virus-based systems (see e.g. Mah et al. (2002) Clin. Pharmocokin (12):901-911). If the host cells used in the inventive method are insect cells, baculoviral expression systems may e.g. be used to introduce at least one or more polynucleotides into the hosts cell, however, baculoviruses may also be used to introduce the polynucleotides according to the invention into the host cell (see e.g. Hofmann et al. Proc Natl Acad Sci USA (1995), 92:10099-10103; Boyce F M, et al. Proc Natl Acad Sci USA (1996), 93:2348-2352). The term "transfection" as used for the inventive method refers to the uptake of nucleic acids by a host cell via any suitable method known in the art, such as methods disclosed in Graham et al. (1973); Sambrook et al. (1989) Molecular Cloning, a laboratory manual, Cold Spring Harbor Laboratories, New York, Davis et al. (1986) Basic Methods in Molecular Biology, Elsevier, particularly calcium phosphate co-precipitation, direct microinjection into cultured cells, ultrasound-mediated gene transfection, electroporation, lipofection, or nucleofection.

For example, yeast cells may be used in the inventive method and may be cultured and transformed as described in Benatuil et al. Protein Engineering, Design & Selection vol. 23 no. 4 pp. 155-159, 2010. For example to obtain electro-competent yeast cells, *S. cerevisiae* cells (EBY100) may be grown overnight to stationary phase (OD600 to or about 3) in YPD media (10 g/l yeast nitrogen base, 20 g/l Peptone and 20 g/l D-(+)-Glucose) on a platform shaker at 225 rpm and 30° C. Subsequently, an aliquot of the overnight culture may e.g. be inoculated at an initial OD600 of 0.3. For example, the cells may then allowed to continue to grow on a platform shaker at 30° C. and 225 rpm until OD600 is approximately 1.6. The cells may then be collected by centrifugation at 3000 rpm for 3 minutes and remove the media. The cells may then e.g. be washed twice in 50 ml ice-cold water and once in 50 ml of ice-cold electroporation buffer (1 M Sorbitol/1 mM $CaCl_2$). The yeast cells may then be conditioned by re-suspending the cell pellet in 20 ml 0.1 M LiAc/10 mM DTT and shaking at 225 rpm in a culture flask for 30 minutes at 30° C. Subsequently, the conditioned cells may be collected by centrifugation, washed e.g. once in 50 ml ice-cold electroporation buffer, pelted by centrifugation and re-suspended in e.g. 100 to 200 µl electroporation buffer to reach a final volume of 1 ml, corresponding to approximately $1.6 \times 10^9$ cells/ml. For example, electroporation of the yeast cells 400 µl may be used and kept on ice until electroporation. If required, such as e.g. for the transformation of a large number of polynucleotides, such as e.g. when transforming human antibody libraries, the amount of yeast cells used for electroporation may be scaled up, e.g. 500 µl, 600 µl, 700 µl, 800 µl, 900 µl or 1 ml of conditioned cells may be used. The polynucleotides used for transformation (electroporation) of the yeast cells in the inventive method should e.g. preferably be prepared beforehand. For electroporation of the polynucleotides according to the invention from about 1 to about 50 µg of polynucleotides may be used, e.g. from about 2 µg to about 48 µg, or from about 4 µg to about 45 µg, or from about 6 µg to about 40 µg, from about 8 µg to about 35 µg, from about 10 µg to about 25 µg, or from about 12 µg to about 20 µg, or from about 4 µg to about 18 µg, or from about 6 µg to about 16 µg, or from about 7 µg to about 14 µg, or from about 5 µg to about 12 µg, or 2 µg, 3 µg, 4 µg, 5 µg, 6 µg, 7 µg, 8 µg, 9 µg, 10 µg, 11 µg, 12 µg, 13 µg, 14 µg, 15 µg, 16 µg, 17 µg, 18 µg, 19 µg, 20 µg, 21 µg, 22 µg, 23 µg, 24 µg, 25 µg, 26 µg, 27 µg, 28 µg, 29 µg, 30 µg, 31 µg, 32 µg, 33 µg, 34 µg, 35 µg, 36 µg, 37 µg, 38 µg, 39 µg, 40 µg, 41 µg, 42 µg, 43 µg, 44 µg, 45 µg, 46 µg, 47 µg, 48 µg, 49 µg, or 50 µg of polynucleotides may be used for electroporation. Preferably, the volume of the polynucleotides should be less than 50 µl. Then, the conditioned yeast cells may e.g. be gently mixed with the polynucleotides, transferred into a pre-chilled electroporation cuvette, e.g. 0.2 cm electrode gap and incubated for about 5 minutes on ice, after which the yeast cells may be electroporated at e.g. 2.5 kV and 25 µF, whereby the time constant should e.g. range from 3.0 to 4.5 milliseconds. The electroporated yeast cells may then be transferred into 8 ml of 1:1 mix of 1 M sorbitol: YPD media and for example incubated on a platform shaker at 225 rpm and 30° C. for 1 hour. The cells may then e.g. be collected by centrifugation and resuspended in SD-UT media (20 g/l glucose, 6.7 g/l yeast nitrogen base without amino acids, 5.4 g/l $Na_2HPO_4$, 8.6 g/l $NaH_2PO_4 \times H_2O$ and 5 g/l casamino acids [CSM-TRP-URA]). For example, for every 400 µl of electroporated yeast cell 250 ml of SD-UT media may be used.

The terms polynucleotide or nucleic acid as used in the inventive method generally refer to molecules comprising a plurality of nucleotides. Exemplary polynucleotides include deoxyribonucleic acids, ribonucleic acids, and synthetic analogues thereof, including peptide nucleic acids. For example, the polynucleotides according to the present invention may comprise viral RNA or DNA which comprises at least one, e.g. 1, 2, 3, 4, 5, 6, 7, 8, 9 or 10 or more nucleotide sequences encoding the protein of interest. The at least one polynucleotide used in the present invention may e.g. also be provided as one or more expression vectors (plasmids), e.g. 1, 2, 3, 4, 5, 6, or more expression vectors, whereby the term expression vector refers to a vector, or episomal vector, which is generally a plasmid that is used to introduce and express a specific gene, such as e.g. the protein of interest to be non-covalently displayed on the surface of a host cell according to the present invention, into a target cell. Expression vectors allow production of large amounts of stable mRNA. Once the expression vector is inside the cell, the protein that is encoded by the gene is produced by the cellular transcription and translation machinery. The plasmid is engineered such that it contains a highly active promoter which causes the production of large amounts of mRNA. An episomal vector is capable of self-replicating autonomously within the host cells. The term "protein" which is encoded by the at least one or more polynucleotides to be displayed by the inventive method on the surface of a host cell, refers to full length proteins, protein fragments, proteins in their native state or denatured proteins. For example, proteins or protein fragments to be displayed on the surface of a host cell according to the invention may comprise from about 50 to about 35000 amino acids, or from about 100 to about 32500 amino acids, or from about 125 amino acids to about 30000 amino acids, or from about 150 to about 27500 amino acids, or from about 200 amino acids to about 27000 amino acids, or from about 220 to about 26750 amino acids, or from about 250 to about 26500 amino acids, or from about 300 amino acids to about 26000 amino acids, or from about 60, 70, 80, 90, 100, 110, 120, 130, 140, 160, 170, 180, 190, 200, 210, 220, 230, 240, 260, 270, 280, 290, 325, 350, 375, 400, 425, 450, 475, 500, 525, 550, 575, 600, 625, 650, 675, 700, 725, 750, 775, 800, 850, 900, 950, 1000 to about 1100, 1150, 1200, 1250, 1300, 1350, 1400, 1450, 1500, 1550, 1600, 1650, 1700, 1750, 1800, 1850, 1900, 1950, 2000 amino acids.

The inventive method further comprises contacting the surface of a host cell with a first label, whereby the term "contacting" refers to the process of bringing into contact at least two distinct entities, e.g. at least a host cell and at least one first label, such that they can react with or bind to the surface of the host cell. The first label according to the invention may e.g. be a sugar, amino acid, protein, peptide, enzyme, lipid, vitamin, nucleic acid, peptide nucleic acids, ganglioside, or quantum dot, protein A, each of which may e.g. be functionalized to react with the surface of the host cell of the inventive method, e.g. the aforementioned compounds may comprise reactive groups such as N-hydroxysuccinimde (NHS) esters, or tetrafluorophyl ester (THF). The inventive method further comprises contacting the surface of the host cell as disclosed above with a second label, whereby the second label specifically and non-covalently binds to said first label and said protein of interest encoded by said at least one or more polynucleotides. The second label according to the invention may e.g. include ganglioside binding proteins (lectins), enzyme pseudo substrates, enzymes, such as kinases, fusion proteins, which bind the first label on the surface of the host cell according to the invention and are capable of binding the protein of interest, e.g. the second label may be a multimeric protein, of which at least one protein domain or fragment is capable of binding to the first label, and at least a second domain which is capable of binding to the protein of interest.

The inventive method further comprises the expression of the protein of interest encoded by the at least one or more polynucleotides under conditions which are sufficient for the secretion of the protein of interest. For example, mammalian cells may be cultured as described in Basic Techniques in Mammalian Cell Tissue Culture (Phelan, Current Protocols in Cell Biology 1.1.1-1.1.18, September 2007) utilizing cell culture media such as, e.g. DMEM, RPMI 1640, MEM, Ham's DMEM/F12, or serum- or protein-free culture media, such as e.g. Expi293™ (Life Technologies), or Freestyle™ medium (Life Technologies). For example, insect cells may be cultured in Grace's Insect TC medium, or Schneider's *Drosophila* medium.

The inventive method further comprises as step (e) detecting host cells, which display the protein of interest as encoded by the at least one polynucleotide as disclosed above, which is bound by the second label according to the inventive method on the surface of the host cell. The inventive method further comprises contacting the host cell as disclosed above with means, which specifically detect the protein of interest, which is non-covalently bound by the second label. "Detection" as used in the inventive method refers to quantitatively or qualitatively determining the presence or absence of a host cell to the surface of which the protein of interest is non-covalently bound by means of the second label, whereby the second label is bound to the first label on the surface of the host cell.

In one embodiment the protein of interest displayed on the surface of a host cell according to the invention may be a monomeric or a multimeric protein, e.g. the protein of interest may be comprised of one polypeptide chains or may comprise 2-22, 3-20, 4-18, 5-17, 6-16, 7-15, 8-14, 9-13, 10-12, or 2, 3, 4, 5, 6, 7, 8, 9, 10, 11, 12, 13, 14, 15, 16, 17, 18, 19, 20, 21 or 22 subunits, each of which may comprise a polypeptide or protein comprising a number of amino acids as disclosed above. The polypeptide chains of the multimeric protein may e.g. also be linked by disulfide bonds, which may e.g. be formed between cysteine residues of the individual polypeptide chains or protein fragments. Accordingly, the protein of interest may e.g. be a multimeric protein, which comprises more than 35000 amino acids. The protein of interest displayed by the inventive method may e.g. be a homomeric protein which is comprised of identical polypeptides or proteins, e.g. the protein of interest may comprise 2-22, 4-18, 6-16, 8-14, 10-12, or 2, 3, 4, 5, 6, 7, 8, 9, 10, 11, 12, 13, 14, 15, 16, 17, 18, 19, 20, 21, 22 identical polypeptide chains (subunits), which may, e.g. be linked by disulfide bonds, or may e.g. form a multimeric complex by non-covalent interactions, such as e.g. hydrophobic protein-protein-interactions. The magnitude of the hydrophobic effect for a given compound, such as e.g. the protein of interest, may be estimated by measuring the free energy of transfer, $\Delta G_{tr}$, of the compound from the gas, liquid or solid phase to water. A positive value for $\Delta G_{tr}$ means that the molecule prefers a nonaqueous environment. In the case of the amino acids, measurements can be made with the free amino acid or with variants modified to better represent the amino acids incorporated within the protein chain. For example, the protein of interest may also be a hetermeric protein and comprise two or more different polypeptides or subunits or proteins, e.g. the protein of interest may comprise 2-22, or 3, 4, 5, 6, 7, 8, 9, 10, 11, 12, 13, 14, 15, 16, 17, 18, 19, 20, 21 or 22 different polypeptides or subunits, which may e.g. be joined by disulfide bonds, hydrophobic interactions or joined by linkers or artificial linkers. The term "linker" or "linkage" as used for the protein of interest of the inventive method refers to a linking moiety that connects two proteins, or polypeptides and has a backbone of about 5 to about 20 atoms in length. For example, a linker or linkage may be a covalent bond that connects two polypeptides or proteins of the protein of interest according to the invention or a chain of between 1 and 20 atoms in length, e.g. of about 1, 2, 3, 4, 5, 6, 8, 10, 12, 14, 16, 18, 19, or 20 carbon atoms in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may e.g. be saturated or unsaturated, whereby usually no more than one, two, or three unsaturated bonds will be present in a linker backbone. The linker may e.g. include one or more substituent groups, for example an alkyl, aryl or alkenyl group. A linker may include, without limitations, oligo(ethylene glycol), ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may e.g. include a cyclic group, such as an aryl, a heterocycle or a cycloalkyl group, where 2 or more atoms, e.g., 2, 3 or 4 atoms, of the cyclic group are included in the backbone and may be cleavable or non-cleavable. The protein of interest may e.g. be artificial protein, e.g. a non-naturally occurring protein and comprise e.g. fusions of naturally occurring proteins or protein fragments, or e.g. may comprise conservative or non-conservative amino acid substitutions, or may comprise substitutions, deletions or additions of one or more amino acids, e.g. the artificial protein of interest may comprise 1-100, 5-90, 10-80, 15-75, 20-70, 25-65, 30-55, 35-50, 40-45, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 35, 36, 37, 38, 39, 40, 41, 42, 43, 44, 46, 47, 48, 49, 51, 52, 53, 54, 55, 56, 57, 58, 59, 60, 61, 62, 63, 64, 65, 66, 67, 68, 69, or 70 conservative or non-conservative amino acid substitutions compared to the naturally occurring protein or protein fragment. For Example, conservative amino acid substitution in the protein of interest of the present invention refers to the replacement of one amino acid with another amino acid having similar properties, such as e.g., size, charge, hydrophobicity, hydrophilicity, and/or aromaticity, and includes exchanges within one of the following five groups:

| Group | Amino acids |
|---|---|
| I (small aliphatic, nonpolar or slightly polar residues) | Ala, Ser, Thr, Pro, Gly; |
| II (polar, negative-charged residues) | Asp, Asn, Glu, Gln, |
| III (polar, positive-charged residues) | His, Arg, Lys; |
| IV (large, aliphatic, nonpolar residues) | Met, Leu, Ile, Val, Cys |
| V (large, aromatic residues) | Phe, Tyr, Trp, |

Non-conservative amino acid substitution in the protein of interest of the present invention include e.g. substitutions between different groups I-V as disclosed above, e.g. between group I and II, I and III, I and IV, I and V, II and III, II and IV, II and V, III and IV, III and V.

According to one embodiment, the protein of interest of the present invention encoded by the at least one polynucleotide comprises a signal peptide. Herein, signal sequence as used for the protein of interest of the inventive method refers to an amino acid sequence which is capable of initiating the passage of a polypeptide, to which it is operably linked, e.g. by a peptide bond, into the endoplasmic reticulum (ER) of a host cell. The signal peptide is generally cleaved off by an endopeptidase (e.g. a specific ER-located signal peptidase) to release the (mature) polypeptide. The length of a signal peptide is typically in the range from about 10 to about 40 amino acids. In one embodiment as used herein, the term "a nucleic acid sequence encoding a signal peptide" does not include within its scope a nucleic acid sequence encoding the full length sequence of the homologous polypeptide for which a signal peptide naturally initiates passage into the endoplasmic reticulum. In particular said signal peptide may be capable of directing the polypeptide into a cell's secretory pathway. For example, if the host cell of the invention is a mammalian cell, the leader sequences which are operatively linked to the protein of interest according to the invention may include MELGLSWIFLLAILKGVQC (SEQ ID NO: 9), MELGLRWVFLVAILEGVQC (SEQ ID NO: 10), MKHLWFFLLLVAAPRWVLS (SEQ ID NO: 11), MDWTWRILFLVAAATGAHS (SEQ ID NO: 12), MDWTWRFLFWAAATGVQS (SEQ ID NO: 13), MEFGLSWLFLVAILKGVQC ((SEQ ID NO: 14), MEFGLSWVFLVALFRGVQC (SEQ ID NO: 15), MDLLHKNMKHLWFFLLLVAAPRWVLS ((SEQ ID NO: 16), MDMRVPAQLLGLLLLWLSGARC (SEQ ID NO: 17), MKYLLPTAAAGLLLLAAQPAMA (SEQ ID NO: 18), MPLLLLLPLLWAGALA (SEQ ID NO: 19), MKVLILACLVALALA, MKWVTFISLLFLFSSAYS . . . RGVFRR ((SEQ ID NO: 20), For example, if insect cells are used as host cells in the inventive method, appropriate signal sequences for insect cells should be used, which as one example may include MKFLVNVALVFMVVYISYIYA (SEQ ID NO: 28).

For example, if yeast cells are used as host cells in the inventive method, appropriate signal sequences for yeast cells should be used, e.g. such as those disclosed in Massahi et al. Journal of Theoretical Biology 364 (2015) 179-188, which may e.g. include preferably amino-terminally, the MF☐1pp secretory leader, MQVKSIVNLLLACSLAVA ((SEQ ID NO: 21), MQFNWNIKTVASILSALTLAQA (SEQ ID NO: 22), MQFNSVVISQLLLTLASVSMG (SEQ ID NO: 23), MRFSTTLATAATALFFTASQVSA (SEQ ID NO: 24), MESVSSLFNIFSTIMVNYKSLVLALLSVSNLKYARG (SEQ ID NO: 25), MRFPSIFTAVLFAASSALA (SEQ ID NO: 26), MFKSVVYSILAASLANA (SEQ ID NO: 27).

According to one embodiment of the present invention, the first label of the inventive method is covalently bound to the surface of the host cell. Accordingly, the first label may e.g. be covalently bound to the surface of a mammalian cell, or e.g. covalently bound to the surface of an insect cell, or e.g. may be covalently bound to the surface of a yeast cell. As used with the inventive method the term "covalently bound", or "covalent bond" refers to a bond between two atoms formed by sharing at least one pair of electrons, e.g. bonds formed between C—C, C═C, N—C, or S—S.

According to a preferred embodiment, the first label of the present invention is biotin, or a biotin-derivative. Accordingly, the first label of the inventive method may e.g. include biotin or a biotin analogue such as desthiobiotin, oxybiotin, 2'-iminobiotin, diaminobiotin, biotin sulfoxide, biocytin, etc, which may be covalently bound to the surface of a host cell according to the invention by reactive groups such as e.g. N-hydroxysuccinimde (NHS) esters, or tetrafluorophyl ester (THF). For example, biotin derivatives which may be used as a first label in the inventive method may also include a linker, e.g., -LC-biotin, -LC-LC-Biotin, -SLC-Biotin or -PEGn-Biotin where n is 3-12 (e.g. n=1, 2, 3, 4, 5, 6, 7, 8, 9, 10, 11, or 12). For example, the first label may include NHS-PEO4-Biotin, NHS-dPEG4-Biotin, NHS-PEG12-Biotin, NHS-dPEG12-Biotin, Biotion-PEG-SCM (3.4 kD), sulfo-NHS-biotin, sulfo-NHS-LC-biotin, sulfo-NHS-LC-LC-biotin, alkoxyamine-PEG12-biotin, alkoxyamine-PEG4-biotin, hydrazide-Biocytin, hydrazine-PEG4-biotin, pyridyldisulfide-biotin, biotin-BMCC (1-Biotinamido-4-[4'-(maleimidomethyl)cyclohexanecarboxamido]butane), maleimide-PEO2-biotin, mal-dPEG2-biotin, maleimido-PEG2-biotin, maleimide-PEO11-biotin, mal-dPEG11-biotin, maleimido-PEG11-biotin, or long-chain (LC) iodoacetyl-biotin.

According to one embodiment, the second label of the inventive method is a further protein or polypeptide. For example, the second label of the inventive method may be a further protein that binds biotin, or a biotin-derivate as disclosed above.

In a preferred embodiment of the present invention, the second label of the inventive method is a multimeric protein. Accordingly, the further protein (second label) may comprise more than one protein, e.g. the second label may comprise 2, 3, 4, 5, 6, 7, 8, 9, or 10 proteins which may be covalently linked by e.g. one or more disulfide bonds between the individual proteins comprised in the second label. The proteins comprised in the second label of the inventive method may, however also be linked non-covalently, e.g. by hydrophobic interactions, electrostatic interaction between charged amino acid residues between individual protein constituents of the second label.

According to one embodiment, the second label of the inventive method comprises one of protein A, protein L, protein G, protein A-G fusion, or domains E, D, A, B of protein A. Accordingly, the second label protein A, protein L, protein G, protein A-G fusion, or domains E, D, A, B of protein A and specifically and non-covalently binds to the inventive first label as disclosed above. Accordingly, the second label may e.g. comprise avidin, or streptavidin in addition to protein A, protein L, protein G, protein A-G fusion, or domains E, D, A, B of protein. For example, the second label of the inventive method may comprise e.g. a protein A-avidin fusion protein, or a protein L-avidin fusion protein, or a protein G avidin fusion protein, or a protein A-G fusion protein fused to avidin, or domain E of protein A fused to avidin, or domain D of protein A fused to avidin, or domain A of protein A fused to avidin, or domain B of protein A fused to avidin, or e.g. protein A-streptavidin fusion protein, or a protein L-streptavidin fusion protein, or a protein G streptavidin fusion protein, or a protein A-G fusion protein fused to streptavidin, or domain E of protein A fused to streptavidin, or domain D of protein A fused to streptavidin, or domain A of protein A fused to streptavidin, or domain B of protein A fused to streptavidin. The term "fusion protein" or "fusion" as used with the inventive second label refers to components such as e.g. proteins or polypeptides that are linked by a peptide bond. Fusion proteins of the invention may be amino-terminal or carboxyterminal fusions. In one embodiment, the inventive second label may also comprise neutravidin, chicken avidin-related proteins (AVRs, e.g. AVR4), dual-chain avidin (dcAvd), or sequence variants thereof, such as e.g. avidin mutant Y33H, avidin mutant H117C, avidin mutant [W110K] [N54A], streptavidin mutant V47G, streptavidin mutant S112F, streptavidin mutant S112R, or streptavidin mutant S112K to bind to the inventive first label.

Preferred proteins of the inventive second label that bind the protein of interest are those, which e.g. exhibit high affinity, e.g. having a binding constant of at least $K_D = 10^{-9}$ M, $10^{-10}$ M, $10^{-11}$ M, or $10^{-12}$ M, for antibody Fc-domains, or antibody Fab regions, or antibody light chains (VL-kappa).

In one embodiment the, the host cell of the inventive method may e.g. be selected from mammalian, yeast, or insect cell. In a preferred embodiment, the host cell of the inventive method is a yeast cell selected from the group comprising *Saccharomyces cerevisiae, Hansenula polymor-* pha, *Schizosaccharomyces pombe, Schwanniomyces occidentalis, Kluyveromyceslactis, Yarrowia lipolytica* and *Pichia pastoris*.

According to a preferred embodiment, the host cell of the inventive method is a mammalian cell. For example, the mammalian cells may be selected from the group comprising HEK293, HEK293T, HEK293E, HEK 293F, NS0, per.C6, MCF-7, HeLa, Cos-1, Cos-7, PC-12, 3T3, Vero, vero-76, PC3, U87, SAOS-2, LNCAP, DU145, A431, A549, B35, H1299, HUVEC, Jurkat, MDA-MB-231, MDA-MB-468, MDA-MB-435, Caco-2, CHO, CHO-K1, CHO-B11, CHO-DG44, BHK, AGE1.HN, Namalwa, WI-38, MRC-5, HepG2, L-929, RAB-9, SIRC, RK13, 11B11, 1D3, 2.4G2, A-10, B-35, C-6, F4/80, IEC-18, L2, MH1C1, NRK, NRK-49F, NRK-52E, RMC, CV-1, BT, MDBK, CPAE, MDCK.1, MDCK.2, and D-17.

In one embodiment, the host cell of the inventive method is an insect cell, which may be selected from the group comprising Sf9, Sf21, S2, or BTI-TN-561-4 cells.

According to one embodiment, the means for specifically detecting the protein of interest on the surface of host cells in the inventive method are selected from the group comprising antibodies or antibody fragments, quantum dots, enzymes, fluorophores, or intercalating dyes, and gangliosides.

Accordingly, the means for specifically detecting the protein of interest may be for example an antibody, whereby the term "antibody" refers to (a) immunoglobulin polypeptides and immunologically active portions of immunoglobulin polypeptides, i.e., polypeptides of the immunoglobulin family, or fragments thereof, that contain an antigen binding site that immunospecifically binds to a specific antigen (e.g., the protein of interest), or (b) conservatively substituted derivatives of such immunoglobulin polypeptides or fragments that immunospecifically bind to the antigen (e.g. the protein of interest (POI)). Antibodies are generally described in, for example, Harlow & Lane, Antibodies: A Laboratory Manual (Cold Spring Harbor Laboratory Press, 1988), whereby the term "immunospecifically" as used in the inventive method refers to the ability of an individual antibody or antibody fragment as disclosed herein to react with only one antigenic determinant and do not specifically bind to other polypeptides.

For example, quantum dots may be used to specifically detect the protein of interest in the inventive method. In the inventive method (e.g. in step (e) of the inventive method), the term "quantum dot" refers to a single spherical nanocrystal of semiconductor material where the radius of the nanocrystal is less than or equal to the size of the exciton Bohr radius for that semiconductor material (the value for the exciton Bohr radius can be calculated from data found in handbooks containing information on semiconductor properties, such as the CRC Handbook of Chemistry and Physics, 83rd ed., Lide, David R. (Editor), CRC Press, Boca Raton, Fla. (2002)). Quantum dots are known in the art, as they are described in references, such as Weller, Angew. Chem. Int. Ed. Engl. 32: 41-53 (1993), Alivisatos, J. Phys. Chem. 100: 13226-13239 (1996), and Alivisatos, Science 271: 933-937 (1996). Quantum dots may e.g. be from about 1 nm to about 1000 nm diameter, e.g. 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, or 500 nm, preferably at least about 2 nm to about 50 nm, more preferably QDs are at least about 2 nm to about 20 nm in diameter (for example about 2, 3, 4, 5, 6, 7, 8, 9, 10, 11, 12, 13, 14, 15, 16, 17, 18, 19, or 20 nm). QDs are characterized by their substantially uniform nanometer size, frequently exhibiting approximately a 10% to 15% polydispersion or range in size. A QD is capable of emitting electromagnetic radiation upon excitation (i.e., the QD is photoluminescent) and includes a "core" of one or more first semiconductor materials, and may be surrounded by a "shell" of a second semiconductor material.

A QD core surrounded by a semiconductor shell is referred to as a "core/shell" QD. The surrounding "shell" material will preferably have a bandgap energy that is larger than the bandgap energy of the core material and may be chosen to have an atomic spacing close to that of the "core" substrate. The core and/or the shell can be a semiconductor material including, but not limited to, those of the groups II-VI (ZnS, ZnSe, ZnTe, US, CdSe, CdTe, HgS, HgSe, HgTe, MgS, MgSe, MgTe, CaS, CaSe, CaTe, SrS, SrSe, SrTe, BaS, BaSe, BaTe, and the like) and III-V (GaN, GaP, GaAs, GaSb, InN, InP, InAs, InSb, and the like) and IV (Ge, Si, and the like) materials, PbS, PbSe, and an alloy or a mixture thereof. Preferred shell materials include ZnS.

The term "fluorophores", "fluorescent label", or "fluorescent dye", or "fluorophore" as used in the inventive method for specifically detecting the protein of interest on the surface of host cells refers to moieties that absorb light energy at a defined excitation wavelength and emit light energy at a different wavelength. Examples of fluorescent labels that may be used for specific detection of the protein of interest according to the invention may include, but are not limited to: dansyl chloride, dapoxyl, dialkylaminocoumarin, rhodamine isothiocyanate, Alexa 350, Alexa 430, Alexa Fluor 488, Alexa Fluor 532, Alexa Fluor 546, Alexa Fluor 568, Alexa Fluor 594, Alexa Fluor 633, Alexa Fluor 660, Alexa Fluor 680, AMCA, aminoacridine, BODIPY 630/650, BODIPY 650/665, BODIPY-FL, BODIPY-R6G, BODIPY-TMR, BODIPY-TRX, BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxy coumarin, Naphtho fluorescein, Oregon Green 488, Oregon Green 500, Oregon Green 514, Pacific Blue, PyMPO, 5-carboxy-4',5'-dichloro-2',7'-dimethoxy fluorescein, 5-carboxy-2',4',5',7'-tetrachlorofluorescein, 5-carboxyfluorescein, 5-carboxyrhodamine, 6-carboxyrhodamine, 6-carboxytetramethyl amino, Cascade Blue, Cy2, Cy3, Cy5,6-FAM, dansyl chloride, fluorescein, HEX, 6-JOE, NBD (7-nitrobenz-2-oxa-l,3-diazole), Oregon Green 488, Oregon Green 500, Oregon Green 514, Pacific Blue, phthalic acid, terephthalic acid, isophthalic acid, cresyl fast violet, cresyl blue violet, brilliant cresyl blue, para-aminobenzoic acid, erythrosine, phthalocyanines, azomethines, cyanines, xanthines, succinylfluoresceins, rare earth metal cryptates, europium trisbipyridine diamine, a europium cryptate or chelate, diamine, dicyanins, La Jolla blue dye, allopycocyanin, allococyanin B, phycocyanin C, phycocyanin R, thiamine, phycoerythrocyanin, phycoerythrin R, REG, Rhodamine Green, rhodamine isothiocyanate, Rhodamine Red, TAMRA, TET, TRIT (tetramethyl rhodamine isothiol), Tetramethylrhodamine, or Texas Red. For example, intercalating dyes, which may be used in the inventive method are typically planar, aromatic, ring-shaped chromophore molecules. In some embodiments, intercalating dyes include fluorescent dyes.

Numerous intercalating dyes are known in the art. Some non-limiting examples include PICO GREEN (P-7581, Molecular Probes), EB (E-8751, Sigma), propidium iodide (P-4170, Sigma), Acridine orange (A-6014, Sigma), 7-aminoactinomycin D (A-1310, Molecular Probes), cyanine dyes (e.g., TOTO, YOYO, BOBO, and POPO), SYTO, SYBR Green I, SYBR Green II, SYBR DX, OliGreen, CyQuant GR, SYTOX Green, SYTO9, SYTO10, SYTO17, SYBR14, FUN-1, DEAD Red, Hexidium Iodide, Dihydroethidium, 9-Amino-6-Chloro-2-Methoxyacridine, DAPI, DIPI, Indole dye, Imidazole dye, Actinomycin D, Hydroxystilbamidine, BOXTO, LC Green, Evagreen, Bebo. In one embodiment, gangliosides may be used to detect the protein of interest in the inventive method, e.g. if the protein of interest binds to gangliosides. The term "ganglioside" as used in the present invention, refers to glycosphingolipids which contain several monosaccharide units per molecule. Examples of suitable monosaccharide units which can be contained in the gangliosides or ganglioside derivatives are D-galactose, N-acetyl D-galactosamine, glucose and N-acetylneuraminic acid. Gangliosides may be roughly classified, depending on the number of sialic acid residue or residues bound per molecule, into monosialoganglioside (GM), disialoganglioside (GD), trisialoganglioside (GT), and tetrasialoganglioside (GQ) in which four sialic acid residues are bound. They can be classified further depending on the position or positions of the sialic acid residue or residues bound. Gangliosides may e.g. include GM1 [n=0, m=1 in the general formula (1)] as GM, GD1a (n=1, m=1) and GD1b (n=1, m=2) as GD, GT1b (n=1, m=2) as GT, and GQ1b (n=2, m=2) as GQ. The gangliosides as disclosed herein may, e.g. further comprise a fluorophores as disclosed herein, or may e.g. be labeled with radioisotopes (e.g. $^{14}C$, $^{3}H$, $^{32}P$, $^{125}I$, $^{131}I$, or $^{125}I$) to allow or aid in their detection.

In one embodiment, the inventive method comprises contacting the host cells as disclosed above with means for specifically detecting the protein of interest which is non-covalently bound to the inventive second label. Accordingly, the means for specifically detecting the protein of interest non-covalently bound by the second label of the invention may e.g. be one of a polyclonal antibody, monoclonal antibody, scFv-Fc, scFv, (Fab')$_2$, Fab, diabody, or VHH antibody, which may optionally be coupled to a further label. For example, the protein of interest may be detected by a polyclonal antibody or polyclonal serum, monoclonal antibody, scFv-Fc, scFv, (Fab')$_2$, Fab, minibody, diabody, or VHH antibody which specifically bind to at least one epitope on the protein of interest, or which may e.g. also bind to epitopes that are formed by the second label of the invention and the protein of interest non-covalently bound thereto.

The term "Fab fragment" which may be used according to the embodiments of the inventive method refers to an antibody fragment comprising a light chain comprising a VL and CL region and a portion of a heavy chain comprising a Vn and a CH1 region. A Fab fragment does not comprise a CH2 or CH3 region (see e.g., Kuby, Immunology, Second Edition, pp. 1 10-1 1 W.H. Freeman and Co., New York (1994)). Different kinds of Fab fragments may contain either no hinge region, a portion of a hinge region, or an entire hinge region. A "scFv-Fc," as may be used in the inventive method is a recombinant protein that is a fusion of an scFv with an Fc region (see e.g. Li et al. (2000), Cancer Immunol, immunother. 49:243-252). The term "Fc domain" or "Fc region" as used in the inventive method refers to the portion of an immunoglobulin, e.g., an IgG molecule that correlates to a crystallizable fragment obtained by papain digestion of an IgG molecule. The Fc region comprises the C-terminal half of two heavy chains of an IgG molecule that are linked by disulfide bonds. It has no antigen binding activity but contains the carbohydrate moiety and binding sites for complement and Fc receptors, including the FcRn receptor. "Fc domain" includes for example native sequence Fc regions and variant Fc regions, e.g. such as those disclosed in WO 02/094852), as well as polymorphisms have been observed at a number of positions in Fc domains, including but not limited to positions 270, 272, 312, 315, 356, and 358. Within the inventive method, the term "Fc" can refer to this region in isolation, or this region in the context of an antibody, antibody fragment, or Fc fusion protein.

For example, an IgG Fc region may comprise an IgG CH2 and an IgG CH3 domain. The "CH2 domain" of a human IgG Fc region usually extends from an amino acid residue at about position 231 to an amino acid residue at about position 340, whereby a carbohydrate chain may be attached to the CH2 domain. The "CH3 domain" may comprise the stretch of amino acids C-terminal to a CH2 domain in an Fc region, e.g. from an amino acid residue at about position 341 to an amino acid residue at about position 447 of an IgG.

The term "diabody" used for the inventive method refers to an engineered antibody and/or antibody fragments that are bivalent, monospecific or bispecific molecules generated by dimerization of two variable heavy-variable light fragments. The term "VHH", as used for the inventive method refers to single heavy chain variable domain antibodies devoid of light chains. Preferably, a VHH is an antibody fragment of the type that can be found in e.g. Camelidae or cartilaginous fish which are naturally devoid of light chains, or the VHH may be a synthetic VHH which can be constructed accordingly (see e.g. Kim et al. Biochimica et Biophysica Acta 1844 (2014) 1983-2001; Janssens, R. et al. Proc. Natl. Acad. Sci. U.S.A. 2006, 103 (41), 15130-15135).

The term "polyclonal antibody" or "polyclonal serum" as used for the detection of the protein of interest of the invention refers to a heterogeneous pool of antibodies produced by a number of different B lymphocytes. Different antibodies in the pool recognize and specifically bind different epitopes, which typically are polypeptide sequence of at least about 3 to 5, preferably about 5 to 10 or 15, e.g. 3, 4, 5, 6, 7, 8, 9, 10, 11, 12, 13, 14, or 15 amino acids, but typically not more than about 1,000 amino acids (or any integer there between), which define a sequence that by itself or as part of a larger sequence, binds to an antibody generated in response to such sequence. A target antigen may contain linear and/or discontinuous epitopes. There is no critical upper limit to the length of the fragment, which may (for example) comprise nearly the full-length of the antigen sequence, or even a fusion protein comprising two or more epitopes from the target antigen. An epitope for use in the subject invention is not limited to a polypeptide having the exact sequence of the portion of the protein of interest from which it is derived and may comprise sequence variants. For example, the epitope may comprises sequences which comprise about 1-10 conservative, or non-conservative amino acid substitutions as disclosed above, preferably the amino acid sequence of the epitope recognized by the polyclonal antibody or polyclonal serum is at least 85%, or at least 90%, or at least 95%, or at least 98% identical to the corresponding sequence or sequences of the protein of interest. Thus the term "epitope" as used for the inventive method encompasses sequences identical to the native sequence, as well as mutations or modifications to the native sequence, such as deletions, additions and substitutions (generally conservative in nature).

For example, sequence identity of the amino acid sequence of the protein of interest of the invention or any protein as disclosed in the present invention is defined as the percentage of amino acid residues in a candidate sequence that are identical with the amino acid residues in a protein of interest of the invention, after aligning the sequences and introducing gaps, if necessary, to achieve the maximum percent sequence identity, and not considering any conservative substitutions as part of the sequence identity. Alignment for purposes of determining percent amino acid sequence identity may be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared.

For example, percent sequence identity may also be determined by methods as disclosed in Altschul et al, Bull Math. Bio. 48:603 (1986), and Henikoff and Henikoff, Proc. Natl Acad. Sci. USA 1992 Nov. 15; 89(22):10915-9. Briefly, two amino acid sequences are aligned to optimize the alignment scores using a gap opening penalty of 10, a gap extension penalty of 1, and the "BLOSUM 62" scoring matrix of Henikoff and Henikoff as disclosed below (amino acids are indicated by the standard one-letter codes). The percent identity is then calculated as: ([Total number of identical matches]/[length of the longer sequence plus the number of gaps introduced into the longer sequence in order to align the two sequences])*100).

of all paired amino acids using an amino acid substitution matrix, and the ends of the regions are "trimmed" to include only those residues that contribute to the highest score. If there are several regions with scores greater than the "cutoff value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol Biol. 48:444 (1970); Sellers, SIAM J. Appl. Math. 25:787 (1974)), which allows for amino acid insertions and deletions. Illustrative parameters for FASTA analysis are: ktup=I, gap opening penalty=10, gap extension penalty=I, and substitution matrix=BLOSUM62. These parameters can be introduced into a FASTA program by modifying the scoring matrix file ("SMATRK"), as explained in Appendix 2 of Pearson, Meth. Enzymol. 183:63 (1990).

The term "monoclonal antibody" as used herein refers to an antibody obtained from a population of substantially homogeneous antibodies, i.e., the individual antibodies comprising the population are identical except for possible naturally-occurring mutations that may be present in minor amounts, or e.g. differences in the extend of post-translational modifications, such as glycosylation or terminal lysine processing.

In one embodiment, the polyclonal antibody, monoclonal antibody, scFv-Fc, scFv, (Fab')$_2$, Fab, diabody, or VHH antibody which may be used in the inventive method are

| | Ala | Arg | Asn | Asp | Cys | Gln | Glu | Gly | His | Ile | Leu | Lys | Met | Phe | Pro | Ser | Thr | Trp | Tyr | Val |
|---|---|---|---|---|---|---|---|---|---|---|---|---|---|---|---|---|---|---|---|---|
| Ala | 4 | | | | | | | | | | | | | | | | | | | |
| Arg | −1 | 5 | | | | | | | | | | | | | | | | | | |
| Asn | −2 | 0 | 6 | | | | | | | | | | | | | | | | | |
| Asp | −2 | −2 | 1 | 6 | | | | | | | | | | | | | | | | |
| Cys | 0 | −3 | −3 | −3 | 9 | | | | | | | | | | | | | | | |
| Gln | −1 | 1 | 0 | 0 | −3 | 5 | | | | | | | | | | | | | | |
| Glu | −1 | 0 | 0 | 2 | −4 | 2 | 5 | | | | | | | | | | | | | |
| Gly | 0 | −2 | 0 | −1 | −3 | −2 | −2 | 6 | | | | | | | | | | | | |
| His | −2 | 0 | 1 | −1 | −3 | 0 | 0 | −2 | 8 | | | | | | | | | | | |
| Ile | −1 | −3 | −3 | −3 | −1 | −3 | −3 | −4 | −3 | 4 | | | | | | | | | | |
| Leu | −1 | −2 | −3 | −4 | −1 | −2 | −3 | −4 | −3 | 2 | 4 | | | | | | | | | |
| Lys | −1 | 2 | 0 | −1 | −3 | 1 | 1 | −2 | −1 | −3 | −2 | 5 | | | | | | | | |
| Met | −1 | −1 | −2 | −3 | −1 | 0 | −2 | −3 | −2 | 1 | 2 | −1 | 5 | | | | | | | |
| Phe | −2 | −3 | −3 | −3 | −2 | −3 | −3 | −3 | −1 | 0 | 0 | −3 | 0 | 6 | | | | | | |
| Pro | −1 | −2 | −2 | −1 | −3 | −1 | −1 | −2 | −2 | −3 | −3 | −1 | −2 | −4 | 7 | | | | | |
| Ser | 1 | −1 | 1 | 0 | −1 | 0 | 0 | 0 | −1 | −2 | −2 | 0 | −1 | −2 | −1 | 4 | | | | |
| Thr | 0 | −1 | 0 | −1 | −1 | −1 | −1 | −2 | −2 | −1 | −1 | −1 | −1 | −2 | −1 | 1 | 5 | | | |
| Trp | −3 | −3 | −4 | −4 | −2 | −2 | −3 | −2 | −2 | −3 | −2 | −3 | −1 | 1 | −4 | −3 | −2 | 11 | | |
| Tyr | −2 | −2 | −2 | −3 | −2 | −1 | −2 | −3 | 2 | −1 | −1 | −2 | −1 | 3 | −3 | −2 | −2 | 2 | 7 | |
| Val | 0 | −3 | −3 | −3 | −1 | −2 | −2 | −3 | −3 | 3 | 1 | −2 | 1 | −1 | −2 | −2 | 0 | −3 | −1 | 4 |

For example, additional established algorithms available may be used to align and determine the similarity of two or more amino acid sequences. The "FASTA" similarity search algorithm of Pearson and Lipman is a suitable protein alignment method for examining the level of identity shared by two or more amino acid sequences (see e.g. Pearson and Lipman, Proc. Natl. Acad. Sci. USA & 5:2444 (1988), and by Pearson, Meth. Enzymol. 183:63 (1990)). Briefly, FASTA first characterizes sequence similarity by identifying regions shared by the query sequence and a test sequence that have either the highest density of identities (if the ktup variable is 1) or pairs of identities (if ktup=2), without considering conservative amino acid substitutions, insertions, or deletions. The ten regions with the highest density of identities are then re-scored by comparing the similarity optionally coupled to or comprise a further label. The further label used in the inventive method may e.g. be a radioisotope, or a fluorescent label. The term "fluorescent label", "fluorescent dye", or "fluorophore" as used for the inventive further label are as defined above, the term radioisotope refers to any of radioisotope e.g. $^{14}C$, $^{3}H$, $^{32}P$, $^{125}I$, $^{131}I$, or $^{125}I$, which may be used in the inventive method to detect the protein of interest.

According to one embodiment the inventive method comprises selecting the host cells of step (d) of the inventive method as disclosed above. Accordingly, the inventive method comprise selecting host cells as disclosed above, which display on their surface the protein of interest. The term "selecting" as used within the inventive method refers to the process of identifying and/or isolating cells which display on their surface the protein of interest non-covalently bound to an inventive second label and which have been detected by means as disclosed above and separating the host cells from host cells, which e.g. do not display the protein of interest on their surface. Selection in the inventive method may comprise various technologies known to the skilled person, such as e.g. immuno-panning (see e.g. Wysocki et al. Proc. Nati. Acad. Sci. USA Vol. 75, No. 6, pp. 2844-2848, June 1978), magnetic-activated cell sorting (MACS), flow-cytometry, fluorescence-activated cell sorting (FACS), or droplet-based microfluidics (see e.g. Mazutis et al., 2013, Nature Protocols 8, 870-891). The selected cells of the invention may as part of the selection e.g. be separated and isolated from host cells that do not display the protein of interest on their surface by the methods as disclosed above. For example, FACS may be used to sort cells into different vials or containers, or MACS may be used to separate host cells that display the protein on their surface, or droplet-based microfluidics may be used to select and isolate host cells according to the invention which display the protein of interest on their surface.

In one embodiment, the inventive method may be used the select cells, which display proteins of altered phenotype. Accordingly, the selection of host cells by the inventive method may be used to select host cells, which express e.g. the protein of interest of altered phenotype, or at least a protein of interest of altered phenotype. The term "altered phenotype" as used with the inventive method refers to one or more altered properties of the protein of interest, or the at least one protein of interest displayed on the surface of the host cell according to the invention.

According to one embodiment, the altered phenotype of the protein of interest displayed on host cells according to the invention may be one of surface expression level, protein stability, protein folding, or affinity. Accordingly, the inventive method may e.g. be used to select host cells which display increased amounts of the protein of interest compared to a reference population of host cells, which do not express the protein, or the at least one protein of interest. For example, the inventive method may be used to select host cells that harbor polynucleotides which encode signal peptides that more efficiently direct the protein of interest to the secretory pathway of a cell, or to select for polynucleotides in which regulatory sequences have been altered (e.g. mutated) and result in increased expression of the protein of interest. It will be apparent to the skilled person that the inventive method and selection as disclosed above may be reiterated for example at least once, or 2, 3, 4, 5, 6, 7, 8, 9, or 10 times to select or enrich for host cells which display increased amounts of the protein of interest. The selected cells may then, e.g. be used to isolate the polynucleotides contained therein and to subsequently subject said polynucleotides to sequencing.

DNA isolation and sequencing may be done according to standard protocols known in the art such as those disclosed in "Molecular Cloning", 4$^{th}$ edition, CSHL Press. For example, the polynucleotides (e.g. plasmids) in the selected host cells according to the invention may also be done using commercially available kits, such as e.g. Qiagen's DNeasy Blood and Tissue kit, or e.g. MasterPure™ Yeast DNA Purification Kit (Epicenter).

For instance, the inventive method may also be employed to examine the effects of mutating the inventive second label to evaluate the effects of a mutation, or of at least one or more mutations on the non-covalent binding of the protein of interest, e.g. the effects of non-conservative amino acid exchanges within the second label on the non-covalent binding of the protein of interest may be examined. For example, decreased surface expression of a protein of interest may be the result of decreased binding of the protein of interest to the inventive second label compared to a reference sample in which the second label has not been modified. A reference sample, for example, may comprise at least one, preferably e.g. at least 10, 100, $10^3$, $10^4$, $10^5$, or $10^6$ host cell displaying the protein of interest on the surface of said host cells by means of the inventive method prior to any manipulations, e.g. prior to one or more amino acid exchanges (conservative, or non-conservative), addition of amino acid sequences, e.g. N-linked glycosylation signal, or e.g. affinity maturation. Thus, the reference sample may, e.g. comprise host cells, or be comprised of host cells, which do not fall within the FACS selection parameters (gates), and are comprised within the sample to be analyzed.

Thus, the inventive method may e.g. be used to engineer and select the inventive second label and to select for second label species of increased or increased binding affinity to the protein of interest. Preferably, the inventive method may e.g. be used to select for inventive second labels which display increased binding to the protein of interest.

For example, the inventive method as disclosed above may also be used to select host cells which display the protein of interest, or at least one protein of interest of altered phenotype, whereby the altered phenotype is protein stability. In the inventive method the term "protein stability" is used in a structural context, i.e. relating to the structural integrity of a protein, or in a functional context, i.e. relating to a protein's ability to retain its function and/or activity over time. Accordingly, the inventive method may be used to select host cells as disclosed above which display on their surface as disclosed above the protein of interest of increased or decreased protein stability. Increased or decreased protein stability may for example be determined by antibodies which recognize or specifically bind to conformation-sensitive epitopes on the protein of interest. For example, protein stability may also be assessed by e.g. quantitative detection of the protein of interest displayed on the surface of the host cell according to the inventive method through the use of fluorescently labeled antibodies, e.g. antibodies as disclosed above which may be linked or coupled to one or more fluorophores as disclosed above may be used to detect the protein of interest (POI) on the surface of the host cell. This way, the host cells may then e.g. subjected to FACS analysis to assess changes in the overall fluorescent signal compared to a reference sample.

In one embodiment the inventive method may be used to select host cells in which the altered phenotype is affinity. For example, the inventive method may be used to select a POI (e.g. an antibody or antibody fragment as disclosed above) with increased or decreased affinity for a target protein or epitope. Accordingly, the inventive method may be used to select e.g. antibodies with increased affinity for an epitope, whereby the inventive method may be reiterated to select antibodies of increasing affinity for an epitope, whereby the plasmids encoding the antibody, or antibody fragment, such as fragments comprising complementarity determining regions (CDRs), e.g. CDR1, CDR2 or CDR3, of e.g. the light and/or heavy chains, may be used. i.e. the inventive method may be used in affinity maturation of an antibody or antibody fragment as disclosed above. As used in for the inventive method the term "affinity maturation" shall refer to a process of successive mutation and selection by which antibodies of higher affinity are selected. The term "affinity" or "binding affinity", as used with the inventive method, includes the strength of a binding interaction and therefore includes both the actual binding affinity as well as the apparent binding affinity. The actual binding affinity is a ratio of the association rate over the disassociation rate. Therefore, conferring or optimizing binding affinity includes altering either or both of these components to achieve the desired level of binding affinity. The apparent affinity can include, for example, the avidity of the interaction. For example, a bivalent altered variable region binding fragment can exhibit altered or optimized binding affinity due to its valency.

For example, so called "variant libraries" may also be used in the inventive method and host cells may be selected which display e.g. a CDR of desired affinity for a given epitope and may be selected by the inventive method. Variant libraries typically include in silico amino acid sequence libraries derived from the combinatorial enumeration of the variant profile of the hit library. A Hit variant library in turn is an amino acid sequence library that is expressed in vitro by a degenerate oligonucleotide library for functional screening. Hit variant libraries expand the sequence space of other hit variant libraries due to back translation, optimized codon usage, recombination at the nucleotide level and expression of the resulting combinatorial nucleic acid library.

In one embodiment the inventive method as disclosed above may be used to select for antibodies with increased affinity for an epitope by using variant libraries comprising sequence variant light chain CDR sequences in combination with sequence-invariant polynucleotides encoding e.g. sequence-invariant $V_H$ sequences, e.g. encoding sequence-invariant $V_H$ CDR1, CDR2, CDR3 and FR (e.g. FR1, FR2, FR3 and FR4) sequences, e.g. encoding a $V_H$ of predetermined affinity to a protein of interest. For example, the $V_L$ variant libraries may comprise sequence variants of any one of the light chain CDRs, e.g. CDR1, CDR2, CDR3, or $V_L$ variant libraries, in which the framework sequences (FR) are fixed and the polynucleotides encoding the $V_L$ CDR1, CDR2, CDR3 are variable in their sequence, e.g. the variant library encodes $V_L$ FR1-CDR1-FR2-CDR2-FR3-CDR3-FR4 with variable CDR1, CDR2 and CDR3 polynucleotide sequences. The variant library encoding $V_L$ FR1-CDR1-FR2-CDR2-FR3-CDR3-FR4 may e.g. also be sequence variant in any of the framework sequences FR1, FR2, FR3, or FR4, or e.g. in both CDR and FR sequences, e.g. sequence variant in at least one, two, three, four, or five, six, or all of FR1, CDR1, FR2, CDR2, FR3, CDR3, FR4. Sequence libraries which may e.g. be used in the inventive method in addition to those disclosed above, may include libraries generated by PCR-based techniques, such as those described in Proc. Natl. Acad. Sci. USA Vol. 86, pp. 3833-3837, May 1989; Science (1989) 246(4935):1275-1281, or Nucleic Acids Research, 2005, Vol. 33, No. 9 e81, whereby the sequence variant libraries as described above are comprised in suitable expression vectors, e.g. expression vectors that are suitable for expression of $V_L$, or $V_H$ in yeast, such as e.g. those disclosed herein, or e.g. pESC-LEU, pESC-leu2d, p4X3, p4X4, p4X5, p4X6, or e.g. those described in Yeast 1993 December; 9(12):1309-18. For example, the inventive method may be applied at least once, twice, three, four, five or six times to select for proteins of interest, such as e.g. antibodies with desired properties, e.g. to select for yeast cell clones which display antibodies with $V_L$ and $V_H$ chains of desired affinity to an antigen or epitope of interest. For example, the inventive method may also be used for affinity maturation of any one of the heavy chain CDRs through the use of $V_H$ CDR sequence variant libraries by the inventive method as disclosed above, e.g. $V_H$ FR1-CDR1-FR2-CDR2-FR3-CDR3-FR4 sequence variant libraries in combination with sequence-invariant polynucleotides encoding a $V_L$ chain may be used in affinity maturation. The variant library encoding $V_H$ FR1-CDR1-FR2-CDR2-FR3-CDR3-FR4 may e.g. be sequence variant in any of the framework sequences FR1, FR2, FR3, or FR4, or e.g. in both CDR and FR sequences, e.g. sequence variant in at least one, two, three, four, or five, six, or all of FR1, CDR1, FR2, CDR2, FR3, CDR3, FR4.

In one embodiment, the selection step of the inventive method further comprises comparing the selected host cells to a reference sample. Accordingly, the selection step of the inventive method comprises comparing the phenotype of a POI selected by the inventive method to the same phenotype of a reference host cell which displays the POI of unaltered phenotype. For example, the binding affinities of antibodies or antibody fragments displayed on the surface of host cells as disclosed above which were subjected to at least one round of affinity maturation may e.g. be compared to the affinity of the respective antibodies prior to affinity maturation. Other examples may include comparing the fluorescent intensity of host cells which have been selected by the inventive method as disclosed above to a reference sample in which the host cells have not been selected by the inventive method. For example, using FACS analysis host cells selected by the inventive method may be compared to a reference sample, or e.g. within a typical FACS analysis the host cells which do not fall within the selection criteria set for the FACS analysis, may serve as a reference sample.

According to one embodiment, the protein of interest encoded by the at least one or more polynucleotides of step (a) of the inventive method comprise at least one Fc-domain, or Fc-domain homodimer as disclosed above. Accordingly, the protein of interest of the present invention may e.g. comprise at least one Fc domain as disclosed above, or at least two Fc-domains as disclosed above, or e.g. 3, 4, 5, or 6 Fc domains.

According to a preferred embodiment, the Fc domains of the inventive protein of interest are one of human IgG1, human IgG2, murine IgG2a, murine IgG2b, or murine IgG3; or sequence variants thereof. Accordingly, the inventive POI may comprise at least one, e.g. 1, 2, 3, 4, 5, or 6, human IgG1 Fc domain, or e.g. human IgG2 Fc domain, or murine IgG2a Fc domain, or murine IgG2b Fc domain, or murine IgG3 Fc domain, or sequence variants thereof as disclosed above. Fc domain sequence variants of the inventive POI may further comprise one or more conservative or non-conservative amino acid substitutions as defined above, which preferably do not reduce binding of the Fc domain to the inventive second label. In one aspect the protein of interest according to the invention may be a N-terminal Fc-domain fusion protein, C-terminal Fc-domain fusion protein or an antibody, preferably the protein of interest in the inventive method is a monoclonal antibody as disclosed above.

According to a preferred embodiment, the protein of interest of the invention is a monoclonal antibody, which may be a murine monoclonal antibody, mouse-human chimeric monoclonal antibody, humanized monoclonal antibody, or human monoclonal antibody. The term "chimeric antibody" as used with or for the inventive method includes monovalent, divalent or polyvalent immunoglobulins. A monovalent chimeric antibody may e.g. be a dimer (HL) formed by a chimeric H chain associated through disulfide bridges with a chimeric L chain, or e.g. divalent chimeric antibody is tetramer (H2 L2) formed by two HL dimers associated through at least one disulfide bridge. For example, a polyvalent chimeric antibody may also be obtained by employing a CH region that aggregates (e.g., from an IgM H chain). Murine and chimeric antibodies, fragments and regions of the present invention may comprise individual heavy (H) and/or light (L) immunoglobulin chains. For example, a chimeric H chain may comprises an antigen binding region derived from the H chain of a non-human antibody specific for the protein of interest, which is linked to at least a portion of a human H chain C region (CH), such as CH1 or CH2. A chimeric L chain according to the present invention, comprises an antigen binding region derived from the L chain of a non-human antibody specific for the protein of interest, linked to at least a portion of a human L chain C region (CL).

For example, antibodies, fragments or derivatives of the present invention having chimeric H chains and L chains of the same or different variable region binding specificity, may also be prepared by appropriate association of the individual polypeptide chains, according to known method steps (see e.g. Harlow and Lane, Antibodies: A Laboratory Manual, Cold Spring Harbor Laboratory Press (1988)) Chimeric antibodies may be constructed by recombinant DNA technology, and are described e.g. in Shaw, et al., J. Immun., 138:4534 (1987), Sun, L. K, et al., Proc. Natl. Acad. Sci. USA, 84:214-218 (1987); Waldmann (1991), Science 252: 1657.

In one aspect the protein of interest of the present invention is a humanized antibody, whereby the term "humanized antibody" as used includes antibodies in which CDR sequences derived from the germline of another mammalian species, such as e.g. mouse, rabbit, or rat, have been grafted onto human framework sequences. Additional framework region modifications may be made within the human framework sequences as well as within the CDR sequences derived from the germline of another mammalian species. The humanized antibody of the present invention may be in any antibody form, e.g. such as those disclosed above. In some embodiments, they are intact immunoglobulin molecules (full-length antibodies), including IgG, IgA, IgD, IgE, and IgM, Fab, F(ab')2, Fv, minibody, or a diabody. For example, humanized antibodies which may be used in the inventive method may also obtained by e.g. from B cells of transgenic animals, which use human germline immunoglobulin genes (see e.g. Macdonald et al. (2014) Proc Natl Acad Sci USA. April 8; 111(14):5147-52).

The protein of interest of the present invention may also e.g. be a human antibody, whereby the term "human antibody" includes antibodies having variable regions in which both the framework and CDR regions are derived from human germline immunoglobulin sequences. If the human antibody contains a constant region, the constant region also is derived from human germline immunoglobulin sequences. The human antibodies of the invention may include amino acid residues not encoded by human germline immunoglobulin sequences (e.g. mutations introduced by random or site-specific mutagenesis in vitro or by somatic mutation in vivo). However, the term "human antibody" as used in the present invention is not intended to include antibodies in which CDR sequences derived from the germline of another mammalian species, such as e.g. mouse, rat or rabbit, which have been grafted onto human framework sequences. Human antibodies or polynucleotides encoding the same may e.g. obtained from transgenic mice carrying parts of the human immune system instead of the mouse immune system. For example, polynucleotide sequences encoding fully human monoclonal antibodies may be used in the inventive method may be prepared by immunizing mice transgenic for large portions of human immunoglobulin heavy and light chain loci (see e.g. U.S. Pat. No. 6,150,584). Polynucleotides encoding humanized antibodies may be e.g. obtained by standard methods known in the art.

According to one embodiment, the second label of the present invention specifically binds Fc domains of human IgG1, human IgG2, murine IgG2a, murine IgG2b, or murine IgG3. The terms "specifically bind" and "specific binding", as used throughout the present invention and for the inventive second label, generally refers to the ability of a binding domain, such as e.g. the inventive second label, or an antibody as disclosed herein, to preferentially bind to a particular protein, protein fragment, polypeptide, or antigen that is present in a homogeneous mixture of different proteins, protein fragments, peptides, or antigens. Typically, the specific binding interaction will discriminate between desirable and undesirable proteins, protein fragments, peptides, or antigens in a sample by more than $10^7$, $10^8$, $10^9$, $5\times10^9$, or $10^{10}$, e.g. specific binding may include binding affinities of from at least about $10^{-7}$ M to at least about $10^{-12}$ M, or e.g. at least of $1\times10^{-7}$M, $2.5\times10^{-7}$ M, $5\times10^7$M, $7.5\times10^{-7}$M, $10^{-8}$ M, $2.5\times10^{-8}$ M, $5\times10^{-8}$ M, $7.5\times10^{-8}$ M, $10^{-9}$ M, $2.5\times10^{-9}$ M, $5\times10^{-9}$ M, $7.5\times10^{-9}$ M, $10^{-10}$ M, $2.5\times10^{-10}$ M, $5\times10^{-10}$ M, $7.5\times10^{-10}$ M, $10^{-11}$ M, $2.5\times10^{-11}$M, $5\times10^{-11}$ M, $7.5\times10^{-11}$ M, or $10^{-12}$ M. For example, the second label may comprise protein A, protein L, protein G, protein A-G fusion, domains E, D, A, B of protein A, or fragments thereof, which bind to Fc domains of human IgG1, human IgG2, murine IgG2a, murine IgG2b, or murine IgG3.

In addition to the proteins provided above which specifically bind Fc domains as disclosed above, proteins such as e.g. immunoglobulin new antigen receptor (IgNARs), Hcab, anticalins (see e.g. Beste et al., Proc. Natl. Acad. Sci. USA Vol. 96, pp. 1898-1903, March 1999), cystine knot miniproteins/knottins (see e.g. Kolmar, FEBS J. 2008 June; 275(11):2684-90), affibodies (see e.g. Nord et al. Nat Biotechnol. 1997 August; 15(8):772-7), aptamers, DARPins (see e.g. Binz et al. (2003) J. Mol. Biol. 332, 489-503), or affilins (see e.g. Ebersbach et al. (2007) J. Mol. Biol. 372, 172-185) may be used in the inventive method to specifically bind antibodies as defined herein, or proteins of interest which may comprise an Fc domain, or which may be devoid of an Fc domain.

For example, the immunoglobulin new antigen receptor (IgNAR) may be used in the present invention as a second label or e.g. be comprised in a second label according to the invention. IgNAR are derived from cartilaginous fishes (for example sharks) and are heavy-chain antibodies. IgNARs show significant structural differences to other antibodies, in that they comprise five constant domains (CH) per chain instead of the usual three, several disulfide bonds in unusual positions, and the complementarity determining region 3 (CDR3) forms an extended loop covering the site which binds to a light chain in other antibodies (see e.g. Barelle et al., (2009) Adv Exp Med Biol. 655:49-62).

For example, the term "Hcabs" as used in the inventive method, refers to antibodies found in antibodies from species of *Camelidae* (i.e. *Camelus dromedarius, Camelus bactrianus, Lama glama, Lama guanoco, Lama alpaca* and *Lama vicugna*) which lack their L-chain (see e.g. Muyldermans et al. (2009) Veterinary Immunology and Immunopathology 128, 178-183). The H-chain within the HCAbs is composed of three instead of four globular domains and the two constant domains are highly homologous to the Fc domains (CH2-CH3) of classical antibodies. The domain corresponding to the CH1 domain of classical antibodies is missing in HCAbs. Hence, the antigen binding fragment of a classical antibody, the Fab, is reduced to a single variable domain in the HCAb. This variable domain referred to as VHH is adapted to become functional in antigen binding in absence of a variable light (VL) chain domain.

In a preferred embodiment, the second label of the present invention comprises amino acid sequence according to SEQ ID NO: 1 and/or the amino acid sequence according to SEQ ID NO 2. Accordingly, the second label according to the invention may comprise the amino acid sequence according to SEQ ID NO: 1, or the amino sequence according to SEQ ID NO: 2, or the amino acid sequence according to both SEQ ID No: 1 and SEQ ID NO: 2. The inventive second label may also comprise sequence variants of each or of both SEQ ID NO: 1 or SEQ ID NO: 2, e.g. sequence variants may comprise conservative and non-conservative amino acid substitutions as defined above. Preferably, the amino acid substitutions do not result in a loss of specific binding of the second label to the protein of interest, e.g. the binding affinity should not be greater than of $1 \times 10^{-7}$ M, $2.5 \times 10^{-7}$ M, $5 \times 10^7$ M, $7.5 \times 10^{-7}$ M, $10^{-8}$ M, $2.5 \times 10^{-8}$ M, $5 \times 10^{-8}$ M. The sequence variants of the inventive label comprising SEQ ID NO:1, SEQ ID NO: 2 or both amino acid sequences are at least 80%, 85%, 90%, 95%, or 98%, or from about 92% to about 98%, e.g. 92%, 93%, 94%, 95%, 96%, 97%, or 98% identical to SEQ ID NO: 1 and/or SEQ ID NO: 2, whereby the sequence similarity may be calculated as described above. The sequence similarity may be calculated over the entire length of the amino acid sequences of SEQ ID NO: 1 and/or SEQ ID NO: 2, but may also be calculated over any part or position of the amino acid sequences SEQ ID NO1 and/or SEQ ID NO:2 of 10-100 amino acids, or 20-90 amino acids, 30-80 amino acids, 40-70 amino acids, 50-60 amino acids in length, e.g. of about 15-55 amino acids in lengths, or of about 25-115 amino acids in length, or of about 35-95 amino acids in length, or of about 45-85 amino acids in length, or of about 12, 13, 14, 15, 16, 17, 18, 19, 20, 21, 22, 23, 24, 25, 26, 27, 28, 29, 30, 32, 34, 35, 36, 37, 38, 39, 40, 42, 46, 48, 51, 54, 56, 57, 59, or 60 amino acids in length.

According to a preferred embodiment, the inventive second label comprises the amino acid sequence according to SEQ ID NO: 3. Accordingly the inventive second label comprises the amino acid sequence according to SEQ ID NO: 6 in which the signal peptide according to SEQ ID NO: 4 has been removed. The inventive second label may also comprise sequence variants, which are at least 80%, 85%, 90%, 95%, or 98% identical to SEQ ID NO: 3, whereby %-identity may be calculated as disclosed above, e.g. over the entire amino acid sequence of SEQ ID NO: 3, or e.g. over any part and length of the amino acid sequence according to SEQ ID NO: 3 as disclosed above.

In one aspect of the present invention, the second label as disclosed above, e.g. the second label according to SEQ ID NO: 3 may further be modified to comprise one or more amino acid sequences that direct N-linked glycosylation (glycosylation consensus sequence). For example, the inventive second label may be modified to comprise the amino acid sequence N-x-S/T, whereby x may be any amino acid except proline. The glycosylation consensus sequence as disclosed may be added to the amino-terminus, or carboxy-terminnus or embedded into the amino acid sequence of the inventive second label according to SEQ ID NO: 3, whereby the glycosylation consensus sequence may e.g. be inserted between protein domains, e.g. between SEQ ID NO: 1 and SEQ ID NO: 2. Including a glycosylation consensus sequence into the inventive second label may e.g. be useful to increase expression levels of the inventive second label in the host cells, either co-expressed with the protein of interest, or e.g. expressed by suitable cells to obtain sufficient amounts of the inventive label for purification and subsequent use in the inventive method. The inventive second label may, e.g. also comprise amino acid sequences separating its individual domains (e.g. "spacer"), such as e.g. those disclosed in WO 2014/101287.

In a preferred embodiment, the isolation and/or detection step of the inventive method further comprises the steps of:
 (i) contacting a host cell with a detectably labeled antibody or antibody fragment, which specifically binds to Fc domains of human IgG1, human IgG2, murine IgG2a, murine IgG2b, or murine IgG3; or sequence variants thereof,
 (ii) contacting the host cell with an antigen and/or epitope specifically bound by the antibody bound to the second label, which is coupled to a further detectable label distinct from the label used in (i);
 (iii) detecting the labels of (i) and/or (ii) on said host cells.
 (iv) selecting host cells that display altered amounts of the label used in (i), and/or the label used in (ii) and/or display altered amounts of both labels compared to a reference sample.

The term "detectable" or "detectably" as used in the inventive method refers to a molecule or particle able to be detected, including, but not limited to, fluorescence, chemiluminescence, radiation, e.g. fluorescent labels include those as disclosed above.

For example, the isolation and/or detection step of the inventive method as disclosed above may also be carried out by contacting a host cell with a detectably labeled antibody or antibody fragment, which specifically binds to the light chain of human IgG1, human IgG2, human IgG3, human IgG4, murine IgG2a, murine IgG2b, or murine IgG3; or sequence variants thereof, e.g. to human kappa or lambda light chains, murine kappa or lambda light chains, or e.g. to IgG F(ab')2 fragments of any of human IgG1, IgG2, murine IgG2a, IgG2b, or IgG3. For example, antibodies which specifically bind to human light chain epitopes may e.g. include those described in Clin Immunol Immunopathol. 1991 April; 59(1):139-55. For example, the isolation and/or detection step of the inventive method may comprise the steps of:
 (i) contacting a host cell with a detectably labeled antibody or antibody fragment, which specifically binds to light chains (e.g. human kappa or lambda light chains) of human IgG1, human IgG2, human IgG3, human IgG4, murine IgG2a, murine IgG2b, or murine IgG3; or sequence variants thereof,
 (ii) contacting the host cell with an antigen and/or epitope specifically bound by the antibody bound to the second label, which is coupled to a further detectable label distinct from the label used in (i);
 (iii) detecting the labels of (i) and/or (ii) on said host cells.
 (iv) selecting host cells that display altered amounts of the label used in (i), and/or the label used in (ii) and/or display altered amounts of both labels compared to a reference sample.

According to a preferred embodiment, the detection and/or selection of the labels used in steps (i) and (ii) and the selection of the host cells in step (iv) of the inventive method comprise flow cytometry and/or FACS and/or microfluidics as disclosed above.

In one embodiment, the inventive method as disclosed above may be reiterated. For example, host cells which have been selected through the use of the inventive method as disclosed above, may be subjected to e.g. at least 1, 2, 3, 4, 5, 6, 7, 8, 9, or 10 round of selection by the inventive method as disclosed above. The host cells selected by the inventive method may, e.g. also be used to isolate the polynucleotides therefrom and to subject the isolated nucleotides to e.g. sequencing, PCR amplification, PCR-based mutagenesis.

PCR amplification as used in the context of the present invention refers to a method whereby virtually any target DNA sequence can be selectively amplified. The method uses forward and reverse sequence-specific probe pairs, specific for regions which flank a target DNA sequence which hybridize to opposite strands of target DNA and define the limits of the sequence to be amplified. The specifically designed oligonucleotides initiate multiple sequential rounds of DNA synthesis catalyzed by a thermostable DNA polymerase, such as *Thermus aquaticus* (Taq) polymerase or *Thermococcus litoralis* (Vent™, New England Biolabs) polymerase or Tthl polymerase (Perkin-Elmer). Each round of synthesis is typically separated by a melting and re-annealing step, allowing a given DNA sequence to be amplified several hundred-fold in less than an hour. Methods for PCR amplification are described in the art (see e.g. PCR Technology: Principles and Applications for DNA Amplification ed. H A Erlich, Stockton Press, New York, N.Y. (1989); PCR Protocols: A Guide to Methods and Applications, eds. Innis, Gelfland, Snisky, and White, Academic Press, San Diego, Calif. (1990); Mattila et al. (1991) Nucleic Acids Res. 19: 4967). PCR may also be used in the present invention for affinity maturation of the POI, e.g. if the POI is an antibody or antibody fragment (e.g. CDR1, CDR2, or CDR3) of an antibody fused or linked to an antibody framework (see e.g. Gram et al, Proc Natl Acad Sci USA. 1992 Apr. 15; 89(8):3576-80).

In one embodiment, the host cell of the inventive method is a yeast cell and wherein step (a) of the inventive method further comprises mating of at least a first and second yeast cell whereby said first and second host cells comprise different polynucleotides of which at least one encodes a Fc domain-containing fusion protein and whereby said polynucleotides of said first and second host cell comprise at least one distinct selectable marker. Mating of the yeast cells in the inventive method may be done according to standard protocols in the art, e.g. according to the method as disclosed in Weaver-Feldhaus et al. (2004) FEBS Letters 564, 24-34, or e.g. as disclosed by Baek et al., J. Microbiol. Biotechnol. (2014), 24(3), 408-420. Accordingly, in one aspect of the inventive method a first yeast cell or cells may harbor a heavy chain library, and a second host cell may harbor the light chain library, whereby both host cells, or polynucleotides of the heavy and light chain comprise distinct selectable markers.

For example, mating of the yeast cells in the inventive method may be done as follows: The heavy chain library may be constructed and displayed in JAR300 yeast cells, which have the following auxotrophic markers, ura3-52, trp1, leu2N200, his3N200, pep4:HIS3, prbd1.6R, can1, and GAL; the strain is based on EBY100 that was derived from BJ5465 and is MATa. The KanMU4 gene, conferring resistance to G418, may e.g. be inserted through homologous recombination of a polymerase chain reaction (PCR) product encoding the KanMU4 gene flanked by 45 bp of the URA3 gene. The light chain Fab may be e.g. expressed in YVH10 cells, which are (Ura3, Trp3, BJ5464, MAT-alpha). The mating conditions may e.g. be as follows: Fresh cultures of YVH10/pPNL30-LC (MATK strain) and JAR300/pPNL20-HC (MAT "a" strain) may be grown in the selectable media, e.g. SDCAA+tryptophan or SDCAA+uracil. 1 OD600/ml (2U107 yeast) of each culture may e.g. be mixed together, pelleted, and resuspend in 200 WI YPD, before placing in the center of a prewarmed 30° C. YPD plate without subsequent spreading. The plates may then e.g. be incubated at 30° C. for about 4-6 h. The yeast spots may then be resuspended in SDCAA medium. Appropriate dilutions may be plated based on 10% diploid formation and plated on SDCAA agar plate or may be grown in liquid SDCAA medium at 30° C. with agitation. The OD600 reading at the start of growth is for example preferably below 0.1 OD600/ml to allow growth of the diploids to outcompete the non-growing haploids. For Fab library generation, larger numbers of yeast may be used and the volumes may be adjusted accordingly.

In one embodiment, the present invention provides for an isolated nucleic acid according to SEQ ID NO:5. The term "isolated" as used for the nucleic acid of the invention refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined, for example, by agarose electrophoresis, or e.g. by determining the ratio $OD_{260}/OD_{280}$. An isolated nucleic acid sequence can be obtained by standard cloning procedures used in genetic engineering to relocate the nucleic acid sequence from its natural location to a different site where it will be reproduced. The cloning procedures may e.g. involve excision and isolation of a desired nucleic acid fragment comprising the nucleic acid sequence encoding the polypeptide, insertion of the fragment into a vector molecule, or plasmid, which may be collectively referred to herein as "constructs," "plasmids," or "vectors.", and incorporation of the recombinant vector into a host cell where multiple copies or clones of the nucleic acid sequence will be replicated. The nucleic acid sequence may be of genomic, cDNA, RNA, semisynthetic, or synthetic origin, or any combinations thereof.

The term covers, for example, (a) a DNA which has the sequence of part of a naturally occurring genomic molecule but is not flanked by at least one of the coding sequences that flank that part of the molecule in the genome of the species in which it naturally occurs; (b) a nucleic acid incorporated into a vector or into the genomic nucleic acid of a prokaryote or eukaryote in a manner such that the resulting molecule is not identical to any vector or naturally occurring genomic DNA; (c) a separate molecule such as a cDNA, a genomic fragment, a fragment produced by polymerase chain reaction (PCR), ligase chain reaction (LCR) or chemical synthesis, or a restriction fragment; (d) a recombinant nucleotide sequence that is part of a hybrid gene, i.e., a gene encoding a fusion protein, and (e) a recombinant nucleotide sequence that is part of a hybrid sequence that is not naturally occurring. The term "nucleic acid" as used in the present invention further includes modified or derivatized nucleotides and nucleosides such as, but not limited to, halogenated nucleotides such as, but not only, 5-bromouracil, and derivatized nucleotides such as biotin-labeled nucleotides.

In one aspect the present invention also provides isolated nucleic acid molecules which under stringent conditions hybridize to the nucleic acid molecule according to SEQ ID NO: 4. The term "stringent conditions" as used for any isolated nucleic acid of the invention refers to parameters known in the art, e.g. stringent conditions, as used herein, refer to hybridization in 3.5×SSC, 1×Denhardt's solution, 25 mM sodium phosphate buffer (pH 7.0), 0.5% SDS, and 2 mM EDTA for 18 hours at 65° C. This is followed by four washes of the filter, at 65° C. for 20 minutes, in 2×SSC, 0.1% SDS, and one wash for up to 20 minutes in 0.3×SSC, 0.1%

SDS. There are other conditions, reagents, and so forth which can be used, which result in the same degree of stringency.

In one embodiment the present invention provides for an isolated protein encoded by the nucleic acid sequence according to SEQ ID NO: 5, in which the amino acid sequence according to SEQ ID NO. 4. Accordingly, the protein provided by the present invention comprises the amino acid sequence according to SEQ ID NO: 3. The term "isolated protein" as used for the inventive protein refers to a protein essentially free of other cellular components, such as e.g. lipids, DNA, RNA and cellular proteins. Accordingly the inventive protein is at said to be essentially free of cellular components if the inventive protein is at least 60%, or at least 70%, or at least 80%, preferably at least 90%, 95% pure; for example, the term isolated protein may also refer to a protein produced by expression of an isolated nucleic acid molecule in a suitable host cell.

In one embodiment, the present invention provides a host cell which comprises at least one nucleic acid molecule comprising the nucleic acid sequence according to SEQ ID NO: 5, or a nucleic acid which under stringent conditions hybridizes to the nucleic acid sequence of SEQ ID NO: 5. Accordingly, the present invention provides for a host cell as disclosed above, which comprises at least one nucleic acid molecule comprising the nucleic acid sequence of SEQ ID NO: 5. For example, the host cell according to the invention may comprise a vector, or plasmid which is suited to allow the expression of the nucleotide sequence according to SEQ ID NO: 5 in that host cell. The exact expression vector used for directing the expression of the inventive nucleic acid according to SEQ ID NO: 5 may depend on the host cell, but may include e.g. pCMV, pcDNA, p4X3, p4X4, p4X5, p4X6, pVL1392, pVL1393, pACYC177, PRS420, or if viral based vector systems may be used e.g. pBABEpuro, pWPXL, pXP-derived vectors.

In one embodiment, the present invention provides for a process of producing a protein by culturing a host cell which comprises a nucleic acid molecule, which may e.g. comprise the nucleic acid sequence according SEQ ID NO: 5, culturing said host cells under conditions that are sufficient for protein expression, expressing the protein encoded by the nucleic acid sequence according to SEQ ID NO: 5 and isolating and purifying the protein encoded by SEQ ID NO: 5. For example, methods as disclosed above may be employed for introducing the nucleic acid molecule comprising SEQ ID NO: 5 may be done by any known technology in the art, such as lipofection, electroporation, Ca-phosphate transfection, viral transduction. The cells may then be grown under conditions that are sufficient for protein expression. For example, mammalian cells comprising at least one nucleic acid molecule comprising SEQ ID NO: 3 may be allowed to grow in DMEM containing 10% FBS, and were incubated at 37° C. in 10% $CO_2$, or e.g. in protein-free culture medium to aid in the subsequent isolation and purification, or e.g. in Grace's insect medium, express Five® SFM (Life Technologies), or High Five® medium (Life Technologies), YNM medium, YPD broth, or e.g. PichiaPink (Life technologies).

The cells may e.g. be allowed to grow between 12-408 h, e.g. for about 12 to about 400 h post plating, e.g. between 14 h, 16 h, 18 h, 20 h, 24 h, 36 h, 48 h, 72 h, 96 h to about 120 h, 144 h, 168 h, 192, 216 h, 240 h, 264 h, 288 h, 312 h, 336 h, 360 h, 384 h, 408 h. Subsequently, the protein encoded by the nucleic acid comprising SEQ ID NO: 5 of the invention may be isolated and purified. For example, the protein of the invention may be purified and isolated by chromatography, e.g. ion-exchange chromatography, size-exclusion chromatography, ammonium sulfate precipitation, or ultrafiltration.

In a preferred embodiment of the present invention, the purified protein comprises the amino acid according to SEQ ID NO: 3. Accordingly, the purified protein according to the invention lacks a signal sequence, e.g. the peptide sequence in which the amino acid sequence according to SEQ ID NO: 4 has been removed.

According to one preferred embodiment of the invention, the isolated and purified protein is a multimer, e.g. the isolated and purified protein comprises at least two or four subunits each of which comprises the protein according to SEQ ID NO: 3, preferably, the isolated and purified protein of the invention is a tetramer.

In one embodiment of the invention the isolated and purified protein as disclosed above, may be used in the inventive method as disclosed above. For example, the isolated and purified protein of the invention may be used as second label in the inventive method for the non-covalent surface display of Fc-containing proteins as disclosed above. For example, the inventive protein may be used for the surface display of monoclonal antibodies, or e.g. the surface display of Fc-domain containing antibody fragments to select e.g. antibodies or antibody fragments of having the desired phenotype, such as e.g. increased affinity to a given epitope or antigen.

In one embodiment the present invention provides a kit of parts which comprises a first label as disclosed above, an isolated protein comprising the amino acid sequence according to SEQ ID NO: 3 as disclosed above, or a nucleic acid molecule comprising the nucleotide sequence according to SEQ ID NO: 5 as disclosed above and a host cell as disclosed above.

The nucleic acid molecule and/or the protein comprised in the inventive kit of parts may be provided in lyophilized form. In one aspect of the invention, the host cells, the first label and second label may be provided in separate vials, or packaging. The inventive kit of parts may further comprise instructions for the inventive method and the use of the materials contained therein.

It is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

EXAMPLES

Example 1: Generation and Preparation of Streptavidin-ZZ (SA-ZZ)

The DNA-sequence for the chimeric construct of streptavidin and Staphylococcus aureus protein A-derived ZZ-domain was synthesized at GeneArt® (Life Technologies) and cloned into a pCMV-based vector containing the PAC selection marker. The synthesized sequence contains: a human growth hormone signal peptide, the streptavidin gene, a GS-linker and two copies of the Z-domain.

CHO-S cells were transfected with this plasmid to produce the protein. The protein was then purified from the supernatant by affinity chromatography using NHS-activated Sepharose (via primary amino groups on the protein)

linked to IgG and size exclusion chromatography (HiLoad Superdex 200 pg column, GE Healthcare).

Stable cells were selected and were used to produce the SA-ZZ. Secreted crude material was purified on NHS-activated Sepharose (via primary amino groups on the protein) linked to IgG (DI-17E6).

Figure 1B:
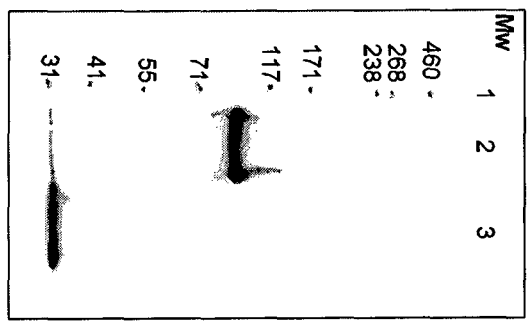
Figure 1B:
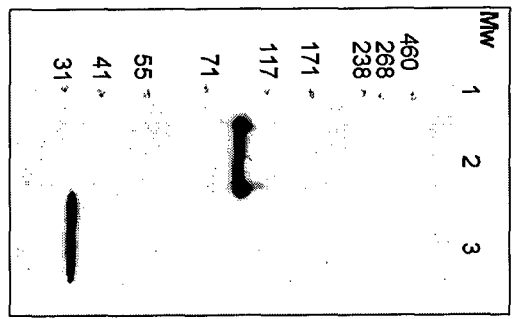
Figure 2:
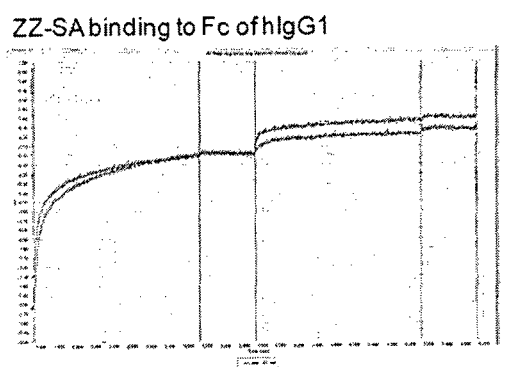
FIG. 2: Octet analysis for binding of SA-ZZ to an IgG captured on anti-human Fc capture tips (AHC tips) (left) and SA-ZZ to biotinylated HRP captured on streptavidin tips (right).
Figure 2:
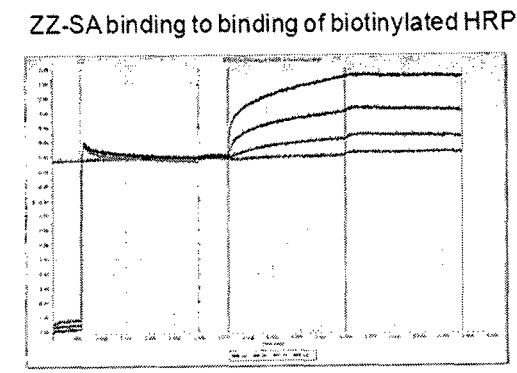
Figure 3:
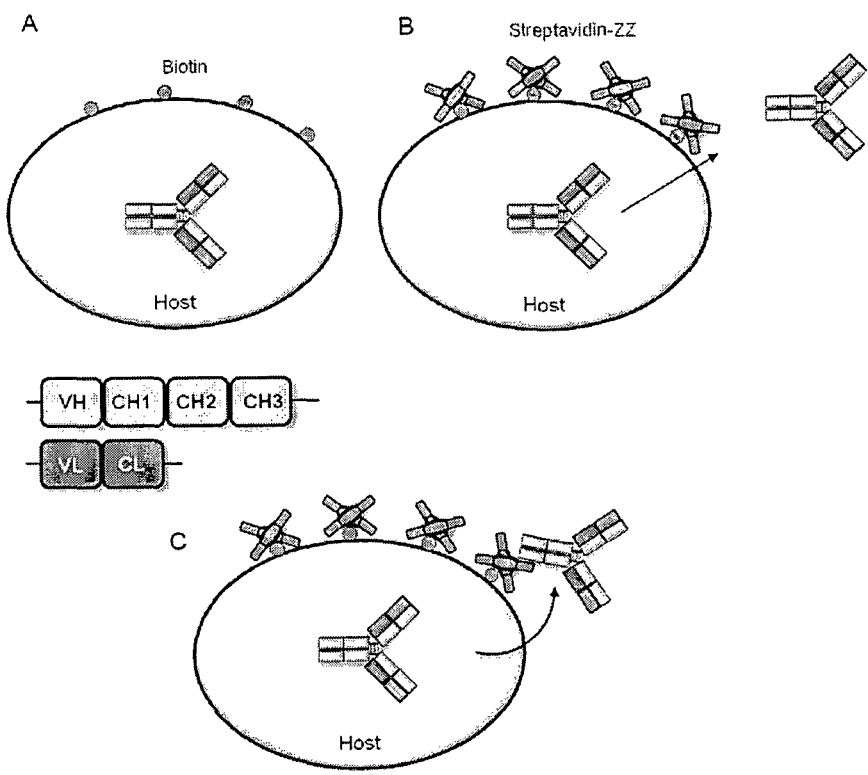
FIG. 3: Schematic illustration of host cells modified by REAL-Select for the purpose of endogeneous antibody cell surface display. Host cells carrying plasmids encoding an antibody are first biotinylated by the use of a commercially available biotinylation reagent (A). This modification is followed by the decoration of cells with the recombinant fusion protein streptavidin-ZZ (SA-ZZ) (B), which enables the recapturing of secreted antibodies to the cell surface (C).

Coomassie blue gel analysis revealed an apparent molecular weight of 91 kD (FIG. 1) with the monomer having an expected size of 31 kD. Octet analysis revealed binding of both SA to biotinylated target and ZZ to an antibody (FIG. 2). Western blot analysis also showed that SA-ZZ fusion proteins bind both IgG and biotinylated protein (FIG. 1).

Example 2: Plasmids

All vectors used for yeast transformation were based on the pYD1-plasmid backbone that was commercially available from Invitrogen (Yeast Display Vector Kit, version D, # V835-01). Construction of each vector was performed using the homologous recombination machinery in *S. cerevisiae*. Antibody genes for that purpose were amplified using the Phusion® High-Fidelity DNA-Polymerase (New England Biolabs) with HPLC-purified primers (Eurofins MWG Biotech) introducing a 40 to 50 bp extension of homologous sequences at both sides. To enable selection of heavy and light chain plasmids in yeast, the light chain plasmid contained a Leu auxotrophy marker, while the heavy chain plasmid encoded a Trp-marker. VH and VL regions from each antibody to be displayed (matuzumab, adalimumab, anti-cMet-B10, trastuzumab) were cloned into the respective plasmids already containing the signal sequence and. IgG1 CH1-Fc regions (pYD-mcs-CH1-Fc) or lambda/kappa constant regions. Soluble antibody secretion was directed using the αMFpp8 signal sequence that was cloned in-frame 5' of the antibody gene. The expression of the antibody genes was driven by the galactose-inducible Gal1-promoter.

Example 3: CDR-H3 Library Generation

A CDR-H3 mutated library containing the VH-region of an in-house selected human cMet-specific phage display derived antibody was ordered and obtained from GeneArt® (Life Technologies). Within the library comprising a 30 nucleotide DNA-stretch, a doping mixture was chosen to keep each amino acid in CDR-H3 parental with a frequency of 60-70% and to avoid the introduction of stop-codons as well as cysteine and methionine residues. The synthesized dsDNA construct was used as a template for PCR amplification. During PCR a 45 bp extension for gap repair cloning in yeast to both sides of the library was achieved. 96 reactions were performed using the Phusion® High-Fidelity DNA polymerase (New England Biolabs) according to the manufacturer's protocol. For each reaction 50 ng of the pre-amplified template DNA was used in a total volume of 50 µl. The reactions were combined after completing PCR and purified using the Wizard® SV Gel and PCR Clean-Up system (Promega) and a final amount of 102 µg library-DNA was obtained carrying homologous sequence-attachments to the acceptor-plasmid 5' and 3' of the sequence.

The following primers were used for amplification: up-primer 5'-CTATTGCCAGCATTGCT-GCTAAAGAAGAAGGGGTACAACTCGATAAAA GAGAAGTGCAGCTGGTGCAGTC-TG-3' (SEQ ID NO: 29), low-primer 5'-CTCTTGGAGGAGGGTGCCA-GGGGGAAGACCGATGGGCCCTTGGTGGA GGCT-GAGGAGACGGTGACCAGGG-3' (SEQ ID NO: 30)

to enable the cloning of the library in-frame with the signal peptide and the human CH1-Fc region that were already included in the plasmid backbone. For gap-repair cloning the pYD-mcs-CH1-Fc was linearized using the restriction enzymes BamHI and EcoRI and purified via Wizard® SV Gel and PCR Clean-Up system. The library generation via gap repair cloning in EBY100 cells was performed following the protocol established by Benatuil and colleagues.[33] Ten electroporations were conducted with 4 µg of the linearized vector and 10 µg of the PCR-product. The library size was estimated by dilution plating and revealed $1.5 \times 10^9$ transformants.

Example 4: Cell Surface Functionalization for Antibody Capture

For antibody capture, the fusion protein consisting of streptavidin and a ZZ domain (SA-ZZ, see Example 1) was constructed and purified from stably transfected CHO-S cells. To investigate whether the fusion can be captured to the cell surface while maintaining the antibody-binding capability, the cell surface was biotinylated using a commercially available biotin-reagent (biotin-PEG-SCM 3.4 kDa, Creative PEGWorks), followed by addition of the recombinant SA-ZZ fusion protein.

Figure 4:
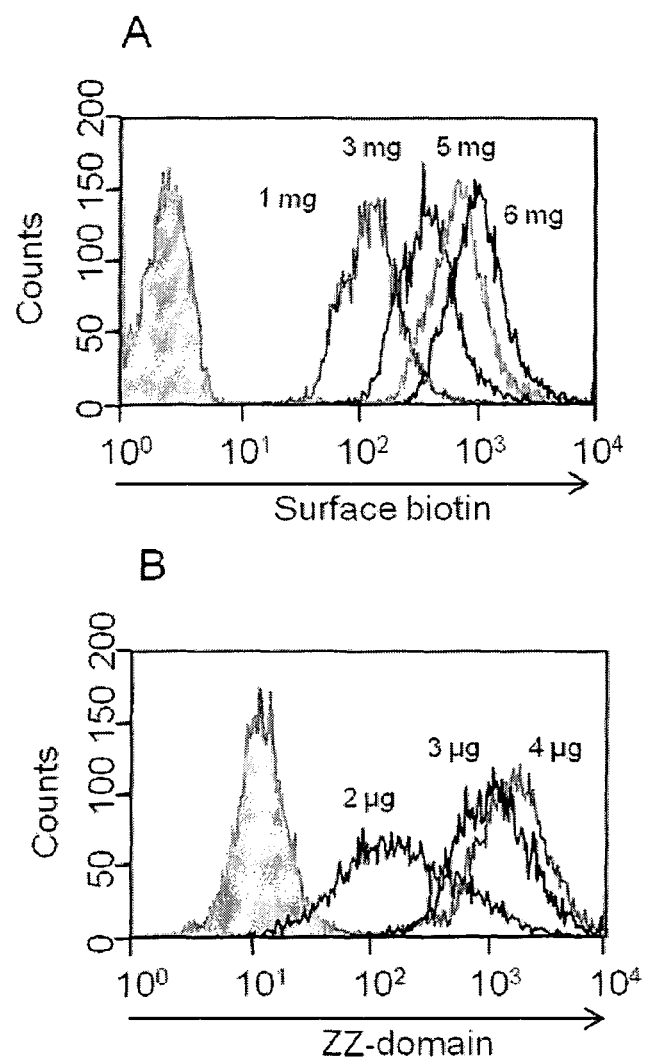
FIG. 4: Titration of reagents for biotin-labeling and SA-ZZ immobilization on yeast cells. Respective indirect fluorescence signals were analyzed by flow cytometry. (A) $1\times10^7$ cells were labeled with 1 mg to 6 mg biotin reagent and stained with streptavidin-Dylight633. (B) $1\times10^7$ cells labeled with 1 mg biotin were incubated with 2, 3 or 4 µg of SA-ZZ for immobilization of the Fc-capture moiety. Subsequently surface ZZ domain was detected using a FITC-conjugated goat-anti-protein A antibody.

Initially, amounts of biotin-reagent and SA-ZZ were tested aiming for sufficient labeling of the cell surface. For that purpose, BJ5464 *S. cerevisiae* cells were biotinylated using 1-6 mg of biotin-PEG-SCM 3.4 kDa per $1 \times 10^7$ cells. To analyze the extent of surface labelling, cells were incubated with streptavidin-Dylight633 and the fluorescence was detected by flow cytometry. With increasing amounts of the reagent the fluorescence-signal enhanced continuously (FIG. 4A). As cells that are labeled with 1 mg of the biotin reagent already showed an increase in fluorescence by about one order of magnitude compared to the negative control, 1 mg reagent was chosen for subsequent SA-ZZ immobilization to avoid avidity effects upon antigen binding that may arise upon high density antibody loading onto the cell surface. Different quantities of SA-ZZ (2 µg, 3 µg, 4 µg) were used for the incubation with biotinylated cells to functionalize the cell surface with the IgG-capture domain. Functionalized cells were incubated with a protein A-specific FITC-conjugated goat antibody (ab7244, abcam) allowing flow cytometric analysis of cell surface-immobilized. Increasing the amount of SA-ZZ resulted in an enhancement of the fluorescence signal (FIG. 4B), caused by the higher surface density of immobilized capture-domains. A distinct fluorescence shift compared to the negative control was detected for all SA-ZZ concentrations tested.

Example 5: IgG Capture

Figure 5:
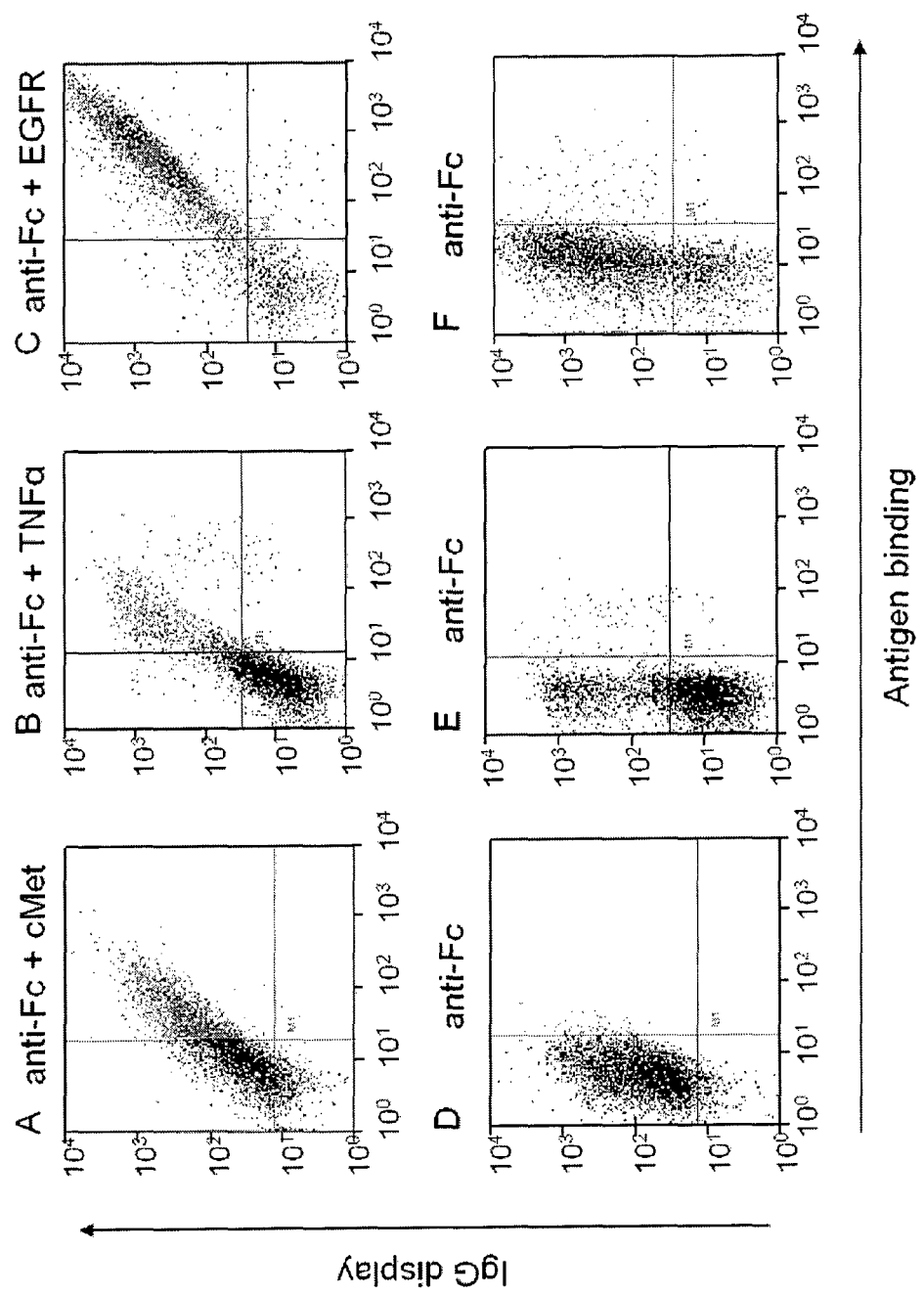
FIG. 5: REAL-Select functionalized yeast cell phenotype of three different mAbs analyzed by flow cytometry. (A) anti-cMet-B10, (B) adalimumab (C) matuzumab and the respective controls without (D) cMet, (E) TNFα, (F) EGFR. Display of functional antibodies was detected using the respective fluorescence-labeled antigen (Table 1) and an Fc-specific detection antibody (IgG display).

The ability of functionalized cells to still secrete soluble high-quality antibodies was examined. BJ5464 cells were transformed with heavy and light chain plasmids encoding three different monoclonal antibodies. These antibodies were matuzumab ($K_D$ 113 nM), adalimumab ($K_D$ 30 pM) and anti-cMet-B10 (analyzed with $K_D$ 40 nM) (see: Table 1). Analysis of IgG-capture was carried out by incubation of the modified cells with the fluorescently labeled antigen listed in Table 1 and an anti-Fc specific AlexaFluor647-conjugated F(ab')2 fragment (109-606-008, Jackson ImmunoResearch) or an goat anti-Fc PE-conjugated antibody (109-115-098, Jackson ImmunoResearch) for detection of IgG display by flow cytometry (FIG. 5A-C). As a negative control cells were only stained for the detection of IgG-display (FIG.

5D-F). The three tested double-stained cell samples showed a positive signal for antibody display and antigen binding, indicated by a double positive fluorescence signal compared to the respective negative control labeled with anti-Fc only.

For further analysis of IgG expression and extent of ZZ domain occupation, BJ5464 cells carrying heavy and light chain plasmids for matuzumab were functionalized by the inventive method and antibody expression was induced using galactose media. After cell labeling with the ZZ domain cells were allowed to grow and secrete matuzumab. As expected, the number of ZZ domains covalently attached to the cell wall decreased 6 and 20 hours after immobilization, most likely due to cell growth and budding as well as degradation or inactivation of the fusion protein upon prolonged incubation in media at 20° C. (FIG. 6C-E). The occupation of the immobilized ZZ domains with matuzumab (FIG. 6B) was simultaneously monitored using an goat anti-Fc PE-conjugated antibody (FIG. 6I, J) showing a similar labeling pattern as for the ZZ domain. To investigate whether unoccupied ZZ domains reside on the cell surface that are not covered by secreted matuzumab, cells were collected at three time points after induction of matuzumab secretion and incubated in excess with golimumab antibody. Golimumab binding to unoccupied ZZ domains on the yeast cell surface was monitored by addition of the corresponding fluorescently labeled antigen, TNFα After 6 hours of expression, all functionalized cells captured endogenous matuzumab (FIG. 4I), while cell staining with the externally added antibody was low and completely absent after 20 h incubation (FIG. 4H), indicating that the ZZ domains residing on the yeast cell surface were fully saturated with endogenously produced antibody.

Example 6: Yeast Strains, Media and Mating

The yeast strain that harbored antibody light chains was *S. cerevisiae* strain BJ5464 obtained from the American Type Culture Collection (ATCC). The *S. cerevisiae* strain EBY100 harbored antibody heavy chains and was used to generate the parsimonious heavy chain library. This strain was obtained from Invitrogen as part of the pYD1 Yeast Display Vector Kit (# V835-01, Life Technologies). The whole antibody and library was secreted by resulting diploid cells after mating.

For the cultivation of yeast cells harboring heavy and/or light chain plasmids, media containing all essential reagents except tryptophan and/or leucin was prepared using a commercially available drop-out mix and a minimal SD-base mix (#630414, #630413, #630417 and #630411, Clontech). The induction of gene expression was carried out in the same drop-out mix combined with minimal SD-base Gal/Raf (#630421, Clontech), 1 M buffer containing 8.56 g $NaH_2PO_4$ and 5.4 g $Na_2HPO_4$, pH 7.4 and 11% w/v PEG8000. Rich medium (YPD) used for yeast cell mating was prepared from 20 g glucose, 20 g peptone and 10 g yeast extract (Merck KGaA). Freezing medium was prepared using 2% glycerol and 0.67% Difco™ yeast nitrogen base (BD).

Mating

Yeast mating was used for the combination of the CDR-H3 library in haploid EBY100 cells (Mat a) with the corresponding light chain in haploid BJ5464 cells (Mat α) to gain diploid cells harboring heavy and light chain plasmids. Therefore yeast cells carrying the plasmid for the antibody, heavy or light chain, respectively, were at first independently cultivated in their respective selective medium over night at 30° C. and 250 rpm. The next day, $1 \times 10^8$ cells of each strain were resuspended in 50 µl of YPD-medium, mixed and dripped onto the middle of a pre-warmed YPD-plate which was afterwards cultivated at 30° C. over night. The thin cell layer was then washed off with 10 ml of YPD-medium. To calculate the efficiency of the mating process, the $OD_{600}$ of the cell suspension was measured and dilution plates were prepared. The cell suspension was cultivated in 500 ml of double selective medium. $2 \times 10^8$ cells were subsequently transferred into fresh medium after 24 and 48 hours of cultivation. Afterwards the diploid cells were resuspended in freezing medium and transferred to a cryo-vial and stored at −80° C.

Example 7: Genotype-Phenotype Coupling and Library Screening

To verify that a genotype-phenotype linkage exists for the inventive method, a mixing experiment was performed. EGFR-binding matuzumab displaying cells (FIG. 5A) were mixed with trastuzumab displaying cells (FIG. 5B) at a 1 to 1,000,000 ratio, mimicking the size of a conventional immune library. SA-ZZ was immobilized on the surface of yeast cells, and the mixture was transferred to induction media, incubated for 20 hours and subsequently fluorescently labeled with an EGFR-phycoerythrin (EGFR-PE) conjugate and an anti-Fc AlexaFluor647-conjugated antibody and subjected to 4 consecutive rounds of sorting (FIG. 5C-F). After sorting and re-sorting round 4, a single cell analysis of cells for EGFR binding was performed by flow cytometry. Of ten analyzed clones, nine displayed binding to EGFR-PE, confirming successful enrichment (data not shown).

Figure 6:
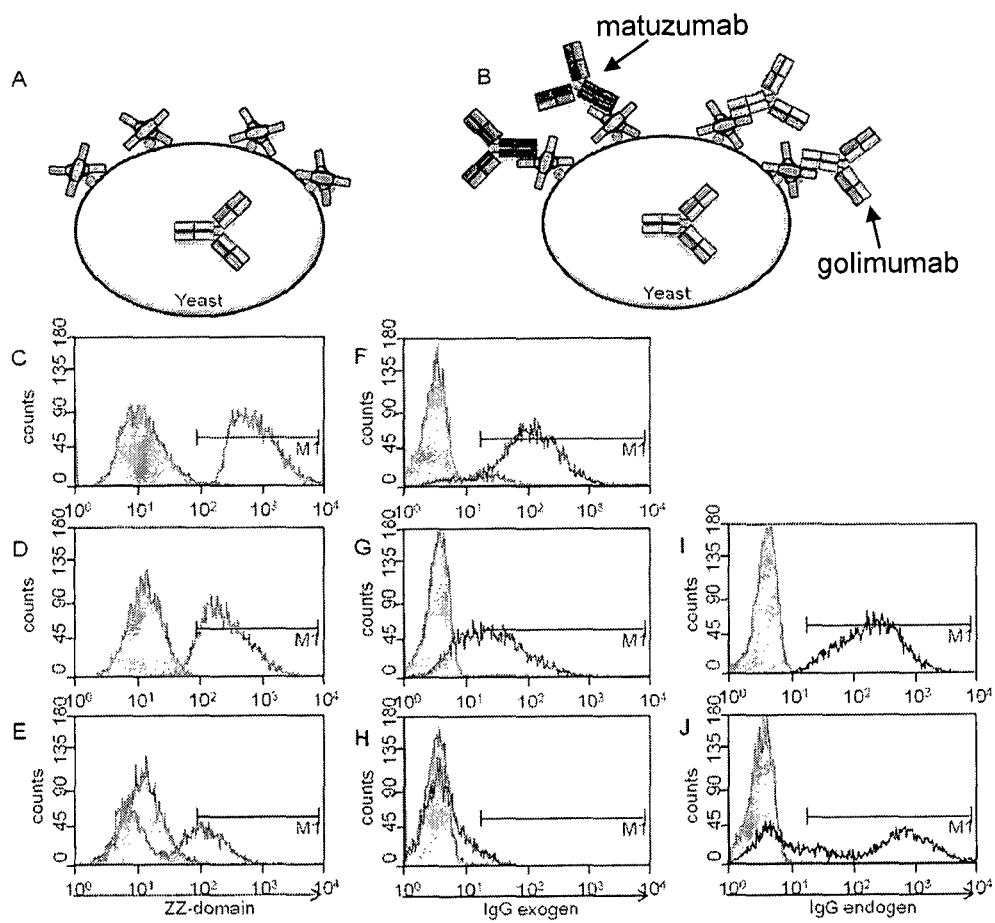
FIG. 6: Flow cytometric analysis of capture domain saturation of REAL-Select functionalized yeast cells. (A) SA-ZZ decorated cells carrying matuzumab heavy and light chain plasmids, (B) surface capture of matuzumab (blue antibody) or externally added golimumab (red antibody). (C-E) Analysis of yeast cells decorated with SA-ZZ fusion protein with goat-anti-protein A-FITC 0 hours, 6 hours and 20 hours after surface decoration and induction of matuzumab expression. (F-H) Detection of unoccupied Fc-capture domains by incubation of cells with golimumab followed by labeling with TNFα-Dylight650 at indicated time points. (I,J) Monitoring of surface display of re-captured matuzumab by labeling cells with goat-anti-Fc F(ab')$_2$-AlexaFluor647 at 6 hours and 20 hours of expression.

Encouraged by this result, an affinity maturation of a cMet specific antibody derived from an in-house phage display library screening campaign ($K_D$ 40 nM) was performed. To this end, a parsimonious mutagenesis of the CDR-H3 loop of the variable domain of the heavy chain was performed, where all ten residues were randomized with all 19 amino acids except Cys and Met, keeping the original amino acid at each position with a frequency of approximately 60-70%. The library was constructed in *S. cerevisiae* strain EBY100 resulting in approximately $1.5 \times 10^9$ transformants. Sequence analysis of randomly picked clones revealed on average 3.4 substitutions within the ten residues of the CDR-H3. The haploid library cells were mated with haploid BJ5464 (MAT-alpha cells carrying the parental light chain of the antibody with a mating efficiency of 15%. Diplonts were selected by their ability to grow on double-selective media and decorated with SA-ZZ. The secreted antibodies were recaptured to the cell surface and labeled with an anti-Fc AlexaFluor647-conjugated F(ab')$_2$ and PE-conjugated cMet and double stained cells were isolated by FACS (FIG. 6).

Figure 7:
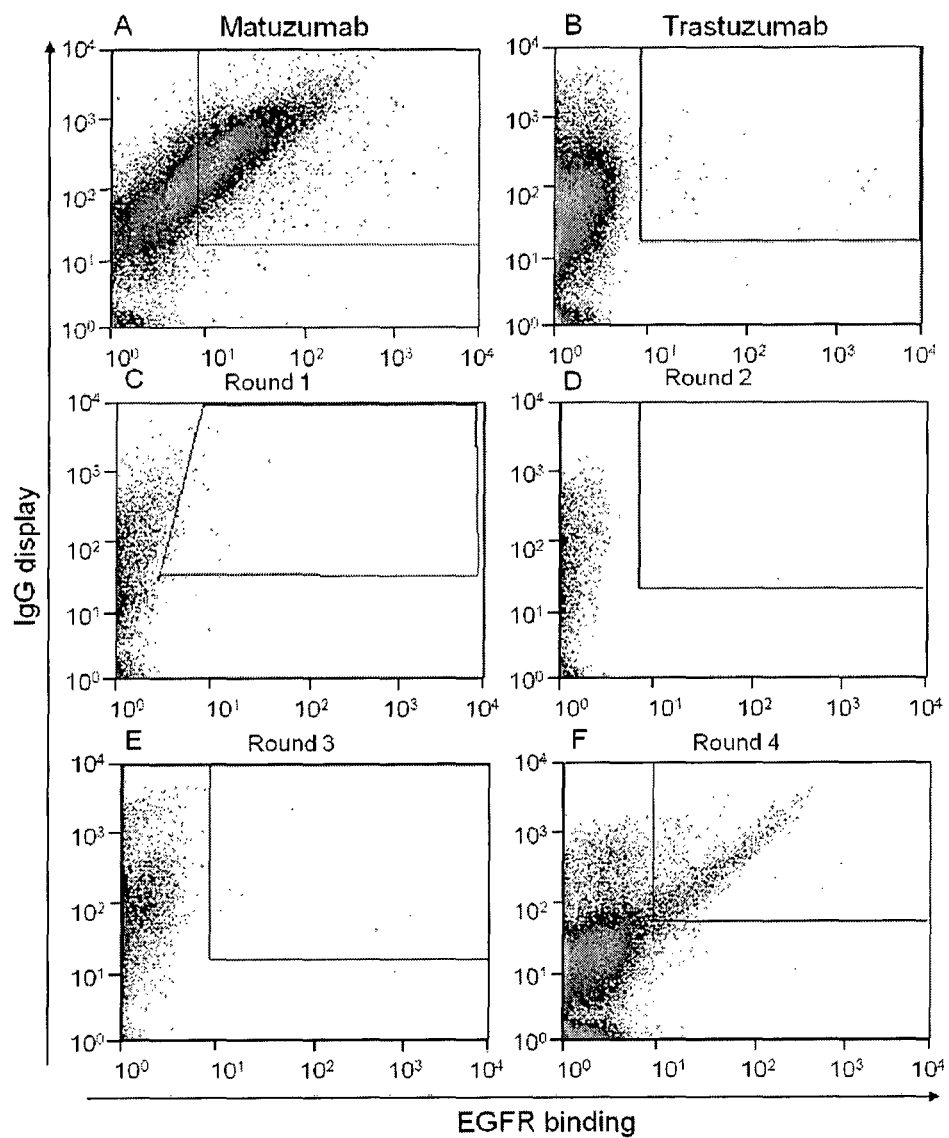
FIG. 7: FACS analysis of REAL-Select enrichment of matuzumab-displaying cells. Functionalized yeast cells displaying (A) matuzumab or (B) trastuzumab were mixed 1:1,000,000 (C) and labeled using EGFR-PE and goat-anti-Fc F(ab')$_2$ AlexaFluor647. (C-F) Matuzumab displaying cells were enriched by FACS within four consecutive rounds of sorting.
Figure 8:
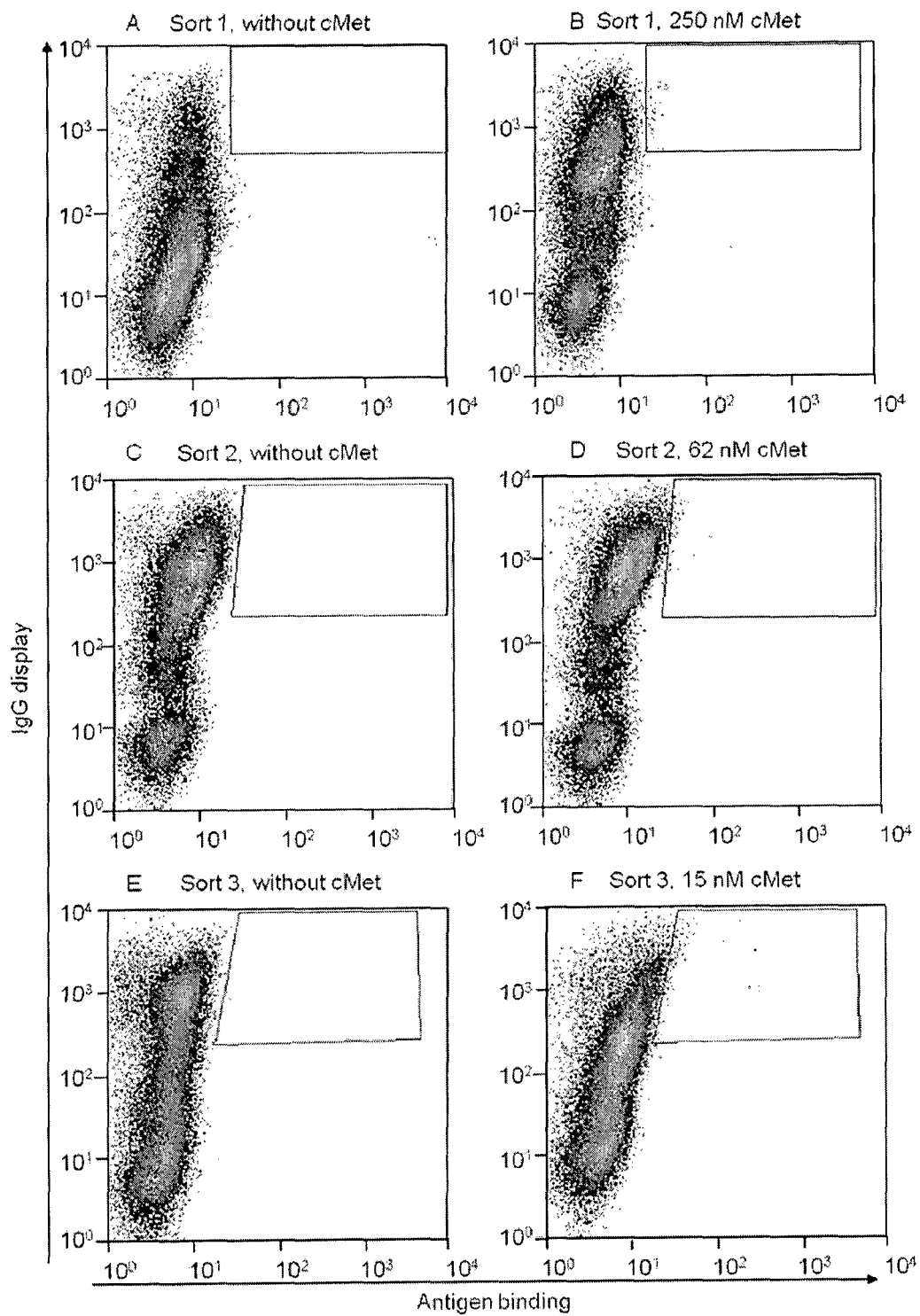
FIG. 8: CDR-H3 library yeast cell phenotype and selection strategy for the affinity maturation of a cMet specific antibody towards three rounds of FACS screening with decreasing antigen-concentrations (B) 250 nM, (D) 62 nM, (F) 15 nM cMet and anti-Fc AlexaFluor647 for display detection. As a specific control for each sorting round, enriched library cells were induced for IgG secretion and labeled with an anti-Fc AlexaFluor647-conjugated antibody only (A,C,E).
Figure 9:
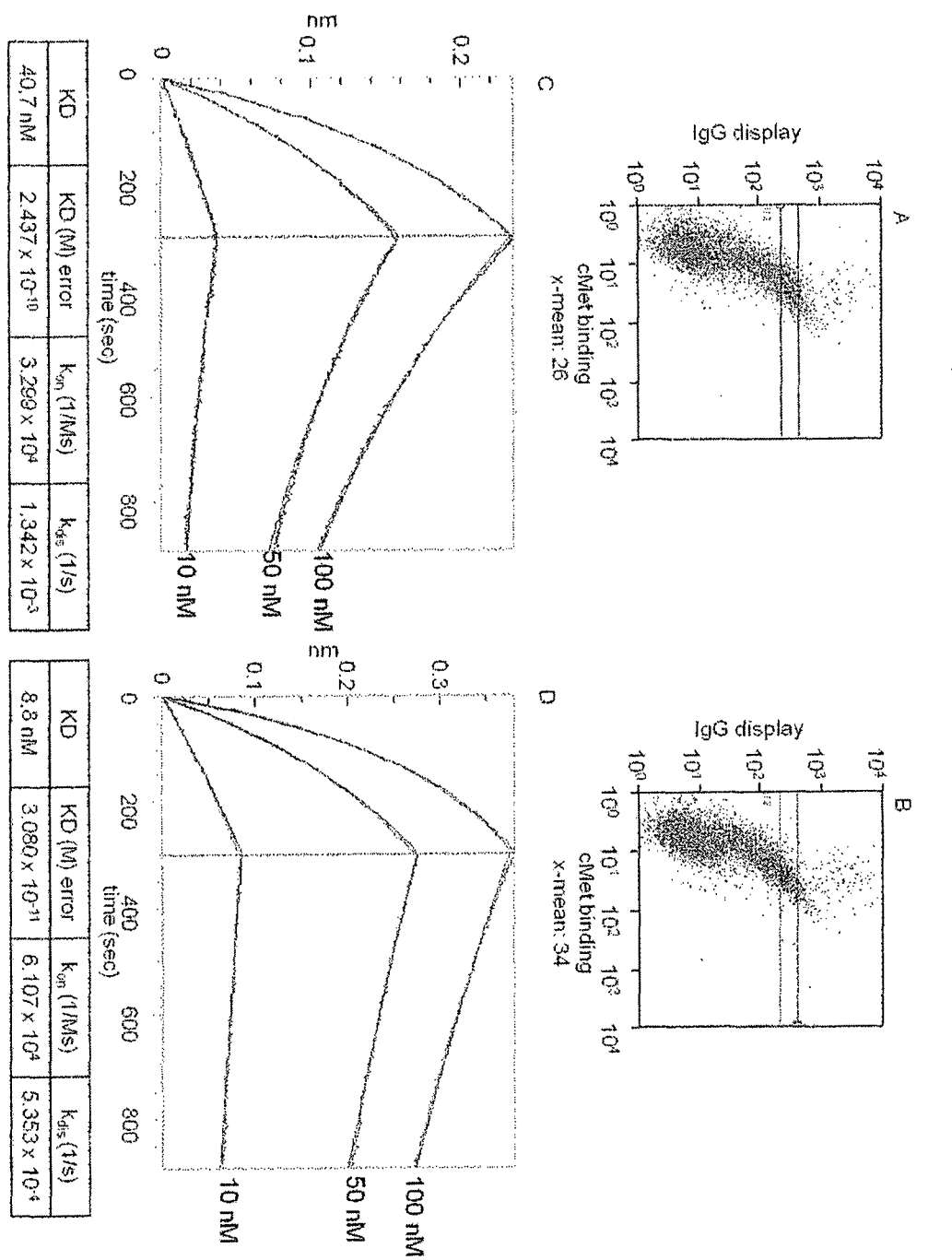
FIG. 9: Functional characterization of an antibody with improved binding of cMet. (A,B) FACS analysis of (A) yeast cells displaying parental antibody, (B) cells displaying the selected antibody labeled with 100 nM cMet-PE and anti-Fc AlexaFluor647. (C) Binding kinetics of Expi293 expressed parental antibody and (D) affinity-matured antibody variant to cMet (100 nM, 50 nM, 10 nM) determined by biolayer interferometry. Association rate constants (kon), dissociation rate constants (kdis) and binding affinities (KD) of both antibodies were determined assuming a 1:1 binding model.
Figure 10:
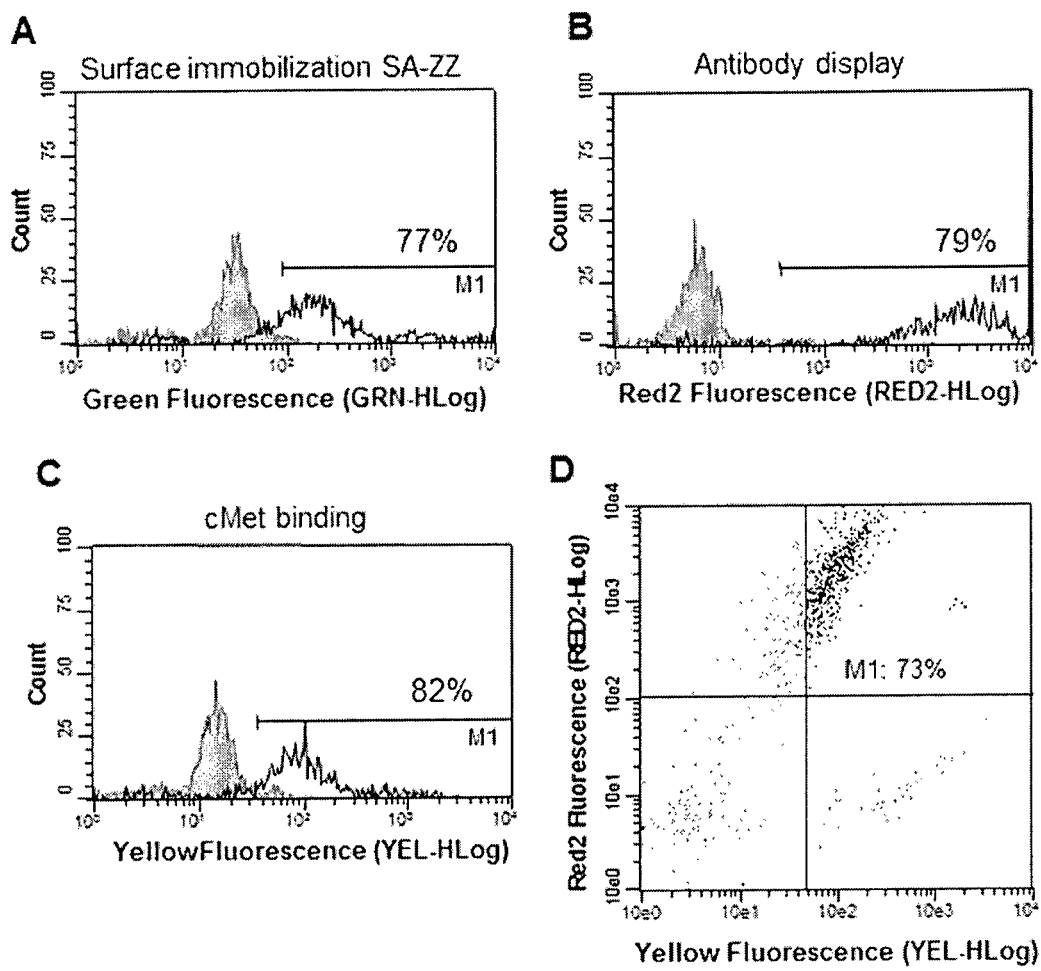
FIG. 10: REAL-Select is compatible with other expression hosts than *S. cerevisiae*, the display of full-length IgG molecules on Expi293F™ cells as an example for mammalian expression hosts was examined using the new technology.

To obtain binders with higher affinity, the cMet concentration was successively reduced from 250 nM to 15 nM over three sorting rounds. After the third round of sorting, plasmid DNA of yeast cells was isolated and used to transform *E. coli* cells. VH-regions of heavy chain plasmids from resulting single colonies were sequenced and unique sequences were used to co-transform yeast cells with the parental light chain plasmid by electroporation. A phenotypical analysis regarding cMet-binding was conducted on the surface of yeast cells. At 100 nM cMet concentration one variant exhibited a slightly enhanced fluorescence signal for the antigen binding compared to the parental antibody upon normalization of the display ratio (FIG. 7).

The selected sequence was subsequently subcloned into a mammalian vector for soluble expression in Expi293F™ cells. Following antibody expression and purification, kinetic analysis of the antibody variant revealed a 5-fold improved affinity to cMet (FIG. 7D) compared to the parental antibody (FIG. 7C). This difference is mainly driven by a decreased $k_{dis}$.

Example 8: Cell Surface Manipulation

Yeast cells were biotinylated using a 3.4 kDa biotin-PEG-SCM (Creative PEGWorks). To achieve this, $1 \times 10^7$ cells were washed twice with carbonate-buffer (4.2% $NaHCO_3$ and 0.034% $Na_2CO_3$, pH 8) and resuspended in a final amount of 40 µl of the buffer containing 1-4 mg of dissolved biotin-reagent. The mixture was then incubated for 15 minutes at room temperature. The cells were pelleted and washed twice with 1 ml PBS containing 100 mM glycine to saturate free biotin-PEG-SCM. The subsequent functionalization of the biotinylated cells was performed by incubating the cells with 0.76-1.52 µM of the streptavidin-ZZ fusion in PBS on ice for another 15 minutes. In a final step, the cells were washed once with 1 ml PBS.

Example 9: IgG Display, Fluorescence Staining and FACS

For recapture and display of secreted IgG-molecules on yeast cells the expression was performed in a static culture using petri dishes or deep-well plates for 20 hours at 20° C. at an initial cell concentration of $1 \times 10^7$ cells/ml. To specifically label surface biotin, $1 \times 10^7$ biotinylated cells were incubated with 1.3 µM of a streptavidin-DyLight633 conjugate (Thermo Scientific/Pierce) in 20 µl at 4° C. for 15 min without light and once washed with PBS after labeling. The staining of surface-immobilized ZZ domain was carried out by incubating $1 \times 10^7$ cells with 3.3 µM in 20 µl of a protein A-specific FITC-conjugated detection antibody originating from goat (Abcam) for 15 min in the absence of light at 4° C. Following antibody incubation, the cells were washed once with PBS and kept on ice until analysis. The staining of displayed antibodies was performed using 0.5 µM in 20 µl of an AlexaFluor647-conjugated goat anti-Fc F(ab')$_2$-fragment or PE-conjugated goat anti-Fc antibody (both Jackson Immunoresearch) and different concentrations of the corresponding fluorescence labeled antigen (cMet or EGFR, Merck Serono and TNFα, R&D Systems). The labeling of the antigens cMet and EGFR was done using the LYNX rapid RPE kit (BioRad). The labeling of TNFα was done using Dylight650 NHS ester (Thermo Scientific). For the staining with PE-conjugated antigen cells were incubated on ice and in the absence of light for 15 min and washed once with 1 ml PBS. The concentration of externally given antibody golimmuab (MSD) to label free surface ZZ domains was titrated prior to the experiment to determine the maximum signal intensity. Golimumab treated cells were afterwards incubated with 250 nM of Dyligt650-conjugated TNFα. The selection of the CDR-H3 library was carried out with the MoFlo XDP cell sorter (Beckman Coulter) using Summit 5.3. In the initial selection $2 \times 10^8$ cells were processed. During the following two rounds of sorting the remaining diversity of the library was at least 100-fold oversampled.

Example 10: Subcloning, Mammalian Expression and Protein Purification

Subcloning of antibody genes into mammalian expression plasmids was performed to enable soluble production of IgG molecules in Expi293F™ cells (Life Technologies). Therefore the gene of interest was amplified with homologous overlaps to the acceptor plasmid (Lucigen) by PCR. One Shot® TOP10 chemically competent *E. coli* cells (Life Technologies) were afterwards incubated with 1 µl of the PCR-product and 1 µl of the plasmid for 30 min and transformed according to the manufacturer's protocol. The selection of clones occurred on LB-amp plates. Following incubation at 37° C. for 24 hours colonies were picked, plasmid-DNA was isolated and sent to MWG Biotech for sequencing. The correct plasmid-DNA was then used for the transfection of Expi293F™ cells by the ExpiFectamine™ 293 transfection kit (Life Technologies) following the manufacturer's protocol. Cells were incubated at 37° C., 180 rpm and 5% $CO_2$ for 5 days. The IgG containing supernatant was harvested by centrifugation of the cell suspension at 1500×g for 10 min. Antibodies were purified from the supernatant using PROSEP®-A Spin Columns (Merck Millipore).

Example 11: Binding Kinetics

Binding kinetics of subcloned and purified IgG-molecules were analyzed using the Octet RED system (ForteBio, Pall Life Science). Antibodies were captured on anti-human-FC (AHC) biosensors for 600 s at 2.5 µg/ml in PBS. All measurements were performed in kinetics buffer (PBS pH 7.4, 0.1% (w/v) BSA, 0.02% Tween® 20). Association to cMet (10 nM, 50 nM, 100 nM) was measured for 300 s followed by dissociation for 600 s. One control of each antibody was analyzed using kinetics buffer only and subtracted from all binding curves resulting from the interaction with cMet. Processed binding curves were evaluated with the ForteBio data analysis software 8.0 by using a 1:1 binding model after Savitzky-Golay filtering.

Example 12: Labeling of an IgG Displaying Yeast Population

Figure 11:
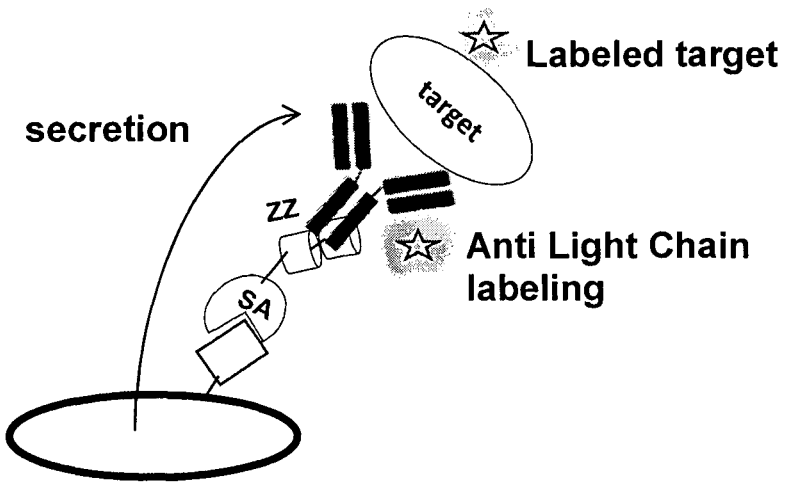
FIG. 11: REAL select using anti-light chain antibodies for labeling surface-displayed antibodies (see example 12). (A) schematic presentation of the light chain labeling (left panel). Cell surface expression of intact antibodies correlates with staining intensity as depicted in the right panel. (B) The Feasibility of light chain labeling was assessed on two independent antibody clones recognizing antigen-A and antigen-B.
Figure 11:
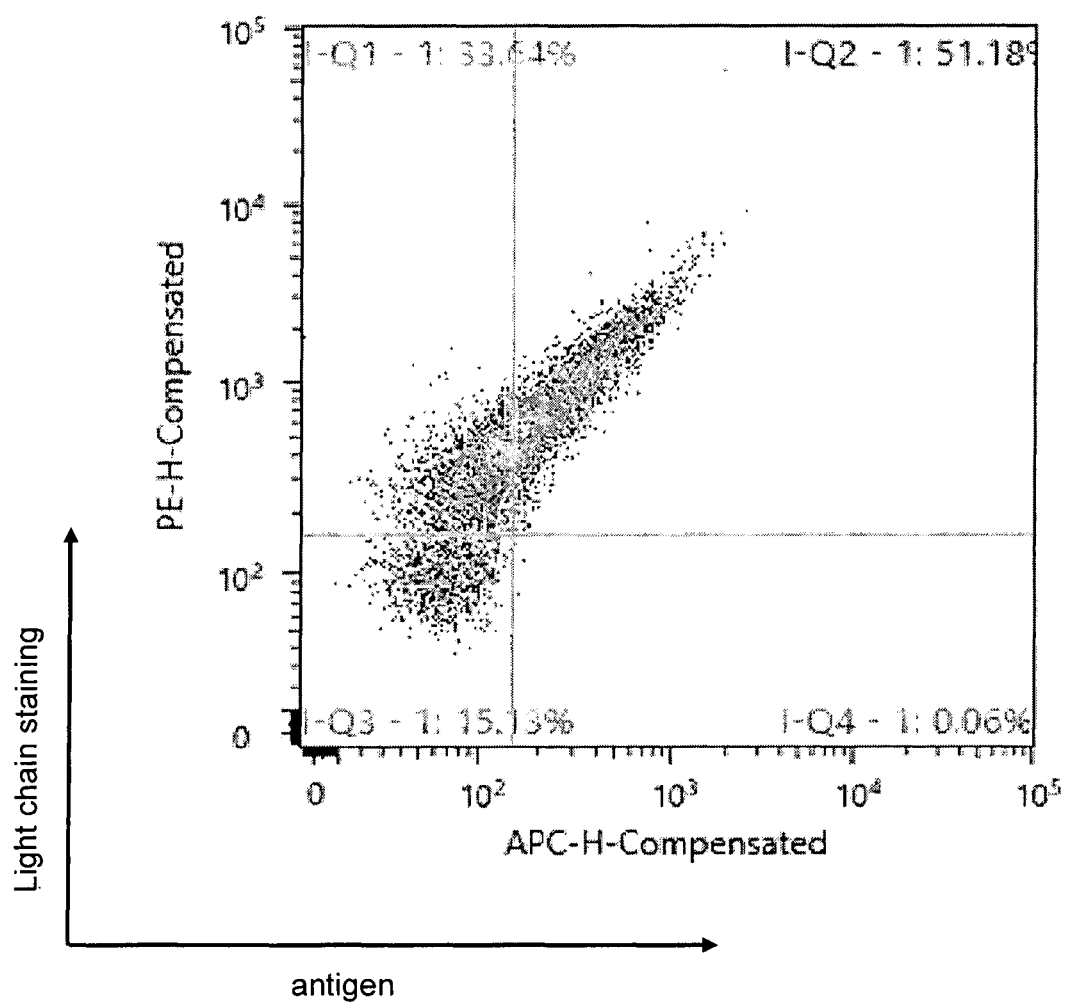
Figure 11:
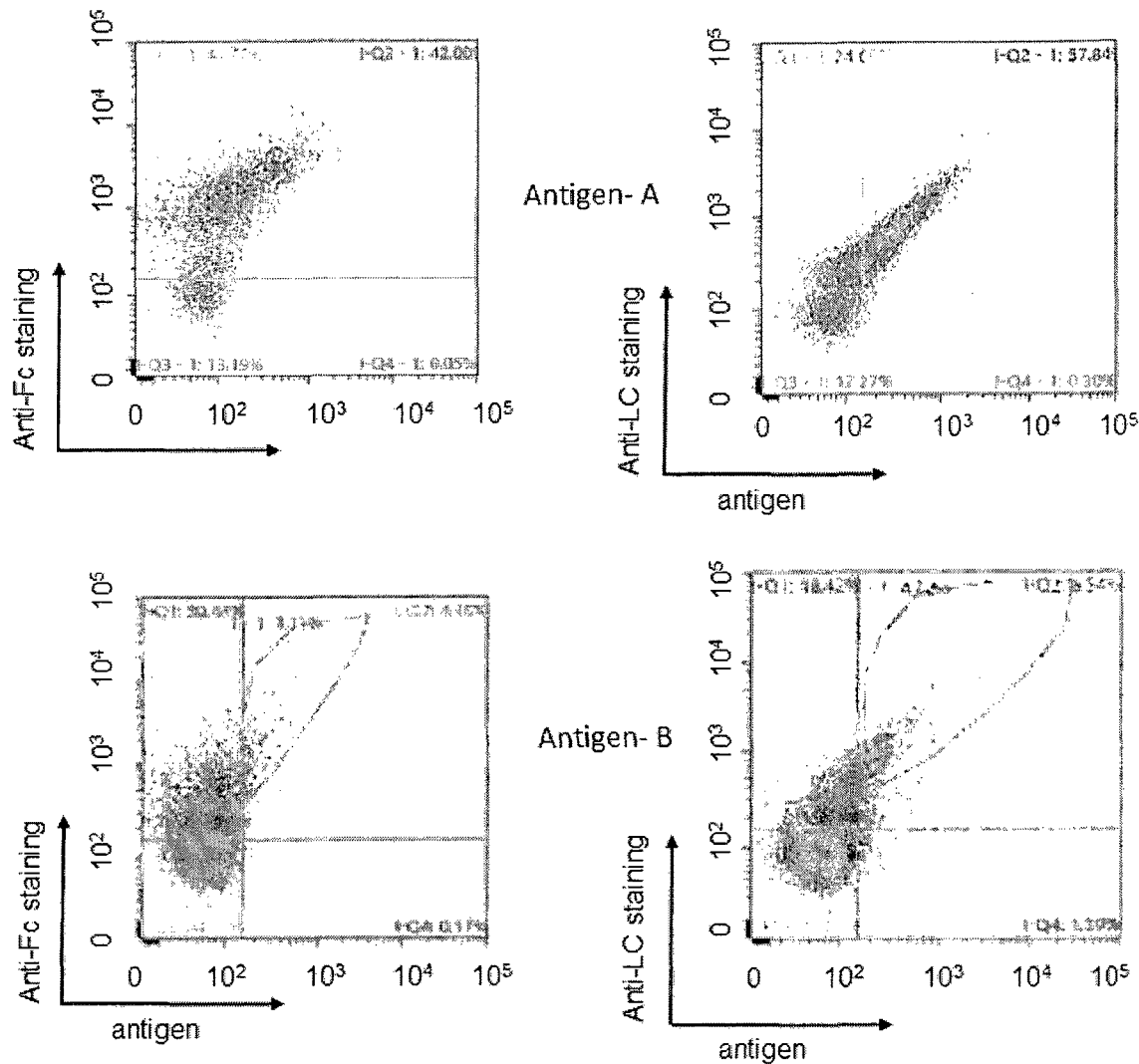

In order to identify yeast cells which display intact IgG, which are marked by the assembly of light chain and heavy chain on their surface from the total pool of yeast cells, yeast cells were induced for non-covalent surface display as described above (cf. Example 9) and were stained with PE conjugated-goat anti-human lambda or kappa F(ab')2 together with Alexa 647-conjugated antigen (Thermo-Fisher). The results obtained in the experiment show a correlation between antigen binding and IgG display level (FIG. 11A). The light chain experiment was done with two independent antibody clones specific for two antigens, antigen-A and antigen-B, respectively. As depicted in FIG. 11B the results obtained are comparable between staining with an anti-Fc antibody and with an anti-light chai antibody. Surprisingly, the anti-light chain staining showed improved correlation (FIG. 11B).

Example 13: Clonal Enrichment by Light Chain Labeling and Selection

Figure 12:
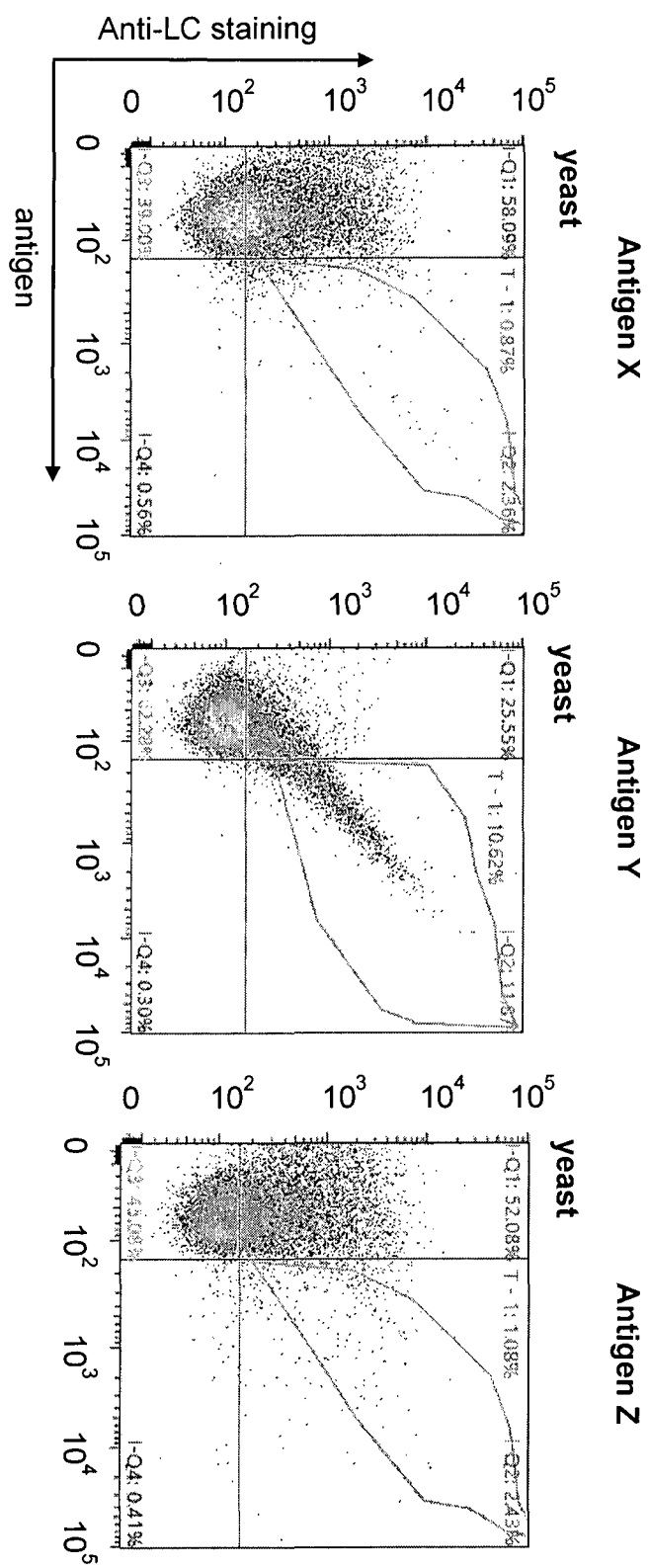
FIG. 12: Depicted are the sorting results of a clonal enrichment experiment as described in Example 13. The results indicate a binding specificity toward Alexa 647-conjugated antigen-Y, showing that the correct antibody clone was successfully enriched from the original pool in which the enriched clone was initially present in a $1:10^6$ dilution.

The yeast display system according to the invention was used in one example for clonal enrichment utilizing the light chain staining method (cf. Example 12). For the clonal enrichment yeast cell clones, which display Y-antigen specific antibodies on their surface utilizing the inventive method as disclosed above (antigen. Y-specific yeast display clones) were mixed with antigen Z-specific yeast display clones in a ratio of 1:1,000,000. The Y-antigen specific antibodies are directed against a protein of interest (POI) of which several isoforms exist, one of which comprises antigen-X, but not antigen-. Accordingly, a Y-antigen specific antibody will not recognize the POI isoform which comprises antigen-X. Following the yeast manipulation procedures described in examples 1-6, $10^8$ yeast cells were screened and sorted for three rounds of enrichment using PE conjugated-goat anti-human lambda F(ab')2 (Southern Biotech) to label the IgG display population for subsequent FACS sorting. Following three rounds of cell sorting and enrichment using an SONY SH800 cell sorter, the sorted cells, i.e. cells within the gating parameters shown in FIG. 11 B, were subsequently analyzed by incubating them with Alexa 647-conjugated antigen-X, antigen-Y or antigen-Z (unrelated protein, negative control). Clear binding specificity toward Alexa 647-conjugated antigen-Y was seen from the selected cells, indicating the correct antibody clone was successfully enriched from the original 1 to 1,000,000 ratio, and the undesired background clone was successfully eliminated during the selection process (FIG. 12).

Example 14: Affinity Maturation Selection by Light Chain Shuffling

Figure 13A:
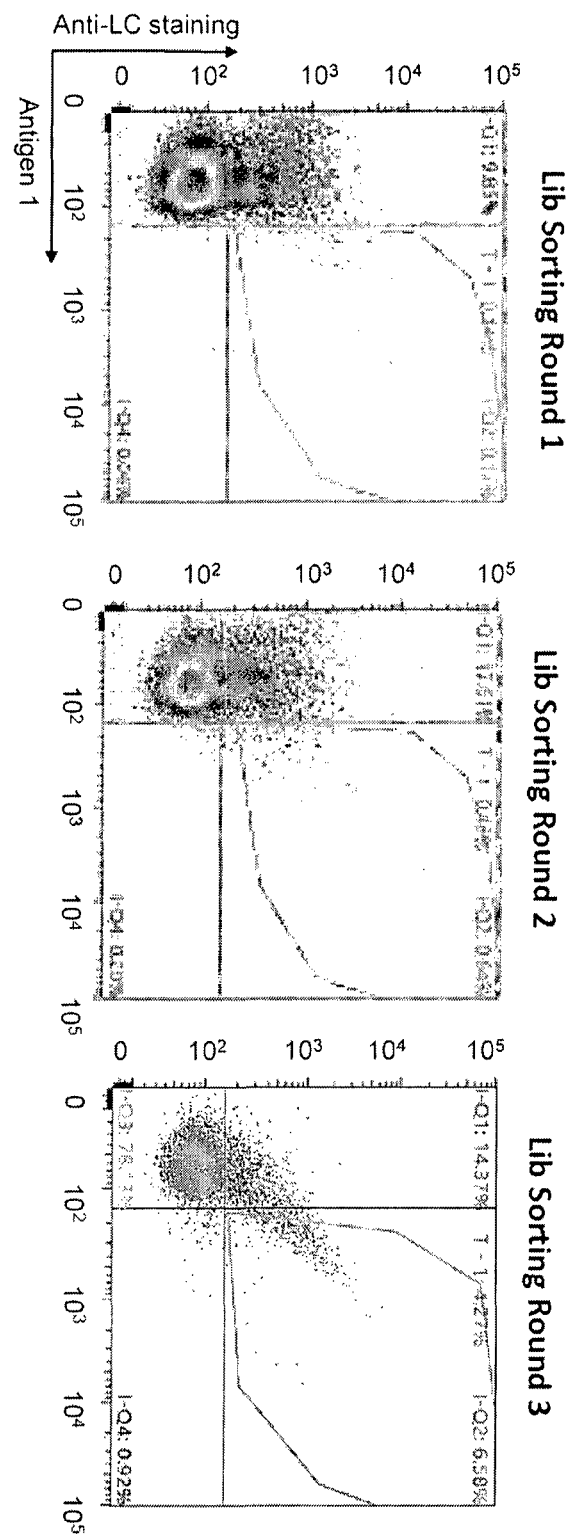
FIG. 13: Use of REAL select in affinity maturation. Depicted are the results of three rounds of affinity maturation and selection by light chain shuffling as described in Example 14. (A) FACS analysis of enriched clones, of which the ones within the gating parameters were selected for further sorting. (B) Biacore™ analysis of an affinity matured antibody clone following three rounds of consecutive selection and enrichment.
Figure 13B:
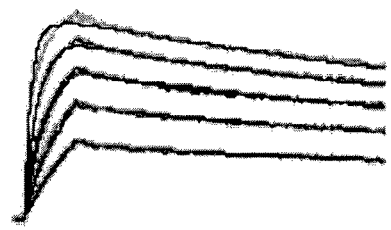
Figure 13B:
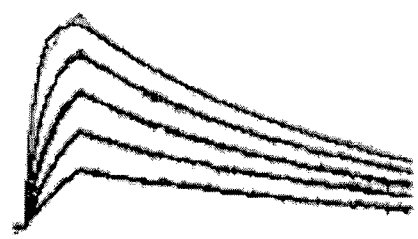

As a proof-of-concept that the yeast display method of the invention may also be utilized in light chain shuffling affinity maturation, light chain shuffling libraries were constructed which were paired with the heavy chain from a parental anti-antigen-1 clone. Following three rounds of sorting and enrichment, which was carried out as disclosed in the above examples, high affinity antigen binding yeast cells were isolated (FIG. 13A) and yeast plasmid DNA isolated. Antibody sequences were reformatted and subcloned into mammalian expression vectors and expressed in a mammalian expression system followed by purification of IgG antibodies and measurement of binding kinetics (Biacore instrument, GE Healthcare, or Octet, Pall Fortebio). The binding affinity of the selected clone from the light chain shuffling screen was improved about 5-fold compared to the parental clone (FIG. 13B).

Tables

TABLE 1

| Antigen specificities and KD-values of antibodies displayed on BJ5464 cells by the inventive method | | |
|---|---|---|
| Antibody | Antigen | KD |
| Matuzumab | huEGFR | 0.34 nM |
| Adalimumab | huTNFα | 30 pM |
| Anti-cMetB10 | hucMet | 40 nM |

---

The invention claimed is:

1. A method for protein display on the surface of a host cell, the method comprising:
   (a) Introducing into a host cell at least one or more polynucleotides which encode a protein of interest to be displayed on the surface of said host cell, wherein the protein of interest comprises at least one Fc-domain;
   (b) Contacting the surface of said host cell with a first label, wherein said first label is biotin, a biotin-derivative, or a biotin analogue and covalently bound to the surface of said host cell;
   (c) Contacting the surface of said host cell of (b) with a second label, whereby the second label specifically and non-covalently binds to said first label and to said protein of interest encoded by said at least one or more polynucleotides, wherein the second label is a multimeric protein, wherein the multimeric protein is or comprises one of protein A, protein L, protein G, protein A-G fusion, domains E, D, A, B of protein A, fused to avidin, strepavidin, neutravidin, or sequence variants thereof;
   (d) Expressing said at least one or more polynucleotides in said host cell under conditions sufficient for secretion of said protein of interest encoded by the at least one or more polynucleotides; and
   (e) Contacting said host cells of step (d) with means for specifically detecting said protein of interest bound non-covalently by said second label and detecting host cells which display the protein of interest on their surface, wherein the means for specifically detecting said protein of interest is one of polyclonal antibody, monoclonal antibody, scFv-Fc, scFv, (Fab')$_2$, Fab, minibody, diabody, or VHH antibody.

2. Method according to claim 1, wherein the protein encoded by the at least one or more polynucleotides is a multimer.

3. Method according to claim 1, wherein the protein encoded by the at least one or more polynucleotides comprises a signal peptide.

4. Method according to claim 1, wherein the host cell is selected from mammalian, yeast or insect cells.

5. Method according to claim 4, wherein the yeast host cell is selected from the group comprising *Saccharomyces cerevisiae*, *Hansenula polymorpha*, *Schizosaccharomyces pombe*, *Schwanniomyces occidentalis*, *Kluyveromyceslactis*, *Yarrowia lipolytica* and *Pichia pastoris*.

6. Method according to claim 4, wherein the mammalian host cell is selected from the group comprising HEK293, HEK293T, HEK293E, HEK 293F, NS0, per.C6, MCF-7, HeLa, Cos-1, Cos-7, PC-12, 3T3, Vero, vero-76, PC3, U87, SAOS-2, LNCAP, DU145, A431, A549, B35, H1299, HUVEC, Jurkat, MDA-MB-231, MDA-MB-468, MDA-MB-435, Caco-2, CHO, CHO-K1, CHO-B11, CHO-DG44, BHK, AGE1.HN, Namalwa, WI-38, MRC-5, HepG2, L-929, RAB-9, SIRC, RK13, 11B11, 1D3, 2.4G2, A-10, B-35, C-6, F4/80, IEC-18, L2, MH1C1, NRK, NRK-49F, NRK-52E, RMC, CV-1, BT, MDBK, CPAE, MDCK.1, MDCK.2, and D-17.

7. Method according to claim 1, wherein the method further comprises selecting the host cells.

8. Method according to claim 1, wherein the host cells selected display the protein of interest of altered phenotype.

9. Method according to claim 8, wherein the altered phenotype is determined by comparing said host cells of step (e) to a reference sample.

10. Method according to claim 1, wherein the protein of interest encoded by the at least one or more polynucleotides of step (a) comprises at least one Fc-domain homodimer.

11. Method according to claim 10, wherein the at least one Fc-domain homodimer is one of human IgG1, human IgG2, murine IgG2a, murine IgG2b, or murine IgG3; or sequence variants thereof.

12. Method according to claim 10, wherein the Fc-domain-containing protein is an N-terminal Fc-domain fusion protein, C-terminal Fc-domain fusion protein or an antibody.

13. Method according to claim 12, wherein the antibody is a monoclonal antibody.

14. Method according to claim 1, wherein the second label specifically binds Fc domains of human IgG1, human IgG2, murine IgG2a, murine IgG2b, or murine IgG3.

15. Method according to claim 1, wherein the second label comprises the amino acid sequence according to SEQ ID NO: 1 and/or the amino acid sequence according to SEQ ID NO: 2.

16. Method according to claim 1, wherein the second label comprises the amino acid sequence of SEQ ID NO: 3.

17. Method according to claim 1, wherein the detection of step (e) further comprises:
(i) contacting said host cell with a detectably labeled antibody or antibody fragment, which specifically binds to Fc domains of human IgG1, human IgG2, murine IgG2a, murine IgG2b, or murine IgG3; or sequence variants thereof
(ii) contacting the host cell with an antigen and/or epitope specifically bound by the antibody bound to the second label, which is coupled to a further detectable label distinct from the label used in (i);
(iii) detecting the labels of (i) and/or (ii) on said host cells;
(iv) selecting host cells that display altered amounts of the label used in (i), and/or the label used in (ii) and/or display altered amounts of both labels compared to a reference sample.

18. Method according to claim 17, wherein the detectably labeled antibody or antibody fragment of step (e) specifically binds to kappa or lambda light chains of human or murine IgG1, human IgG2, murine IgG2a, murine IgG2b, or murine IgG3; or sequence variants thereof.

19. Method according to claim 17, wherein the labels of (i) and (ii) and/or the selection step (iv) comprise flow cytometry and/or FACS and/or microfluidics.

20. Method according to claim 1, wherein steps (a)-(e) are re-iterated.

21. Method according to claim 1, wherein the host cell is a yeast cell and wherein step (a) further comprises mating of at least a first and second yeast cell, whereby said first and second host cells comprise different polynucleotides of which at least one encodes a Fc domain-containing fusion protein and whereby said polynucleotides of said first and second host cell comprise at least one distinct selectable marker.

22. Method according to claim 21, wherein said first yeast cell comprises polynucleotides encoding immunoglobulin light chains and/or wherein said second yeast cell comprises polynucleotides encoding immunoglobulin heavy chains.

23. Method according to claim 22, wherein said first yeast cell comprises polynucleotides encoding an immunoglobulin light chain library and wherein said second yeast cell comprises polynucleotides encoding immunoglobulin heavy chains of pre-determined affinity to the protein of interest.

24. The method according to claim 1, wherein said polyclonal antibody, monoclonal antibody, scFv-Fc, scFv, (Fab')$_2$, Fab, minibody, diabody, or VHH antibody is coupled to a further label, wherein the further label is a fluorescent label or radioisotope.

\* \* \* \* \*